(12) United States Patent
Botta et al.

(10) Patent No.: US 11,814,366 B2
(45) Date of Patent: Nov. 14, 2023

(54) ANTIVIRAL COMPOUNDS AND USE THEREOF

(71) Applicant: UNIVERSITA DEGLI STUDI DI SIENA, Siena (IT)

(72) Inventors: Maurizio Botta, Castelnuovo Berardenga (IT); Filippo Canducci, Milan (IT); Valeria Cagno, Geneva (CH); David Lembo, Turin (IT); Cristina Tintori, Chiesina Uzzanese (IT); Annalaura Brai, Siena (IT); Nastasja Palombi, Siena (IT)

(73) Assignee: UNIVERSITA DEGLI STUDI DI SIENA, Siena (IT)

(*) Notice: Subject to any disclaimer, the term of this patent is extended or adjusted under 35 U.S.C. 154(b) by 109 days.

(21) Appl. No.: 16/981,346

(22) PCT Filed: Mar. 18, 2019

(86) PCT No.: PCT/EP2019/056717
§ 371 (c)(1),
(2) Date: Sep. 16, 2020

(87) PCT Pub. No.: WO2019/175436
PCT Pub. Date: Sep. 19, 2019

(65) Prior Publication Data
US 2021/0070737 A1    Mar. 11, 2021

(30) Foreign Application Priority Data
Mar. 16, 2018  (IT) .......................... 102018000003680

(51) Int. Cl.
*C07D 403/06* (2006.01)
*A61K 31/427* (2006.01)
(Continued)

(52) U.S. Cl.
CPC .......... *C07D 403/06* (2013.01); *A61K 31/427* (2013.01); *A61K 31/513* (2013.01);
(Continued)

(58) Field of Classification Search
CPC ........................... C07D 403/06; C07D 417/06
See application file for complete search history.

(56) References Cited

U.S. PATENT DOCUMENTS 3,917,645 A    11/1975  Althuis
2005/0049267 A1*  3/2005  Suto .................... C07D 405/06
                                                    514/270

FOREIGN PATENT DOCUMENTS

WO    03074497 A1    9/2003
WO    2004028535 A1  4/2004
(Continued)

OTHER PUBLICATIONS

McKee et al., "Pin1-modulating compounds and methods of use thereof", Chemical Abstracts Service, XP002790749, 2003, Database accession No. 2003:719458, pp. 1-2.
(Continued)

*Primary Examiner* — Shengjun Wang
(74) *Attorney, Agent, or Firm* — Lucas & Mercanti, LLP

(57) ABSTRACT

The present invention relates to compounds of formula (I), their use as medicaments, in particular as broad spectrum antiviral agents, their combination with a further antiviral agent and relative pharmaceutical compositions. In particular, the compounds of the invention are useful in the treatment of a disease caused by an enveloped virus.

11 Claims, 2 Drawing Sheets

(51) Int. Cl.
  *A61P 31/14*    (2006.01)
  *A61P 31/22*    (2006.01)
  *A61P 31/18*    (2006.01)
  *A61P 31/16*    (2006.01)
  *A61K 31/513*    (2006.01)
  *A61K 45/06*    (2006.01)
  *C07D 417/06*    (2006.01)

(52) U.S. Cl.
  CPC .............. *A61K 45/06* (2013.01); *A61P 31/14* (2018.01); *A61P 31/16* (2018.01); *A61P 31/18* (2018.01); *A61P 31/22* (2018.01); *C07D 417/06* (2013.01)

(56) References Cited

FOREIGN PATENT DOCUMENTS

| | | |
|---|---|---|
| WO | 2004093803 A2 | 11/2004 |
| WO | 2011160024 A2 | 12/2011 |

OTHER PUBLICATIONS

Althuis et al., "2-(Methylthio)-3-(2-pyrrolyl)acrylates", Chemical Abstracts Service, XP002790750, 1974, Database accession No. 1974:551989, pp. 1-2.
McKee et al., "Pin1-modulating compounds and methods of use for the treatment of Pin1-associated diseases, including cancer" Chemical Abstracts Service, XP002790751, 2004, Database accession No. 2004:291950, pp. 1-2.
Bao et al., "Pin1-modulating compounds and methods of use for the treatment of Pin1-associated diseases, including cancer", Chemical Abstracts Service, XP002790752, 2004, Database accession No. 2004:927010, pp. 1-2.
Jiang et al., "Design, synthesis, and biological activity of novel 5-((arylfuran/1H-pyrrol-2-yl)methylene)-2-thioxo-3-(3-(trifluoromethyl)phenyl)thiazolidin-4-ones as HIV-1 fusion inhibitors targeting gp41", Chemical Abstracts Service, XP002790753, 2010, Database accession No. 2010:1633976, pp. 1-4.
International Search Report and Written Opinion for International Application No. PCT/EP2019/056717, (17 Pages) (dated May 21, 2019).

\* cited by examiner

ANTIVIRAL COMPOUNDS AND USE THEREOF

CROSS-REFERENCE TO RELATED APPLICATIONS

This application is a 371 of PCT/EP2019/056717, filed Mar. 18, 2019, which claims the benefit of Italian Patent Application No. 102018000003680, filed Mar. 16, 2018.

FIELD OF THE INVENTION

The present invention relates to compounds of formula (I), their use as medicaments, in particular as broad spectrum antiviral agents, their combination with a further antiviral agent and relative pharmaceutical compositions. In particular, the compounds of the invention are useful in the treatment of a disease caused by an enveloped virus.

BACKGROUND TO THE INVENTION

It is estimated that there are approximately 500,000 unknown mammalian viruses in wildlife reservoirs (Anthony et al, 2013). The antivirals drugs on the market are virus specific, with the exception of ribavirin, whose mechanism of action is still debated and whose adverse effects are often not negligible. However the interest of the scientific committee is now moving on the search of new broad spectrum antivirals able to fight both old and new emerging viruses.

Components involved in viral entry process such as lipoproteins and co-receptors are among possible targets of interest to develop new broad spectrum antiviral molecules. Furthermore, compounds that cause an alteration of virus envelope composition or rigidity can impair viral fusion with the host cell while not being toxic for the cell. The feasibility of this approach has been demonstrated by cholesterol depletion (Pollock et al, 2010), inverted cone phospholipids (Arouri et al, 2013) and virolytic antiviral peptides (Sample et al, 2013). The strategy to target the viral envelope can be successful considering that the majority of emerging viruses having caused recent outbreaks are enveloped (i.e. Ebola, Zika, MERS) as are threatening viruses such as Hendra, Nipah and Lassa. Moreover viruses established in the human population and presenting important public health problem like HIV, HCV, HBV, herpesviruses and Flu are also enveloped viruses.

WO 2011/160024 relates to 3-N-cycloalkyl-5-substituted-2-thioxothiazolidin-4-one useful as antiviral agents.

Therefore, there is still the need to develop broad spectrum antiviral agents that are effective against enveloped viruses.

BRIEF DESCRIPTION OF THE INVENTION

In the present invention, the authors have surprisingly found novel compounds of formula (I) as defined below, which can act as broad spectrum antiviral agents. As a matter of fact, the compounds of the invention exhibit low EC50 and EC90 values against a variety of enveloped viruses, while not being toxic for the cell. Advantageously, the compounds of the invention are also effective against viral strains that are resistant to standard antiviral therapy (e.g. acyclovir).

In particular, it was surprisingly found that compounds of formula (I) act exclusively on enveloped viruses. Unexpectedly, the activity of the compounds is not due to interactions with the human cell membrane nor to the inhibition of viral entry. Rather, the compounds of the present invention surprisingly act by oxidising lipids in the viral envelope, thus destabilizing it.

The compounds of the present invention were surprisingly found to act as oxidants of the unsaturated lipid component of virus envelope and to induce change in lipid membrane flexibility. In the present invention it was surprisingly found that the compounds possess a radical-based mechanism activated by light, including production of $*O_2$ and oxidation of unsaturated lipid membrane of virus envelope. This creates the destabilization of the lipid membrane of virus envelope. Then, virus-cell fusion and consequently viral entry is permanently impaired. Compounds' selectivity is related to the membrane repair mechanisms present in eukaryotic cells (Sandra T. Cooper and Paul L. McNeil Membrane Repair: Mechanisms and Pathophysiology Physiol Rev. 2015 October; 95(4): 1205-1240.) but not in viruses. Among well-known repair mechanisms there are endogenous antioxidant agents such as catalases, peroxidases and the lysosomal degradation system that mediates destruction of the damaged lipids and lipoprotein. Furthermore, the lipid component of the envelope, which is thought to originate from the host cell, is per se static and devoid of repair mechanisms. The molecule of the present invention can be of great use in different applications. They may be formulated as vaginal microbicide to prevent sexually transmitted diseases and as nasal spray to prevent and treat respiratory infections. Moreover, they represent an interesting tool to fight emerging enveloped viruses for which there is no time to develop specific antiviral molecules nor vaccines.

The compounds of the invention may be used to treat diseases caused by any enveloped virus such as Ebola, Zika, MERS viruses as well as Hendra, Nipah and Lassa. Moreover, viruses established in the human population and presenting important public health problem like HIV, HCV, HBV, herpesviruses and Flu are enveloped viruses and may be treated with the compounds of the invention.

In the present invention, the authors have identified a new class of compounds altering membrane flexibility able to treat viral disorders.

The compounds presented in this invention (Formula I) showed:
1. The ability to suppress HIV-1 replication in infected cells;
2. The ability to suppress Zika virus (ZKV) replication in infected cells;
3. The ability to suppress Herpes 1 virus (HSV-1) replication in infected cells;
4. The ability to suppress Herpes 2 virus (HSV-2) replication in infected cells;
5. The ability to suppress Influenza virus (IV) replication in infected cells;
6. The ability to suppress Respiratory Syncytial Virus (RSV) replication in infected cells;
7. The ability to suppress Cytomegalovirus (CMV) replication in infected cells;
8. The ability to suppress Vesicular Stomatitis Virus (VSV) replication in infected cells;
9. The ability to suppress Dengue Virus (DENV) replication in infected cells.

It is therefore an object of the invention a compound of formula (I):

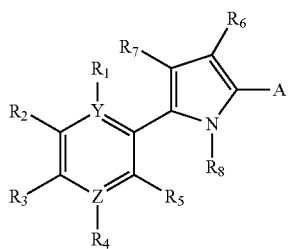

(I)

or a salt, solvate or stereoisomer thereof, wherein:

Y and Z are each independently C or N, when Y is N, $R_1$ is a lone pair and when Z is N, $R_4$ is a lone pair;

$R_1$, $R_2$, $R_3$, $R_4$, $R_5$, $R_6$, $R_7$ are each independently selected from the group consisting of: H, halogen, alkoxy, $OR_A$, $SR_A$, $S(=O)(=O)-R_A$, $SO_2NHR_A$, $COOR_B$, $OC(O)R_B$, $NR_AR_B$, $OP(O)(OR_A)_2$, $NHC(O)R_A$, $CONR_AR_B$, $NO_2$, $CN$,

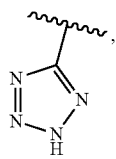

substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted aryl and substituted or unsubstituted heteroaryl, wherein the substituted $C_1$-$C_6$ alkyl, the $C_2$-$C_6$ substituted alkenyl, the substituted $C_2$-$C_6$ alkynyl, the substituted aryl, the substituted heteroaryl are each independently substituted by one or more substituents selected from the group consisting of: halogen, substituted or unsubstituted phenyl, $OR_A$, $COOR_B$, $OC(O)R_B$, $NR_AR_B$, $OP(O)(OR_A)_2$, $OC(O)NR_AR_B$, $NHC(O)OR_A$, $NHC(O)R_A$ and $CONR_AR_B$;

A is

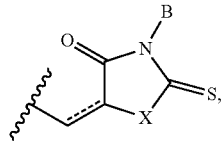

the dashed line represents an optional double bond, X is

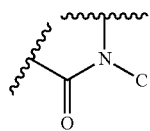

or S;

$R_8$ is selected from the group consisting of: H, substituted or unsubstituted $C_1$-$C_6$ alkyl, substituted or unsubstituted $C_2$-$C_6$ alkenyl, substituted or unsubstituted $C_2$-$C_6$ alkynyl and substituted or unsubstituted aryl, wherein the substituted $C_1$-$C_6$ alkyl, the substituted $C_2$-$C_6$ alkenyl, the substituted $C_2$-$C_6$ alkynyl or the substituted aryl are each independently substituted by one or more substituents selected from the group consisting of: halogen, substituted or unsubstituted phenyl, $OR_A$, $COOR_B$, $OC(O)R_B$, $NR_AR_B$, $OP(O)(OR_A)_2$, $OC(O)NR_AR_B$, $NHC(O)OR_A$, $NHC(O)R_A$ and $CONR_AR_B$;

$R_A$ and $R_B$ are each independently selected from: H, $C_1$-$C_6$ alkyl, unsubstituted or substituted aralkyl, haloalkyl, or $R_A$ and $R_B$ together with the nitrogen, sulfur, or oxygen to which they are attached, form a 4-7 membered saturated or partially unsaturated ring optionally containing one or more additional heteroatoms independently selected from N, S and O the ring being optionally substituted by one, two or more groups independently selected from halogen, $C_1$-$C_6$ alkyl, haloalkyl, OH and alkoxy;

B and C are each independently selected from: H, unsubstituted or substituted $C_1$-$C_{10}$ alkyl, $C_2$-$C_{10}$ alkenyl, $C_2$-$C_{10}$ alkynyl, and unsubstituted or substituted phenyl; wherein the substituted $C_1$-$C_{10}$ alkyl or the substituted phenyl are independently substituted by one or more substituents selected from substituted or unsubstituted phenyl, halogen, $C_3$-$C_{10}$ cycloalkyl, $C_3$-$C_{10}$ heterocycloalkyl, substituted or unsubstituted heteroaryl, $OR_A$, $COOR_B$, $OC(O)R_B$, $NR_AR_B$, $OP(O)(OR_A)_2$, $OC(O)NR_AR_B$, $NHC(O)OR_A$, $NHC(O)R_A$ and $COONR_AR_B$;

provided that compounds:

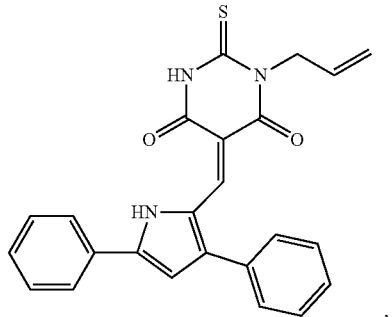

,

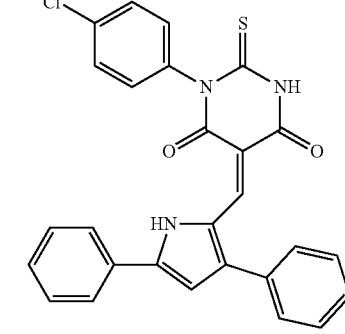

;

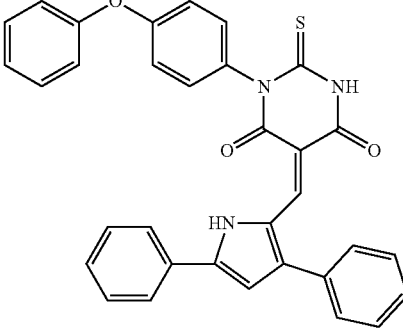

;

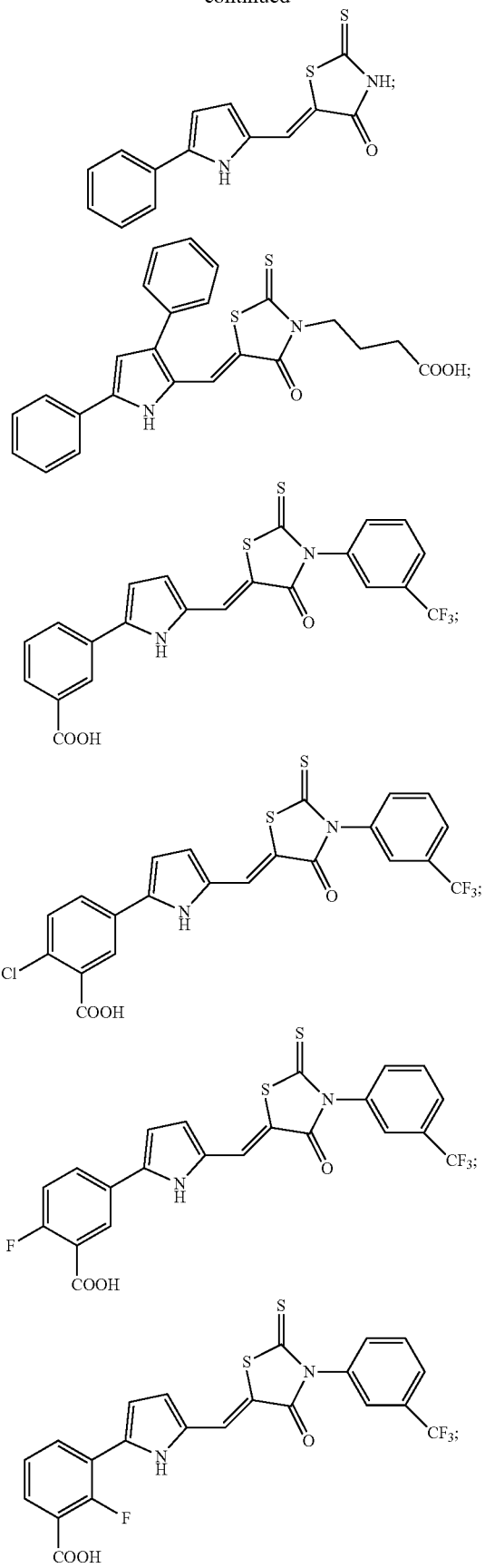
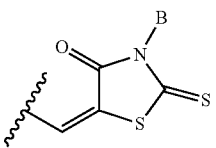
are excluded and provided that when A is
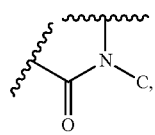
B is not norbornane or adamantane. In particular, when X is
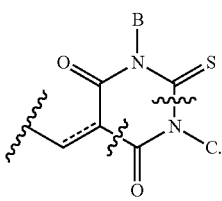
A is
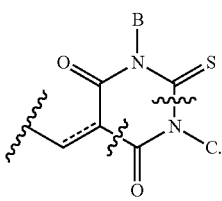
More preferably, when X is
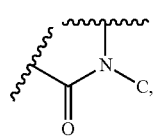
A is
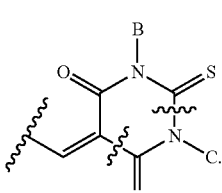

Preferably, when X is

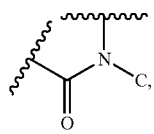

the C=O group in X is bonded to the carbon adjacent to the optional double bond and the N—C group in X is bonded to C=S.

Preferably, A is

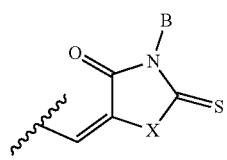

wherein B and X are as defined above.

Preferably, A is selected from the group consisting of:

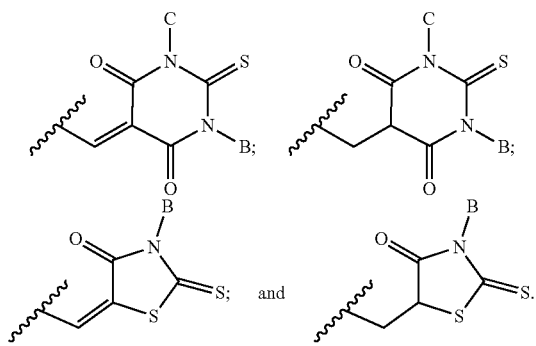

Preferably, $R_8$ is H. Then, the present invention also provides compounds of formula (II), wherein Z, Y, A, $R_1$, $R_2$, $R_3$, $R_4$, $R_5$, $R_6$ and $R_7$ are as defined above:

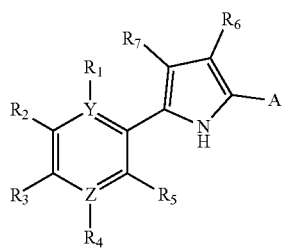

(II)

Preferably, B and C are each independently selected from the group consisting of: H, $(CH_2)_n$phenyl, $(CH_2)_n C_3$-$C_{10}$cycloalkyl, $(CH_2)_n C_3$-$C_{10}$heterocycloalkyl, $(CH_2)_n$heteroaryl, $C_2$-$C_{10}$ alkenyl, $C_2$-$C_{10}$ alkynyl and phenyl, wherein n is an integer from 1 to 3, wherein said $(CH_2)_n$phenyl, $(CH_2)_n C_3$-$C_{10}$cycloalkyl, $(CH_2)_n C_3$-$C_{10}$heterocycloalkyl, $(CH_2)_n$heteroaryl or phenyl is optionally substituted by one or more substituents selected from the group consisting of: halogen, $OR_A$ and $C_1$-$C_3$ alkyl, or a salt, solvate or stereoisomer thereof.

Preferably, $R_A$ and $R_B$ are each independently selected from: H, $C_1$-$C_3$ alkyl, haloalkyl, or $R_A$ and $R_B$ together with the nitrogen or oxygen to which they are attached, form a 4-7 membered saturated or partially unsaturated ring optionally containing one or more additional heteroatoms independently selected from N, S and O the ring being optionally substituted by one, two or more groups independently selected from halogen, $C_1$-$C_6$ alkyl, haloalkyl, OH and alkoxy.

Preferably, $R_6$ and $R_7$ are H.

Preferably, $R_1$, $R_2$, $R_3$, $R_4$, $R_5$ are independently selected from halogen, haloalkyl, $OR_A$ and $COOR_B$.

Preferably, A is selected from:

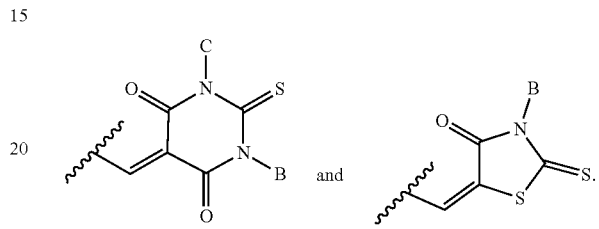

Preferably, B and C are independently selected from: H, unsubstituted $C_1$-$C_{10}$ alkyl or substituted $C_1$-$C_{10}$ alkyl, wherein the substituted $C_1$-$C_{10}$ alkyl is substituted by one or more substituents selected from halogen, substituted phenyl or unsubstituted phenyl, the phenyl being preferably substituted by Cl, OH or $C_1$-$C_3$ alkyl.

Preferably, Y and Z are C.

Preferably, $R_1$ and $R_5$ are each independently H or halogen.

Preferably, $R_2$ and $R_4$ are each independently H, $OR_A$, haloalkyl or halogen.

Preferably, $R_3$ is H, $COOR_B$ (preferably COOH), CN,

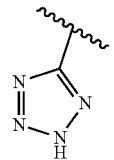

or $OR_A$(preferably OH).

Preferably, $R_8$ is H or $C_1$-$C_3$ alkyl (preferably methyl).

Preferably, $R_A$ and $R_B$ are H.

In a preferred embodiment, the present invention provides a compound of formula (I) as defined above, wherein:
$R_6$ and $R_7$ are H;
$R_1$, $R_2$, $R_3$, $R_4$, $R_5$ are independently selected from halogen, haloalkyl, $OR_A$ and $COOR_B$;
A is selected from:

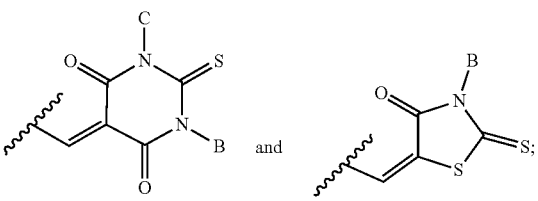

B and C are independently selected from: H, unsubstituted $C_1$-$C_{10}$ alkyl or substituted $C_1$-$C_{10}$ alkyl, wherein the substituted $C_1$-$C_{10}$ alkyl is substituted by one or more substituents selected from halogen, substituted phenyl or unsubstituted phenyl, the phenyl being preferably substituted by at least one of Cl, OH or $C_1$-$C_3$ alkyl.

In another preferred embodiment, the present invention provides a compound of formula (I) as defined above, or a salt, solvate or stereoisomer thereof, wherein:

Y and Z are C;

$R_1$ and $R_5$ are each independently H or halogen (preferably chlorine);

$R_2$ and $R_4$ are each independently H, $OR_A$ (preferably OH), haloalkyl (preferably $CF_3$) or halogen (preferably F);

$R_3$ is H, $COOR_B$ (preferably COOH), CN,

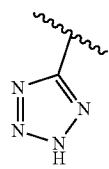

or $OR_A$ (preferably OH);

$R_6$ and $R_7$ are H;

A is

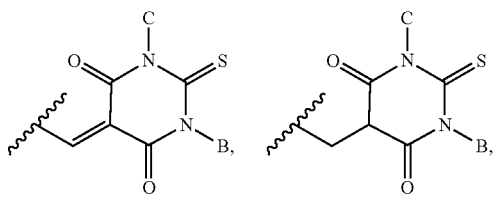

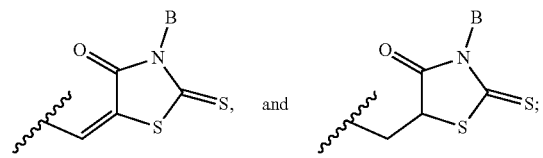

$R_8$ is H or $C_1$-$C_3$ alkyl (preferably methyl);

$R_A$ and $R_B$ are H;

B and C are each independently selected from: H, $(CH_2)_n$phenyl, $(CH_2)_nC_3$-$C_{10}$cycloalkyl, $(CH_2)_nC_3$-$C_{10}$heterocycloalkyl, $(CH_2)_n$heteroaryl, $C_2$-$C_{10}$ alkenyl, $C_2$-$C_{10}$ alkynyl and phenyl, wherein n is an integer from 1 to 3, wherein said $(CH_2)_n$phenyl, $(CH_2)_nC_3$-$C_{10}$cycloalkyl, $(CH_2)_nC_3$-$C_{10}$heterocycloalkyl, $(CH_2)$heteroaryl or phenyl is optionally substituted by one or more substituents selected from the group consisting of: halogen, $OR_A$ (preferably OH) and $C_1$-$C_3$ alkyl.

Preferably, when B and/or C is substituted $(CH_2)_n$phenyl, $(CH_2)_nC_3$-$C_{10}$cycloalkyl, $(CH_2)_nC_3$-$C_{10}$heterocycloalkyl or $(CH_2)_n$heteroaryl, the phenyl, $C_3$-$C_{10}$cycloalkyl, $C_3$-$C_{10}$heterocycloalkyl, heteroaryl is substituted and the $(CH)_n$ is not substituted.

Preferably, the compound is:

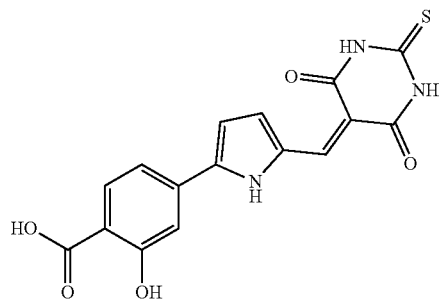

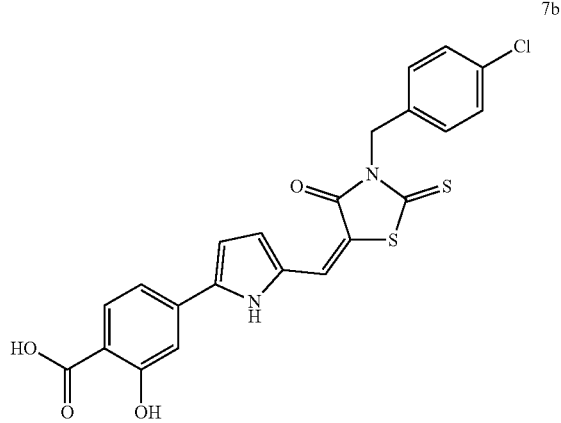

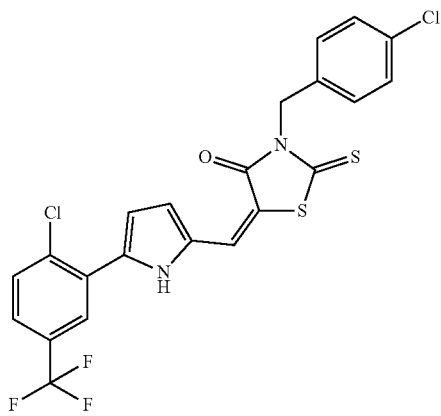

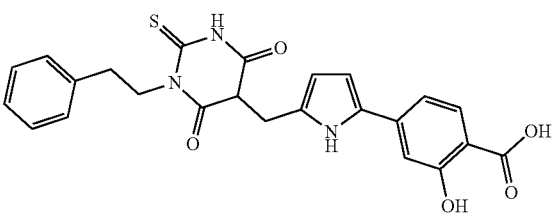

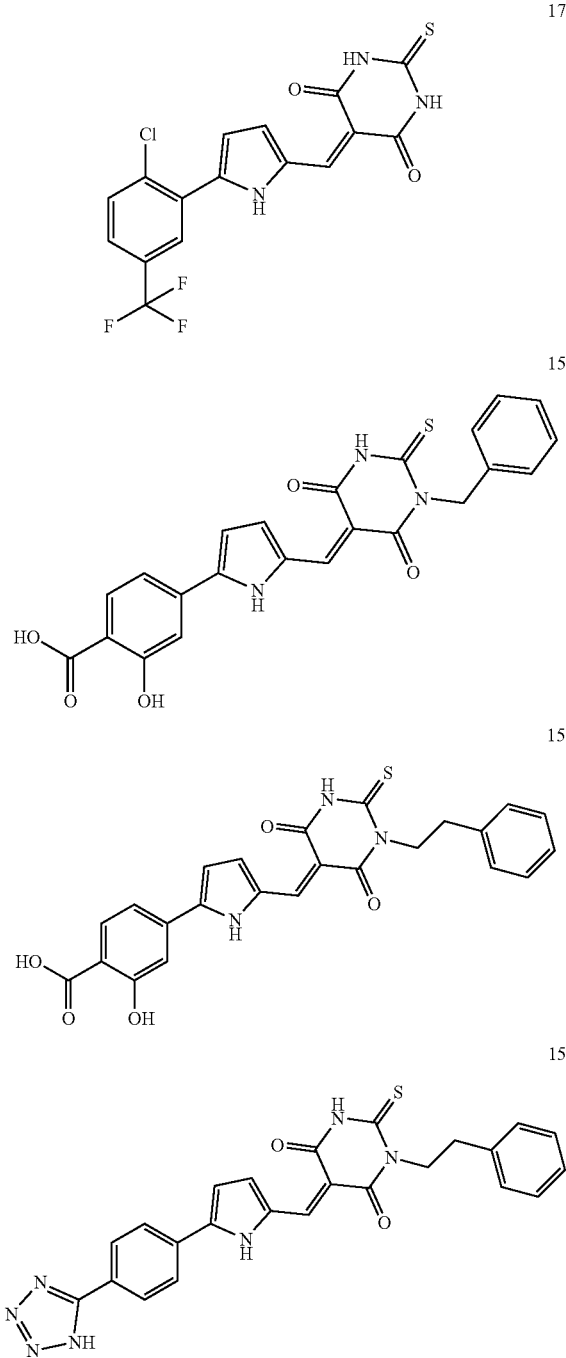
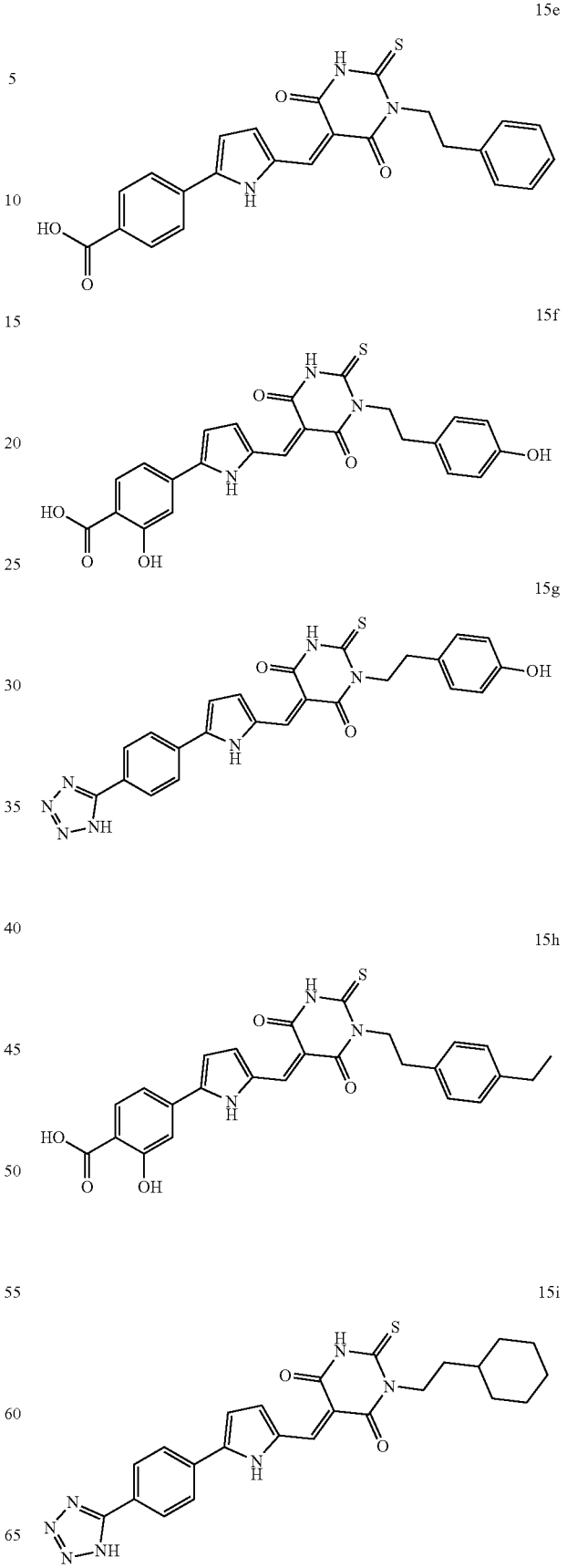

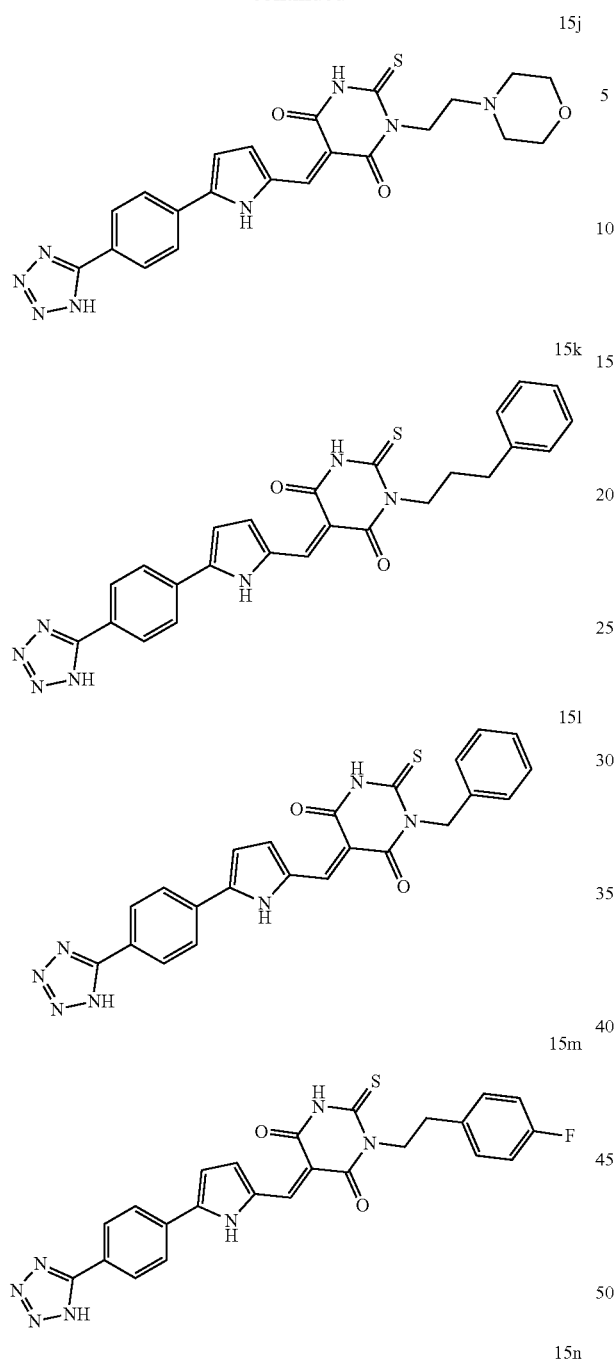
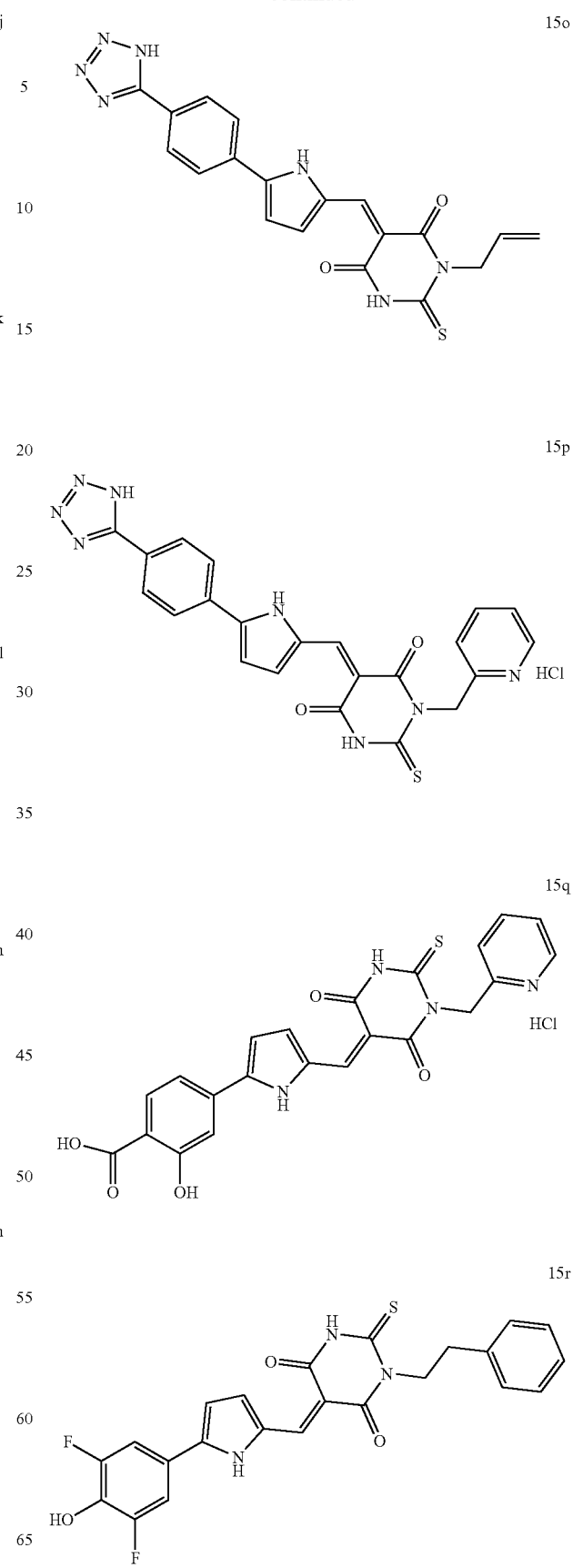

15s

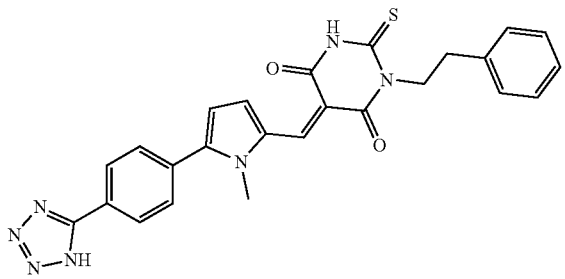

or a salt, solvate or stereoisomer thereof.

The invention also provides the compound or salt, solvate or stereoisomer thereof as defined above for use as a medicament.

Preferably, the compound, or salt, solvate or stereoisomer thereof as defined above is an envelope destabilizing compound, i.e. it destabilizes a viral envelope. Preferably, the compound, or salt, solvate or stereoisomer thereof as defined above destabilizes a viral envelope by oxidising at least one lipid in the viral envelope.

Also preferably, the compound, or salt, solvate or stereoisomer thereof as defined above is for use in the treatment of a viral disease. Still preferably, the viral disease is caused by an enveloped virus.

Preferably, the enveloped virus is selected from the group consisting of: Human Immunodeficiency Virus 1 (HIV-1), Human Immunodeficiency Virus 2 (HIV-2), Herpes 1 virus (HSV-1), Herpes 2 virus (HSV-2), Influenza Virus, Respiratory Syncytial Virus (RSV), Cytomegalovirus (CMV), Zika Virus (ZKV), Dengue Virus, West Nile Virus, Lassa Virus, Ebola Virus, Lloviu virus, Bundibugyo virus, Reston virus, Sudan virus, Tai Forest virus, Marburg virus, Ravn virus (RAVV), Pneumovirus, Junin Virus, Rift Valley fever virus, La Crosse Virus, Porcine Reproductive And Respiratory Syndrome Virus, Poxvirus, Bovine Viral Diarrhea Norovirus, SARS Coronavirus, Chikunguya Virus, Hepatitis C Virus, Hepatitis B Virus, Schmallenberg virus, African swine fever virus, Eastern Equine Encephalitis Virus, Cowpox virus, Western Equine Encephalitis Virus, Nipah Virus, Omsk hemorrhagic fever Virus, Venezuelan Equine Encephalitis Virus, Human parainfluenza viruses, Japanese Encephalitis Virus, Tick Borne Encephalitis Virus, Russian spring-summer encephalitis (RSSE) virus, Yellow Fever Virus, Newcastle Virus, Virus (BVDV), Parainfluenza virus type 5 (PIV5), Border Disease Virus (BDV) of sheep, Classical Swine Fever Virus (CSFV), Vesicular Stomatitis Virus (VSV) and HSV-2 acyclovir resistant (HSV-2 Acy R). More preferably, the enveloped virus is selected from the group consisting of: HIV-1, HSV-1, HSV-2, HCMV, RSV, VSV, H1N1, DENV-2 and ZKV.

Preferably, the enveloped virus is resistant to at least one antiviral agent. Preferably, the enveloped virus is resistant to at least one antiviral agent selected from the group consisting of: acyclovir, ribavirine, a nucleoside analogue reverse-transcriptase inhibitor, a non-nucleoside analogue reverse-transcriptase inhibitor, a nucleotide analogue reverse-transcriptase inhibitor, an integrase inhibitor, a NS3/4A serine protease inhibitor, a NS5B polymerase inhibitor, interferon alpha, Maraviroc, Highly active antiretroviral therapy (HAART), Brivudin, Famiciclovir, Penciclovir, Ganciclovir, Amantadine, Rimantadine, Oseltamivir and Zanamivir, preferably the nucleoside analogue reverse-transcriptase inhibitor is selected from the group consisting of: Zidovudine, Didanosine, Lamivudine, Emtricitabine and stavudine; preferably the non-nucleoside analogue reverse-transcriptase inhibitor is selected from the group consisting of: Efavirenz, Nevirapine, Etravirine and Rilpivirine; preferably the nucleotide analogue reverse-transcriptase inhibitor is Tenofovir; preferably the integrase inhibitor is selected from the group consisting of: Raltegravir, dolutegravir and elvitegravir; preferably the NS3/4A serine protease inhibitor is selected from the group consisting of: Boceprevir, Telaprevir and paritaprevir; preferably the NS5B polymerase inhibitor is selected from the group consisting of: ledipasvir, ombitasvir, Dasabuvir and Sofosbuvir; preferably the Highly active antiretroviral therapy (HAART) is selected from the group consisting of: Triumeq, Trizivir and Stribild.

More preferably, the enveloped virus is resistant to at least one of: acyclovir, Raltegravir, ribavirine and/or sofosbuvir.

It is another object of the present invention, the compound or salt, solvate or stereoisomer thereof for use as defined above in combination with at least one further antiviral agent. Said further antiviral agent is preferably selected from the group consisting of: acyclovir, ribavirine, a nucleoside analogue reverse-transcriptase inhibitor, a non-nucleoside analogue reverse-transcriptase inhibitor, a nucleotide analogue reverse-transcriptase inhibitor, an integrase inhibitor, a NS3/4A serine protease inhibitor, a NS5B polymerase inhibitor, interferon alpha, Maraviroc, Highly active antiretroviral therapy (HAART), Enfuvirtide, Entecavir, Lamivudine, Brivudin, Famiciclovir, Penciclovir, Ganciclovir, Amantadine, Rimantadine, Oseltamivir and Zanamivir.

Preferably, the nucleoside analogue reverse-transcriptase inhibitor is selected from the group consisting of: Zidovudine, Didanosine, Lamivudine, Emtricitabine and stavudine.

Preferably, the non-nucleoside analogue reverse-transcriptase inhibitor is selected from the group consisting of: Efavirenz, Nevirapine, Etravirine and Rilpivirine.

Preferably, the nucleotide analogue reverse-transcriptase inhibitor is Tenofovir.

Preferably, the integrase inhibitor is selected from the group consisting of: Raltegravir, dolutegravir and elvitegravir.

Preferably, the NS3/4A serine protease inhibitor is selected from the group consisting of: Boceprevir, Telaprevir and paritaprevir.

Preferably, the NS5B polymerase inhibitor is selected from the group consisting of: ledipasvir, ombitasvir, Dasabuvir and Sofosbuvir.

Preferably, the Highly active antiretroviral therapy (HAART) is selected from the group consisting of: Triumeq, Trizivir and Stribild.

In another aspect, the present invention provides a pharmaceutical composition comprising at least one compound or salt, solvate or stereoisomer as defined above and at least one pharmaceutically acceptable excipient and/or diluent.

Preferably, the pharmaceutical composition further comprises at least one additional antiviral agent. More preferably, the pharmaceutical composition further comprises at least one additional antiviral agent selected from the group consisting of: acyclovir, ribavirine, a nucleoside analogue reverse-transcriptase inhibitor, a non-nucleoside analogue reverse-transcriptase inhibitor, a nucleotide analogue reverse-transcriptase inhibitor, an integrase inhibitor, a NS3/4A serine protease inhibitor, a NS5B polymerase inhibitor, interferon alpha, Maraviroc, Highly active antiretroviral therapy (HAART), Enfuvirtide, Entecavir, Lamivudine, Brivudin, Famiciclovir, Penciclovir, Ganciclovir, Amantadine, Rimantadine, Oseltamivir and Zanamivir, preferably the nucleoside analogue reverse-transcriptase inhibitor is selected from the group consisting of: Zidovudine, Didanosine, Lamivudine, Emtricitabine and stavudine; preferably the non-nucleoside analogue reverse-transcriptase inhibitor is selected from the group consisting of: Efavirenz, Nevirapine, Etravirine and Rilpivirine; preferably the nucleotide analogue reverse-transcriptase inhibitor is Tenofovir; preferably the integrase inhibitor is selected from the group consisting of: Raltegravir, dolutegravir and elvitegravir; preferably the NS3/4A serine protease inhibitor is selected from the group consisting of: Boceprevir, Telaprevir and paritaprevir; preferably the NS5B polymerase inhibitor is selected from the group consisting of: ledipasvir, ombitasvir, Dasabuvir and Sofosbuvir; preferably the Highly active antiretroviral therapy (HAART) is selected from the group consisting of: Triumeq, Trizivir and Stribild.

In yet another embodiment, the present invention provides the pharmaceutical composition as defined above for use in the treatment of a viral disease, preferably said viral disease is caused by an enveloped virus, preferably selected from the group consisting of: Human Immunodeficiency Virus 1 (HIV-1), Human Immunodeficiency Virus 2 (HIV-2), Herpes 1 virus (HSV-1), Herpes 2 virus (HSV-2), Influenza Virus, Respiratory Syncytial Virus (RSV), Cytomegalovirus (CMV), Zika Virus (ZKV), Dengue Virus, West Nile Virus, Lassa Virus, Ebola Virus, Lloviu virus, Bundibugyo virus, Reston virus, Sudan virus, Tai Forest virus, Marburg virus, Ravn virus (RAVV), Pneumovirus, Junin Virus, Rift Valley fever virus, La Crosse Virus, Porcine Reproductive And Respiratory Syndrome Virus, Poxvirus, Bovine Viral Diarrhea Norovirus, SARS Coronavirus, Chikunguya Virus, Hepatitis C Virus, Hepatitis B Virus, Schmallenberg virus, African swine fever virus, Eastern Equine Encephalitis Virus, Cowpox virus, Western Equine Encephalitis Virus, Nipah Virus, Omsk hemorrhagic fever Virus, Venezuelan Equine Encephalitis Virus, Human parainfluenza viruses, Japanese Encephalitis Virus, Tick Borne Encephalitis Virus, Russian spring-summer encephalitis (RSSE) virus, Yellow Fever Virus, Newcastle Virus, Virus (BVDV), Parainfluenza virus type 5 (PIV5), Border Disease Virus (BDV) of sheep, Classical Swine Fever Virus (CSFV), Vesicular Stomatitis Virus (VSV) and HSV-2 acyclovir resistant (HSV-2 Acy R), more preferably the enveloped virus is selected from the group consisting of: HIV-1, HSV-1, HSV-2, HCMV, RSV, VSV, H1N1, DENV-2 and ZKV.

Preferably, said pharmaceutical composition is for topical administration. Preferably, said pharmaceutical composition is formulated as a vaginal capsule or as a nasal spray.

The expression "the compound destabilizes a viral envelope" or "envelope destabilizing compound" as used herein refers to a compound that is capable of inducing structural or functional changes to a viral envelope, resulting in a decrease in the stability of the viral envelope. For instance, compounds that destabilize the viral envelope may oxidise lipids in the viral envelope. The ability of a compound to oxidise lipids in the viral envelope may be measured as indicated in Example 9 below (determination of the lipid oxidation capability) or using other methods already published (Hollmann, A.; Castanho, M. A. R. B.; Lee, B.; Santos, N. C. Singlet Oxygen Effects on Lipid Membranes: Implications for the Mechanism of Action of Broad-Spectrum Viral Fusion Inhibitors. Biochem. J. 2014, 459 (1), 161-170; Cagno, V.; Tintori, C.; Civra, A.; Cavalli, R.; Tiberi, M.; Botta, L.; Brai, A.; Poli, G.; Tapparel, C.; Lembo, D.; et al. Novel Broad Spectrum Virucidal Molecules against Enveloped Viruses. 2018).

As used herein, the term "substituted" means that any one or more hydrogen atom(s), on any carbon atom, nitrogen atom or other atom of the specified group or moiety, may be independently replaced by any other substituent.

As used herein, the term "unsubstituted" means that the hydrogen atom(s), on any carbon atom, nitrogen atom or other atom of the specified group or moiety, are not be replaced by any other substituent.

As used herein, the term "halogen" or "halo" refers to fluoro, chloro, bromo, or iodo. Preferably, it refers to chloro or fluoro.

As used herein, the term "alkyl" refers to a linear or branched hydrocarbon chain radical, consisting solely of carbon and hydrogen atoms. Suitable examples of said alkyl include but are not limited to methyl, ethyl, n-propyl, isopropyl, butyl, sec-butyl, tert-butyl, pentyl, isopentyl, tert-pentyl, hexyl, heptyl, octyl, nonyl, decanyl, hexadecanyl, eicosanyl, etc. Preferred alkyl groups are: $C_1$-$C_{10}$ alkyl, $C_1$-$C_6$ alkyl, $C_1$-$C_3$ alkyl.

As used herein, the term "$C_1$-$C_{10}$ alkyl" refers to a linear or branched hydrocarbon chain radical, consisting solely of carbon and hydrogen atoms, having from one to ten carbon atoms. Suitable examples of $C_{1-10}$ alkyl include but are not limited to methyl, ethyl, n-propyl, isopropyl, butyl, sec-butyl, tert-butyl, pentyl, isopentyl, tert-pentyl, hexyl, heptyl, octyl, nonyl, decanyl. Suitable examples of "substituted $C_1$-$C_{10}$ alkyl" include benzyl, ethylbenzene and propylbenzene.

As used herein, the term "$C_1$-$C_6$ alkyl" refers to a linear or branched hydrocarbon chain radical, consisting solely of carbon and hydrogen atoms, having from one to six carbon atoms. Suitable examples of $C_1$-$C_6$ alkyl include but are not limited to methyl, ethyl, n-propyl, isopropyl, butyl, sec-butyl, tert-butyl, pentyl, isopentyl, tert-pentyl, hexyl.

As used herein, the term "$C_1$-$C_3$ alkyl" refers to a linear or branched hydrocarbon chain radical, consisting solely of carbon and hydrogen atoms, having from one to three carbon atoms. Suitable examples of $C_1$-$C_3$ alkyl are methyl, ethyl, n-propyl.

As used herein, the term "alkenyl" refers to a linear or branched unsaturated hydrocarbon chain radical, containing at least one carbon-carbon double bond, consisting solely of carbon and hydrogen atoms. Preferred alkenyl groups are $C_2$-$C_6$ alkenyl, having from two to six carbon atoms, and $C_2$-$C_{10}$ alkenyl, having from two to ten carbon atoms. Suitable examples of alkenyl include but are not limited to ethenyl, propenyl, allyl, isobuthenyl, pentenyl, prenyl, esenyl, etc.

As used herein, the term "alkynyl" refers to a linear or branched unsaturated hydrocarbon chain radical, containing at least one carbon-carbon triple bond, consisting solely of carbon and hydrogen atoms. Preferred alkynyl groups are $C_2$-$C_6$ alkynyl, having from two to six carbon atoms, and $C_2$-$C_{10}$ alkynyl, having from two to ten carbon atoms. Suitable examples of $C_2$-$C_6$ alkynyl include but are not limited to acetylenyl, ethynyl, propynyl, etc.

As used herein, the term "haloalkyl" group refers to a linear or branched alkyl group as defined herein above, wherein at least one hydrogen atom on any carbon atom is replaced by a halogen. "Haloalkyl" preferably is a linear or branched $C_1$-$C_{10}$ haloalkyl group, more preferably linear or branched $C_1$-$C_8$ haloalkyl group, more preferably linear or branched $C_1$-$C_6$ haloalkyl group, also preferably a linear or branched $C_1$-$C_4$ haloalkyl group, or a $C_1$-$C_2$ haloalkyl group, being in particular, $CHFCH(CH_3)(CH_2CH_2CH_3)$, $CH_2CH_2CH_2F$, $C_4F_9$, $CF_3$, $CHF_2$, $CH_2F$.

As used herein, the term "$C_1$-$C_{10}$ haloalkyl" refers to linear or branched alkyl group as defined herein above having from one to ten carbon atoms wherein at least one hydrogen on a carbon atom is replaced by halogen. Analogous definition is for $C_1$-$C_8$ haloalkyl, $C_1$-$C_6$ haloalkyl, $C_1$-$C_4$ haloalkyl and $C_1$-$C_4$ haloalkyl having from one to eight, one to six and one to four or one to two carbon atoms respectively.

As used herein, the term "alkoxy" denotes an organic unit having the general formula —OR, wherein R is an aliphatic group. An alkoxy group can be, for example, methoxy and ethoxy. Suitable examples of alkoxy groups also include, but are not limited to, propoxy, isopropoxy, isobutoxy, and tert-butoxy.

As used herein, the term "aryl" represents a mono or bicyclic aromatic ring system comprising of from 4 to 10 atoms, suitable examples of such an aryl are phenyl, indenyl, indanyl and naphthyl. Preferably, aryl is phenyl.

As used herein, the term "aralkyl" represents any univalent radical derived from an alkyl radical by replacing one or more hydrogen atoms by aryl groups, wherein the aryl is as defined herein above. A suitable example of such an aralkyl is benzyl.

As used herein, "substituted aralkyl" means that any one or more hydrogen atom(s), on any carbon atom, may be independently replaced by any other substituent. Suitable examples of substituents include but are not limited to: F, Cl, Br, $CF_3$, O—$C_1$-$C_6$ alkyl, $C_1$-$C_6$ alkyl, OH, $COC_1$-$C_6$ alkyl, $COOC_1$-$C_6$ alkyl.

As used herein, the term "heteroaryl" means a monocyclic- or polycyclic 5-12 membered aromatic ring comprising carbon atoms, hydrogen atoms, and one or more heteroatoms, preferably, 1 to 3 heteroatoms, independently selected from nitrogen, oxygen, and sulfur. Illustrative examples of heteroaryl groups include, but are not limited to pyridinyl, pyridazinyl, pyrimidyl, pyrazyl, triazinyl, pyrrolyl, pyrazolyl, imidazolyl, (1,2,3,)- and (1,2,4)-triazolyl, pyrazinyl, tetrazolyl, furyl, thienyl, isoxazolyl, thiazolyl, isoxazolyl, oxazolyl, indazolyl, indolyl, benzoimidazolyl, quinolyl, isoquinolinyl and the like. Preferably, heteroaryl is pyridinyl.

As used herein, the term "$C_3$-$C_{10}$ cycloalkyl" refers to a saturated or partially unsaturated, monocyclic or polycyclic hydrocarbon system comprising from 4 to carbon 10 atoms. Suitable examples of $C_3$-$C_{10}$ cycloalkyl include and are not limited to cyclopropyl, cyclobutyl, cyclpentyl, cyclohexyl or adamantyl.

As used herein, the term "$C_3$-$C_{10}$ heterocycloalkyl" refers to a nonaromatic monocyclic or polycyclic ring of 3 to 10 members, comprising carbon atoms, hydrogen atoms, and one or more heteroatoms, preferably, 1 to 3 heteroatoms, independently selected from nitrogen, oxygen, and sulfur. Suitable examples of $C_3$-$C_{10}$ heterocycloalkyl include and are not limited to pyrrolinyl, pyrrolidinyl, pyrazolinyl, piperidinyl, morpholinyl, thiomorpholinyl. Salts of the compounds of the present invention are also encompassed within the scope of the invention. Because of their potential use in medicine, the salts of the compounds of formula I are preferably pharmaceutically acceptable. Suitable pharmaceutically acceptable salts comprise conventional non-toxic salts obtained by salification of a compound of formula I with inorganic acids (e.g. hydrochloric, hydrobromic, sulphuric, or phosphoric acids), or with organic acids (e.g. acetic, propionic, succinic, benzoic, sulfanilic, 2-acetoxybenzoic, cinnamic, mandelic, salicylic, glycolic, lactic, oxalic, malic, maleic, malonic, fumaric, tartaric, citric, p-toluenesulfonic, methanesulfonic, ethanesulfonic, or naphthalensulfonic acids). For reviews on suitable pharmaceutical salts see (Berge S. M. et al., J. Pharm. Sci. 1977, 66, 1-19; Gould P. L. Int. J. Pharm 1986, 33, 201-217; Bighley et al. Encyclopedia of Pharmaceutical Technology, Marcel Dekker Inc, New York 1996, Volume 13, page 453-497; and Remington "The Science and Practice of Pharmacy", Lippincott Williams & Wilkins, 2000).

In addition, pharmaceutically acceptable base addition salts can be formed with a suitable inorganic or organic base such as triethylamine, ethanolamine, triethanolamine, dicyclohexylamine, ammonium hydroxide, pyridine. The term "inorganic base," as used herein, has its ordinary meaning as understood by one of ordinary skill in the art and broadly refers to an inorganic compound that can act as a proton acceptor. The term "organic base," as used herein, also has its ordinary meaning as understood by one of ordinary skill in the art and broadly refers to an organic compound that can act as a proton acceptor.

Other suitable pharmaceutically acceptable salts include pharmaceutically acceptable alkali-metal or alkaline-earth-metal salts such as sodium, potassium, calcium or magnesium salts; in particular pharmaceutically acceptable salts of one or more carboxylic acid moieties that may be present in the compound of formula I.

Other salts, which are not pharmaceutically acceptable, for example the trifluoroacetate salt, may be useful in the preparation of compounds of this invention and these form a further aspect of the invention. The invention includes within its scope all possible stoichiometric and nonstoichiometric forms of the salts of the compounds of formula I.

In addition, the compounds of formula I may exist in unsolvated as well as in solvated forms with pharmaceutically acceptable solvents such as water, EtOH and the like.

Certain compounds of formula I may exist in stereoisomeric forms (e.g. they may contain one or more asymmetric carbon atoms). The individual stereoisomers (enantiomers and diastereomers) and mixtures of these are included within the scope of the present invention. The present invention also covers the individual isomers of the compounds represented by formula I as mixtures with isomers thereof in which one or more chiral centers are inverted. Racemic mixtures may be separated to give their individual enantiomer using preparative HPLC using a column with chiral stationary phase or resolved to yield individual enantiomers utilizing methods known to those skilled in the art. In addition, chiral intermediate compounds may be resolved and used to prepare individual enantiomers.

The compounds of the invention or solvates/hydrates of the compounds of formula I or salts, may exist in one or more polymorphic forms. The invention extends to all such forms whether in a pure polymorphic form or when admixed with any other material, such as another polymorphic form.

The compounds of formula I may exist in zwitterionic from. Likewise, it is understood that compounds of formula I may exist in tautomeric forms other than that shown in the formula and these are also included within the scope of the present invention.

It will be appreciated by those skilled in the art that certain protected derivatives of the compounds of the invention, which may be made prior to a final deprotection stage, may not possess pharmacological activity as such, but may, in certain instances, be administered orally or parenterally and thereafter metabolized in the body to form compounds defined in the first aspect which are pharmacologically active. Such derivatives may therefore be described as "prodrugs". All protected derivatives and prodrugs of compounds defined in the first aspect are included within the scope of the invention. Examples of suitable pro-drugs for the compounds of the present invention are described in Drug of Today, Volume 19, Number 9, 1983, pp 499-538 and in Topics in Chemistry, Chapter 31, pp 306-316 and in "Design of Prodrugs" by H. Bundgaard, Elsevier, 1985, Chapter 1 (the disclosure in which document is incorporated herein by reference). It will be further appreciated by those skilled in the art that certain moieties, known to those skilled in the art as "pro-moieties", for described by H. Bundgaard, in "Design of Prodrugs" (the disclosure in which document is incorporated herein by reference) may be placed on appropriate functionalities when such functionalities are present within the compound defined in the first aspect.

The invention also includes all suitable isotopic variations of a compound of the invention. An "isotopic variation" of a compound of the invention is defined as one in which at least one atom is replaced by an atom having the same atomic number but an atomic mass different from the atomic mass usually found in nature. Examples of isotopes that can be incorporated into compounds of the invention include isotopes such as $^{2}H$, $^{3}H$, $^{13}C$, $^{14}C$, $^{15}N$, $^{17}O$, $^{18}O$, $^{31}P$, $^{32}P$, $^{35}S$, $^{18}F$ and $^{36}Cl$, respectively. Certain isotopic variations of the invention, for example, those in which a radioactive isotope such as $^{3}H$ or $^{14}C$ is incorporated, are useful in drug and/or substrate tissue distribution studies. Further, substitution with isotopes such as deuterium $^{2}H$, may afford certain therapeutic advantages resulting from greater metabolic stability. Isotopic variations of the compounds of the invention can generally be prepared by conventional procedures such as by the illustrative methods or by the preparations described in the examples hereafter using appropriate isotopic variations of suitable reagents.

Compounds of the present invention can destabilize the viral envelope. Therefore, they are suitable for the treatment of patients infected by enveloped viruses. Enveloped viruses are viruses surrounded by a phospholipid bilayer (derived from the host cell membrane), and viral glycoproteins, collectively named envelope.

Enveloped viruses according to the present invention include but are not limited to: human immunodeficiency virus, herpes virus, influenza virus, Respiratory Syncytial Virus (RSV), Cytomegalovirus (CMV), Zika Virus (ZKV), Dengue Virus, West Nile Virus, Lassa Virus, Ebola Virus, Lloviu virus, Bundibugyo virus, Reston virus, Sudan virus, Tai Forest virus, Marburg virus, Ravn virus (RAVV), Pneumovirus, Junin Virus, Rift Valley fever virus, La Crosse Virus, Porcine Reproductive And Respiratory Syndrome Virus, Poxvirus, Bovine Viral Diarrhea Norovirus, SARS Coronavirus, Chikunguya Virus, Hepatitis C Virus, Hepatitis B Virus, Schmallenberg virus, African swine fever virus, Eastern Equine Encephalitis Virus, Cowpox virus, Western Equine Encephalitis Virus, Nipah Virus, Omsk hemorrhagic fever Virus, Venezuelan Equine Encephalitis Virus, Human parainfluenza viruses, Japanese Encephalitis Virus, Tick Borne Encephalitis Virus, Russian spring-summer encephalitis (RSSE) virus, Yellow Fever Virus, Newcastle Virus, Virus (BVDV), Parainfluenza virus type 5 (PIV5), Border Disease Virus (BDV) of sheep, Classical Swine Fever Virus (CSFV), Vesicular Stomatitis Virus (VSV) and HSV-2 acyclovir resistant (HSV-2 Acy R).

Preferred enveloped viruses according to the present invention include: human immunodeficiency virus, herpes virus, cytomegalovirus, Respiratory Syncytial Virus, Vesicular Stomatitis Virus, influenza virus, dengue virus and zika virus.

Preferably, said human immunodeficiency virus is Human Immunodeficiency Virus 1 (HIV-1) or Human Immunodeficiency Virus 2 (HIV-2).

Preferably, said herpes virus is Herpes 1 virus (HSV-1) or Herpes 2 virus (HSV-2).

Preferably, said influenza virus is H1N1, H3N2, H7N9, BB, BP.

Preferably, said cytomegalovirus is human cytomegalovirus (HCMV).

Preferably, said dengue virus in DENV-2 or DENV-1.

The compounds of the present invention are particularly suitable for the treatment of patients infected by enveloped viruses, preferably Herpes virus, said virus being resistant to at least one currently used anti-viral treatment. For instance, patients resistant to acyclovir, raltegravir, ribavirine and sofosbuvir.

In the present invention the compounds as defined above and suitable excipients or diluents may be administered in combination with approved drugs for the treatment of viral infections, preferably HIV-1 infections, as part of the highly active antiretroviral therapy (HAART).

Examples of compounds that may be administered in combination with the compounds of the present invention include but are not limited to: acyclovir; ribavirine; a nucleoside analogue such as Zidovudine, Didanosine, Lamivudine, Emtricitabine; a non-nucleoside analogue reverse-transcriptase inhibitor such as Efavirenz, Nevirapine, Etravirine, Rilpivirine; a nucleotide analogue reverse-transcriptase inhibitor such as Tenofovir; an integrase inhibitor such as Raltegravir; a NS3/4A serine protease inhibitor such as Boceprevir, Telaprevir; a NS5B polymerase inhibitor such as Dasabuvir, Sofosbuvir, interferon alpha, Maraviroc, Highly active antiretroviral therapy (HAART), Enfuvirtide, Entecavir, Lamivudine, Brivudin, Famiciclovir, Penciclovir, Ganciclovir, Amantadine, Rimantadine, Oseltamivir, Zanamivir.

As used herein, the term "nucleoside analogue reverse-transcriptase inhibitor" refers to a class of compounds nucleoside analogues able to block reverse transcriptase enzyme of HIV. Suitable examples of nucleoside analogue reverse transcriptase inhibitors include but are not limited to stavudine, zidovudine and lamivudine.

As used herein, the term "non-nucleoside analogue reverse-transcriptase inhibitor" refers to a class of compounds with chemical structures unrelated to nucleosides, able to block the reverse transcriptase enzyme of HIV. Suitable examples of non-nucleoside analogue reverse transcriptase inhibitor include but are not limited to Efavirenz, Etravirine, Nevirapine and Rilpivirine.

As used herein, the term "nucleotide analogue reverse-transcriptase inhibitor" refers to a class of compounds nucleotide analogues able to block reverse transcriptase enzyme of HIV. Suitable examples of nucleotide analogue reverse-transcriptase inhibitor include but are not limited to tenofovir.

As used herein, the term "integrase inhibitor" refers to a class of compounds able to block integrase enzyme of HIV. Suitable examples of integrase inhibitor include but are not limited to raltegravir, dolutegravir and elvitegravir.

As used herein, the term "NS3/4A serine protease inhibitor" refers to a class of compounds able to block NS3/4A serine protease enzyme of HCV. Suitable examples of NS3/4A serine protease inhibitor include but are not limited to telaprevir, boceprevir and paritaprevir.

As used herein, the term "NS5B polymerase inhibitor" refers to a class of compounds able to block NS5B polymerase enzyme of HCV. Suitable examples of NS5B polymerase inhibitor include but are not limited to ledipasvir, ombitasvir and sofosbuvir As used herein, the term "highly active antiretroviral therapy" refers to a therapy which combines three or more drugs able to interfere in different points of HIV replication. Suitable examples of highly active antiretroviral therapy include but are not limited to Triumeq, Trizivir, Stribild.

Preferably the pharmaceutical composition comprising at least one or two of the compounds of the invention together with at least one approved compound for the treatment of viral infections are in the same formulation or a pharmaceutically acceptable salt thereof, and suitable excipients and/or diluents to be administered as such.

In the present invention the compounds of the invention or their salts may be administered as pure or as pharmaceutical formulations, i.e. suitable for parenteral, oral, vaginal, or rectal administrations. Each of said formulations may contain excipients and/or fillers and/or additives and/or binders, coatings and/or suspending agents and/or emulsifying agents, preserving and/or control release agents suitable for the selected pharmaceutical form.

It is a further object of the invention a method for treating a viral disease in a cell, comprising contacting the cell with the compound or the composition of the invention.

The invention also provides pharmaceutical compositions comprising at least one compound of this invention or a pharmaceutical acceptable salt or solvate thereof and one or more pharmaceutically acceptable carriers, excipients and/or diluents.

The pharmaceutical compositions can be chosen based on the treatment requirements. Such compositions are prepared by blending and are suitably adapted to oral or parenteral administration, and as such can be administered in the form of tablets, capsules, oral preparations, powders, granules, pills, injectable or infusible liquid solutions, suspensions, suppositories, preparation for inhalation. Tablets and capsules for oral administration are normally presented in unit dose form and contain conventional excipients such as binders, fillers (including cellulose, mannitol, lactose), diluents, tableting agents, lubricants (including magnesium stearate), detergents, disintegrants (e.g. polyvinylpyrrolidone and starch derivatives such as sodium glycolate starch), coloring agents, flavoring agents, and wetting agents (for example sodium lauryl sulfate).

The oral solid compositions can be prepared by conventional methods of blending, filling or tableting. The blending operation can be repeated to distribute the active principle throughout compositions containing large quantities of fillers. Such operations are conventional. Oral liquid preparations can be in the form of, for example, aqueous or oily suspensions, solutions, emulsions, syrups or elixirs, or can be presented as a dry product for reconstitution with water or with a suitable vehicle before use. Such liquid preparations can contain conventional additives such as suspending agents, for example sorbitol, syrup, methyl cellulose, gelatine, hydroxyethyl cellulose, carboxymethyl cellulose, aluminium stearate gel, or hydrogenated edible fats; emulsifying agents, such as lecithin, sorbitan monooleate, or acacia; non-aqueous vehicles (which can include edible oils), such as almond oil, fractionated coconut oil, oily esters such as esters of glycerine, propylene glycol, or ethyl alcohol; preservatives, such as methyl or propyl p-hydroxybenzoate or sorbic acid, and if desired, conventional flavouring or colouring agents. Oral formulations also include conventional slow-release formulations such as enterically coated tablets or granules.

Pharmaceutical preparation for administration by inhalation can be delivered from an insufflator or a nebulizer pressurized pack.

For parenteral administration fluid unit dosages can be prepared, containing the compound and a sterile vehicle. The compound can be either suspended or dissolved, depending on the vehicle and concentration. The parenteral solutions are normally prepared by dissolving the compound in a vehicle, sterilising by filtration, filling suitable vials and sealing. Advantageously, adjuvants such as local anaesthetics, preservatives and buffering agents can also be dissolved in the vehicle. To increase the stability, the composition can be frozen after having filled the vials and removed the water under vacuum. Parenteral suspensions are prepared in substantially the same manner, except that the compound can be suspended in the vehicle instead of being dissolved and sterilized by exposure to ethylene oxide before suspending in the sterile vehicle. Advantageously, a surfactant or wetting agent can be included in the composition to facilitate uniform distribution of the compound of the invention.

In order to increase bioavailability, the compounds can be pharmaceutically formulated in liposomes or in nanoparticles. Acceptable liposomes can be neutral, negatively, or positively charged, the charge being a function of the charge of the liposome components and pH of the liposome solution. Liposomes can be normally prepared using a mixture of Phospholipids and cholesterol. Suitable phospholipids include phosphatidylcholine, phosphatidylethanolamine, phosphatidic acid, phosphotidylglycerol, phosphatidylinositol. Polyethylene glycol can be added to improve the blood circulation time of liposomes. Acceptable nanoparticles include albumin nanoparticles and gold nanoparticles.

For buccal or sublingual administration, the compositions may be tablets, lozenges, pastilles, or gel.

The compounds can be pharmaceutically formulated as suppositories or retention enemas, e.g. containing conventional suppositories bases such as cocoa butter, polyethylene glycol, or other glycerides, for a rectal administration.

Another means of administering the compounds of the invention regards topical treatment. Topical formulations can contain for example ointments, creams, lotions, gels, solutions, pastes and/or can contain liposomes, micelles and/or microspheres. Examples of ointments include oleaginous ointments such as vegetable oils, animal fats, semisolid hydrocarbons, emulsifiable ointments such as hydroxystearin sulfate, anhydrous lanolin, hydrophilic petrolatum, cetyl alcohol, glycerol monostearate, stearic acid, water soluble ointments containing polyethylene glycols of various molecular weights. Creams, as known to formulation experts, are viscous liquids or semisolid emulsions, and contain an oil phase, an emulsifier and an aqueous phase. The oil phase generally contains petrolatum and an alcohol such as cetyl or stearic alcohol. Formulations suitable for topical administration to the eye also include eye drops, wherein the active ingredient is dissolved or suspended in a suitable carrier, especially an aqueous solvent for the active ingredient.

A further method of administering the compounds of the invention regards transdermal delivery. Topical transdermal formulations comprise conventional aqueous and non-aqueous vectors, such as creams, oils, lotions or pastes or can be in the form of membranes or medicated patches.

Formulations are known in the art (Remington Remington "The Science and Practice of Pharmacy", Lippincott Williams & Wilkins, 2000).

The compounds of the present invention may be employed for use in the treatment and/or prevention of the above-mentioned conditions alone as a sole therapy or in combination with other therapeutic agents either by separate administrations, or by including the two or more active principles in the same pharmaceutical formulation. The compounds may be administered simultaneously or sequentially.

The other therapeutic agents may be any antiviral drugs or approved drugs for the treatment of viral infections, for instance, in HIV-1 infections as part of the highly active antiretroviral therapy (HAART). Non-exhaustive examples of suitable additional agents include in particular drugs belonging to the group of: a nucleoside or a non-nucleoside analogue reverse-transcriptase inhibitor, a nucleotide analogue reverse-transcriptase inhibitor.

The combination can be administered as separate compositions (simultaneous, sequential) of the individual components of the treatment or as a single dosage form containing all agents. When the compounds of this invention are in combination with other active ingredients, the active ingredients may be separately formulated into single-ingredient preparations of one of the above-described forms and then provided as combined preparations, which are given at the same time or different times or may be formulated together into a two- or more ingredients preparation.

Compounds of general formula I may be administered to a patient in a total daily dose of, for example, from 0.001 to 1000 mg/kg body weight daily. Dosage unit compositions may contain such amounts of submultiples thereof to make up the daily dose. The compound may also be administered weekly or any other day. The determination of optimum dosages for a particular patient is well known to one skilled in the art. As is common practice, the compositions are normally accompanied by written or printed instructions for use in the treatment in question.

Compounds of the invention may be prepared in a variety of ways. These processes form further aspects of the invention.

The invention will be now illustrated by means of non-limiting examples with reference to the following figures.

DETAILED DESCRIPTION OF THE INVENTION

Synthesis

General

Figure 1:
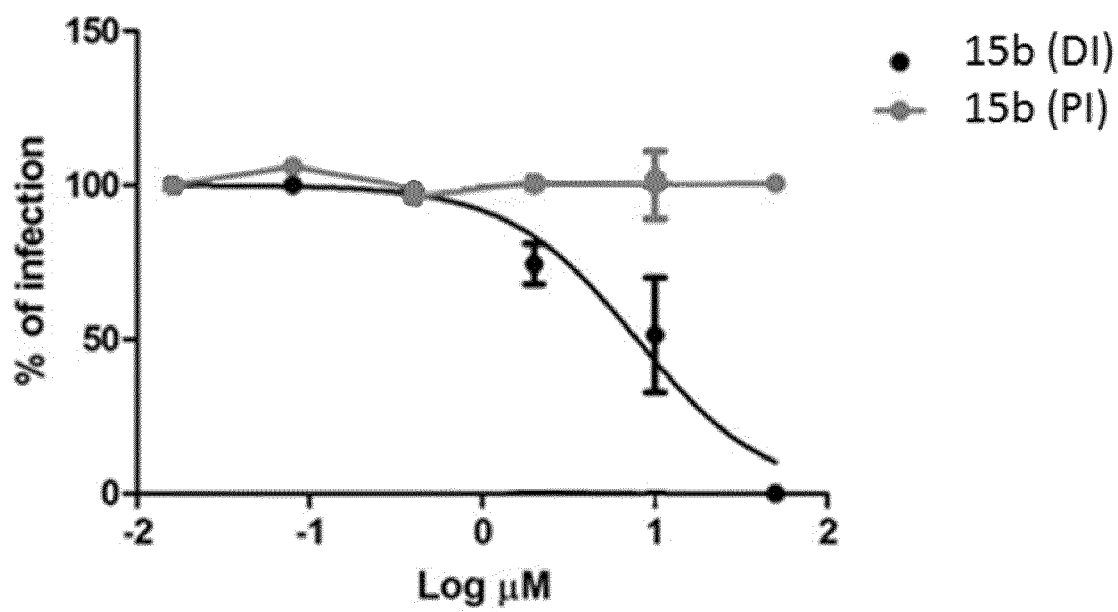
FIG. 1: Pretreatment (PI) and during infection with HSV-2 (DI) assays in vero cells. The antiviral activity of the compound is not due to an interaction with the host cells, since compound 15b is inactive in pre-treatment assays while there was a significant reduction of antiviral activity in the (DI) assay (15b EC50 7.89 µM).

Reagents were obtained from commercial suppliers (for example Sigma-Aldrich). All commercially available chemicals were used as purchased without further purification. $CH_3CN$ was dried over calcium hydride, $CH_2Cl_2$ was dried over calcium hydride and THF was dried over Na/benzophenone prior to use while DMF was bought already anhydrous. Anhydrous reactions were run under a positive pressure of dry $N_2$ or argon. TLC was carried out using Merck TLC plates silica gel 60 F254. Chromatographic purifications were performed on columns packed with Merk 60 silica gel, 23-400 mesh, for flash technique. $^1$H-NMR and $^{13}$C-NMR spectra were recorded at 400 MHz on a Brucker Avance DPX400 spectrometer. Chemical shifts are reported relative to tetramethylsilane at 0.00 ppm. $^1$H patterns are described using the following abbreviations: s=singlet, d=doublet, t=triplet, q=quartet, quint=quintet, sx=sextet, sept=septet, m=multiplet, br=broad signal, br s=broad singlet. Mass spectra (MS) data were obtained using an Agilent 1100 LC/MSD VL system (G1946C) with a 0.4 mL/min flow rate using a binary solvent system 25 of 95:5 methyl alcohol/water. UV detection was monitored at 254 nm. Mass spectra were acquired in positive and negative mode scanning over the mass range.

Microwave Irradiation Experiments Microwave irradiation experiments were conducted using CEM Discover Synthesis Unit (CEM Corp., Matthews, NC). The machine consists of a continuous focused microwave power delivery system with operator selectable power output from 0 to 300 W. The temperature of the contents vessels was monitored using calibrate infrared temperature control mounted under the reaction vessel. All the experiments were performed using a stirring option whereby the contents of the vessels are stirred by means of rotating magnetic plate located below the floor of the microwave cavity and a Teflon-coated magnetic stir bar in the vessel.

In the present invention the following abbreviations are used:

| | |
|---|---|
| NMR (Nuclear Magnetic Resonance) | $^1$H (proton) |
| MHz (Megahertz) | $^{13}$C (carbon) |
| $^{19}$F (fluorine) | LC-MS (Liquid Chromatography Mass Spectrum) |
| Hz (Hertz) | HPLC (High Performance Liquid Chromatography) |
| s (seconds) | min (minutes) |
| h (hour(s)) | mg (milligrams) |
| g (grams) | µL (microlitres) |
| mL (millilitres) | mmol (millimoles) |
| nm (nanometers) | µM (micromolar) |
| M (molarity) | SI selectity index |
| DMEM (Dulbecco's Modified Eagle's Medium) | o.n. (overnight) |
| BOC or boc (tert-butyloxycarbonyl) | DMF (dimethylformamide) |
| DCM (dichloromethane) | ACN (acetonitrile) |
| Pyr Pyridine | RT or rt or r.t. (room temperature) |

-continued

| | |
|---|---|
| DMF (dimethylformamide) | DMSO (dimethyl sulfoxide) |
| DMSO d-$_6$ (deuterated dimethyl sulfoxide) | MeOH (methanol) |
| MeOD-d$_4$ (deuterated methanol) | CDCl$_3$-d (deuterated chloroform) |
| Et$_2$O (diethyl ether) | EtOAc or EA (ethyl acetate) |
| EtOH (ethanol) | AcOH (acetic acid) |
| iPrOH (isopropanol) | D$_2$O (deuterated water) |
| TEA (triethylamine) | THF (tetrahydrofuran) |
| PE (petroleum ether) | t-Bu (tert-butyl) |
| t$_R$ (retention time) | Cmpd. (compound) |
| wt wild type | MTBE (methyl tert-butyl ether) |
| MDA malondialdehyde | TBA 2-thiobarbituric acid |
| IF immunofluorescence | |

Except where indicated otherwise, all temperatures are expressed in ° C. (degrees centigrade) or K (Kelvin).

The yields were calculated assuming that products were 100% pure if not stated otherwise.

Example 1

Scheme 1. Synthesis of substitutted aldheydes 3a-g and 4a-b

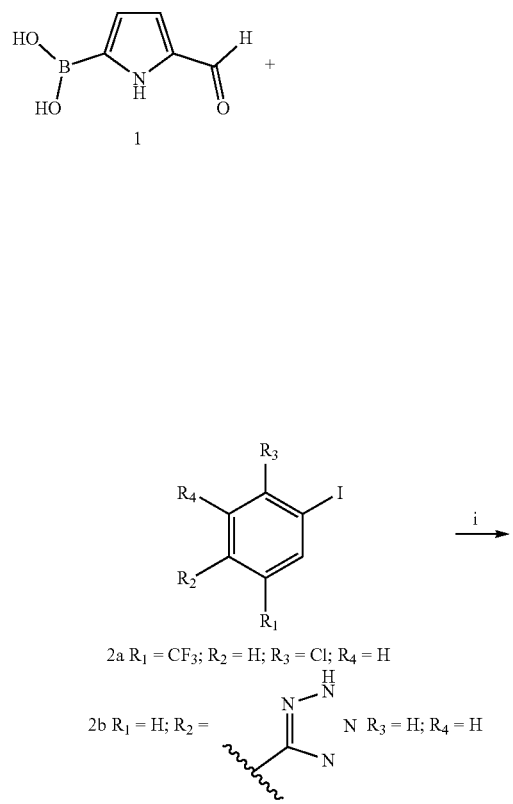

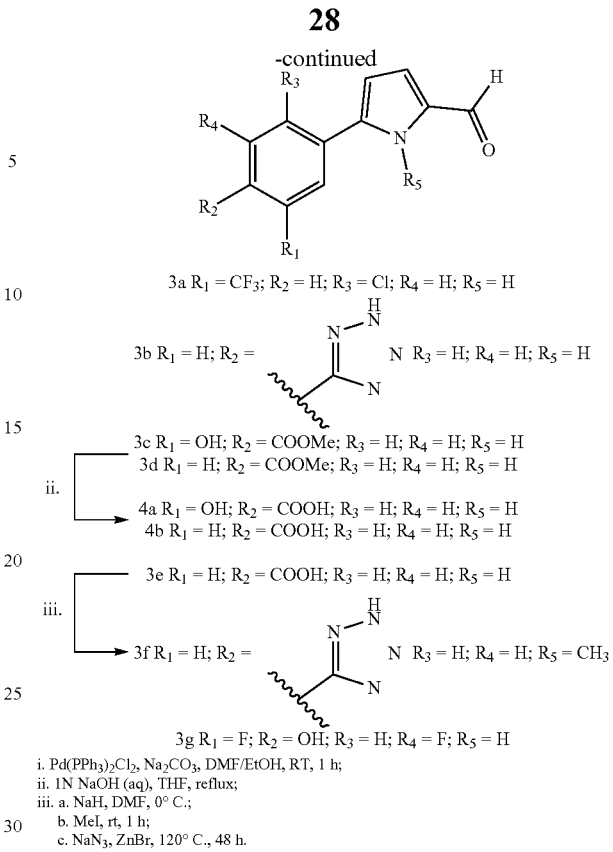

i. Pd(PPh$_3$)$_2$Cl$_2$, Na$_2$CO$_3$, DMF/EtOH, RT, 1 h;
ii. 1N NaOH (aq), THF, reflux;
iii. a. NaH, DMF, 0° C.;
    b. MeI, rt, 1 h;
    c. NaN$_3$, ZnBr, 120° C., 48 h.

General Procedure for the Synthesis of Aldehydes 3a-e and 3g:

The opportune iodo derivative (2a-g, 1.00 mmol) and 5-formyl-2-pyrrol boronic acid (1, 1.1 mmol) were dissolved in 10 mL of DMF and 15 ml of EtOH. The reaction mixture was stirred for 10 minutes under N$_2$, then Pd(PPh$_3$)$_2$Cl$_2$ (0.10 mmol) and Na$_2$CO$_3$ 2M (6.00 mmol) were added. The reaction mixture (light-orange) was stirred under N$_2$ at room temperature. After 1 h, the reaction went to completion (monitoring with TLC) and was quenched with H$_2$O and 2N HCl, then EtOAc was added, and the mixture was stirred until the two layers became clear. The aqueous layer was extracted three times with EtOAc, then the organic phase was washed several times with H$_2$O and brine, dried over Na$_2$SO$_4$, filtered and evaporated under reduced pressure. Final aldehydes 3a-e and 3g were purified by flash chromatography using the opportune eluent. The iodo derivative 2a was purchased from Sigma Aldrich (catalogue number 304344), compound 2b was prepared according to the procedure described in Example 7, compound 2c was purchased from Enamine (catalogue number BBV-40201642), compound 2d was purchased from Sigma Aldrich (catalogue number 679100), compound 2e was purchased from Sigma Aldrich (catalogue number 579157), compound 2g was purchased from Enamine (catalogue number BBV-40201423).

5-(2-chloro-5-(trifluoromethyl)phenyl)-1H-pyrrol-2-carbaldehyde (3a)

(Purification eluent: PE/AcOEt 4:1) pale red solid. (yield 30%); $^1$H NMR: (400 MHz CD$_3$Cl$_3$) δ (ppm) 10.86 (bs, 1H), 9.53 (s, 1H), 7.96 (s, 1H), 7.58 (d, 1H, J=8.4 Hz), 7.51 (d, 1H, J=8.4 Hz), 7.06 (s, 1H), 6.82 (s, 1H); MS: (ESI) m/z 273.8 [M+H]$^+$ 295.8 [M+Na]$^+$ 271.9 [M−H]$^−$

5-(4-(1H-tetrazol-5-yl)phenyl)-1H-pyrrole-2-carbaldehyde (3b)

Compound 1 (0.16 mmol, 1 eq) and compound 2b (0.21 mmol, 1.30 eq) were dissolved in a mixture of DMF/EtOH 1:2 (3 ml) and stirred under $N_2$ atmosphere for 10 min. Then $Pd(PPh_3)_2Cl_2$ (0.016 mmol, 0.10 eq), and $Na_2CO_3$ 2M (0.96 mmol, 6 eq) were added. The reaction mixture was stirred at 70° C. for 1 h. The reaction mixture was concentrated under reduced pressure, then acidified with HCl 3N until pH≈2 and extracted with EtOAc. Dried over $Na_2SO_4$ and concentrated. The crude product was purified by flash chromatography in DCM/MeOH 95:5 providing compound 3b as a beige solid. Yield: 30%. $^1$H NMR: (400 MHz (MeOD) δ (ppm) 9.42 (s, 1H), 8.07 (d, 2H, J=8 Hz), 7.80 (d, 2H, J=8 Hz), 7.03 (d, 1H, J=11.6 Hz), 6.70 (d, 2H, J=11.6 Hz).

methyl 4-(5-formyl-1H-pyrrol-2-yl)-2-hydroxybenzoate (3c)

(Purification eluent: PE/AcOEt 4:1) pale brown solid (Yield 50%). $^1$H NMR: (400 MHz CDCl$_3$) δ (ppm) 10.84 (s, 1H), 9.71 (bs, 1H), 9.55 (s, 1H), 7.88 (d, 1H, J=8.4 Hz), 7.22 (s, 1H), 7.12 (d, 1H, J=8.0 Hz), 7.02 (s, 1H), 6.72 (s, 1H), 3.97 (s, 3H); MS: (ESI) m/z 245.9 [M+H]$^+$

Methyl 4-(5-formyl-1H-pyrrol-2-yl)benzoate (3d)

(Purification eluent: PE/AcOEt 4:1) beige solid (Yield 51%). $^1$H NMR: (400 MHz (CDCl$_3$) δ (ppm) 9.83 (bs, 1H), 9.54 (s, 1H), 8.08-8.05 (d, 2H, J=8.4 Hz), 7.67-7.65 (d, 2H, J=8.4 Hz), 7.02-7.00 (m, 1H), 6.71-6.70 (m 1H), 3.90 (s, 3H). MS: (ESI) m/z 227.8 [M–H]$^-$

4-(5-formyl-1H-pyrrol-2-yl)benzonitrile (3e)

(Purification eluent: PE/AcOEt 4:1) pale yellow solid (Yield 50%). H NMR: (400 MHz (CDCl$_3$) δ (ppm) 10.44 (bs, 1H), 9.54 (s, 1H), 7.78-7.76 (d, 2H, J=8 Hz), 7.69-7.67 ((d, 2H, J=8 Hz), 7.05-7.04 (m, 1H), 6.72-6.71 (m, 1H). MS: (ESI) m/z 194.9 [M–H]$^-$

5-(3,5-difluoro-4-hydroxyphenyl)-1H-pyrrole-2-carbaldehyde (3g)

(Purification eluent: DCM/MeOH 95:5) 62% yield. H$^1$-NMR: (400 MHz, MeOD) δ (ppm) 9.42 (s, 1H), 7.57-7.56 (d, J=4.4 Hz, 2H), 7.36-7.35 (d, J=4.0 Hz, 1H), 6.63-6.62 (d, J=4.0 Hz, 1H). MS: (ESI) m/z 221.9 [M–H]$^-$.

Procedure for the Synthesis of Aldehyde 3f

4-(5-formyl-1-methyl-1H-pyrrol-2-yl)benzonitrile

To a solution of compound 3e (2.11 mmol, 1 eq) in dry DMF (10 ml) at 0° C., NaH (4.22 mmol, 2.0 eq) was added and stirred at 0° C. for 20', then methyl iodide (2.53 mmol, 1.2 eq) was added and the reaction mixture stirred at room temperature for 1 h. The reaction mixture was diluted with H$_2$O and extracted with DCM three times. The organic layer was washed several times with LiCl. Dried over Na$_2$SO$_4$ and concentrated. Flash chromatography in PE/EtOAc 7:3 afforded 4-(5-formyl-1-methyl-1H-pyrrol-2-yl)benzonitrile as yellow solid in 94% of yield. $^1$H-NMR (400 MHz, CDCl$_3$): δ (ppm) 9.62 (s, 1H), 7.75-7.73 (d, 2H, J=6.4 Hz), 7.54-7.53 (d, 2H, J=6.8 Hz), 6.99-6.98 (m, 1H), 6.37-6.36 (m, 1H), 3.94 (s, 3H).

5-(4-(1H-tetrazol-5-yl)phenyl)-1-methyl-1H-pyrrole-2-carbaldehyde (3f)

To a solution of 4-(5-formyl-1-methyl-1H-pyrrol-2-yl) benzonitrile (1.92 mmol, 1 eq) in iPrOH/H$_2$O 1:2 (20 mL), sodium azide (4.8 mmol, 2.5 eq) and zinc bromide (1.92 mmol, 1 eq) were added and the reaction mixture stirred at 120° C. for 48 h. The reaction mixture was concentrated under reduced pressure and then extracted with EtOAc and washed with H$_2$O. The organic layer was dried under Na$_2$SO$_4$ and concentrated. The residue was crystallized from Ethanol as white solid. Yield 75%. $^1$H-NMR (400 MHz, CD$_3$OD): δ (ppm) 9.54 (s, 1H), 8.15-8.13 (d, 2H, J=8 Hz), 7.72-7.70 (d, 2H, J=8 Hz), 7.11-7.10 (m, 1H), 6.46-6.45 (m, 1H), 3.96 (s, 3H). MS: (ESI) m/z 252.0 [M–H]$^-$.

General Procedure for the Synthesis of Aldehydes 4a, 4b:

Compound 3c or 3d was dissolved in 25 mL of THF, then a solution of NaOH 1M (5.00 mmol) was added dropwise, after the reaction mixture was heated at reflux. The reaction mixture was stirred for 5 h until completion (TLC). Organic solvent was removed under reduced pressure, then some water was added, and the aqueous layer was extracted three times with Et$_2$O; the aqueous layer was then acidified to pH 1 with HCl 6N and extracted with EtOAc (3×10 mL), washed with Brine and dried over Na$_2$SO$_4$. 4a and 4b were obtained as pale brown solids and used for the next step without further purification.

4-(5-Formyl-1H-pyrrol-2-yl)-2-hydroxybenzoic Acid (4a)

Yield 98% $^1$H NMR: (400 MHz (CD$_3$)$_2$SO) δ (ppm) 9.52 (s, 1H), 7.78 (d, 1H, J=8 Hz), 7.51 (s, 1H), 7.43 (d, 1H, J=8.4 Hz), 7.05 (d, 1H, J=2.4 Hz), 6.90 (d, 1H, J=6 Hz); MS: (ESI) m/z 229.9 [M–H]$^-$.

4-(5-formyl-1H-pyrrol-2-yl)benzoic Acid (4b)

Yield: 88%. $^1$H NMR: (400 MHz (MeOD) δ (ppm) 9.46 (s, 1H), 8.05-8.03 (m, 2H), 7.84-7.82 (m, 2H), 7.08-7.07 (m, 1H), 6.80-6.78 (m, 1H).

Example 2

Scheme 2. Synthesis of substituted rhodanine derivatives 7 a-b

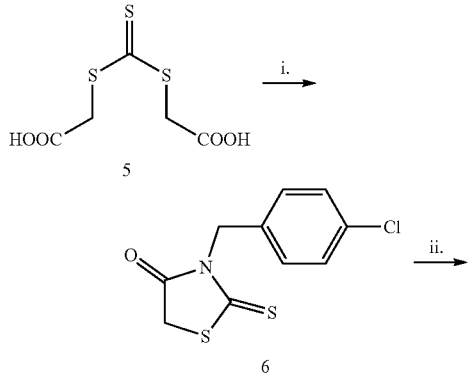

-continued

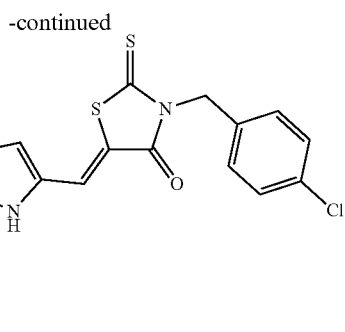

7a R$_1$ = CF$_3$; R$_2$ = H; R$_3$ = Cl
7b R$_1$ = OH; R$_2$ = COOH; R$_3$ = H i. 4-chlorobenzylamine, DME, Et$_3$N, MW (300 W), 90° C., 10 min.
ii. Opportune aldehyde, β-alanine CH$_3$COOH, reflux, 5 min.

3-(4-chlorobenzyl)-2-thioxothiazolidin-4-one (6)

Bis(carboxymethyl)trithiocarbonate 5 (0.88 mmol, 1 eq purchased from Sigma Aldrich 173029-25G) was solubilized in 3 mL of DME. To this, TEA (0.88 mmol, 1 eq) and 4-chlorobenzylamine (0.88 mmol, 1 eq) were added, and the mixture was microwave-irradiated at 90° C. for 10 minutes. The solvent was removed at reduced pressure to furnish a residue that was then solubilized in 3 mL of CH$_3$OH. 5 mL of 2N HCl were added drop by drop. The suspension was diluted with water and extracted with AcOEt (3×25 mL). The organic layers were dried over Na$_2$SO$_4$ and filtered-off. The solvent was removed at reduced pressure to furnish compound 6 as orange oil that was used for the next step without further purification. Yield 72%. $^1$H NMR: (400 MHz CD$_3$OD) δ (ppm) 7.35 (d, 2H, J=8.8 Hz), 7.27 (d, 2H, J=8.8 Hz), 5.11 (s, 2H), 4.12 (s, 2H); MS: (ESI) m/z 255.9 [M−H]$^−$
General Procedure for the Synthesis of Final Compounds 7a-b:

Compound 6 (0.46 mmol, 2 eq) and the opportune aldehyde 3a or 4a (0.23 mmol, 1 eq) were solubilised in 3 mL of glacial CH$_3$COOH. To this β-alanine (0.46 mmol, 2 eq) was added in one portion and the mixture was stirred at reflux for further 5 hours. After this time H$_2$O was added, the resulting precipitate was filtered-off at reduced pressure and washed with Et$_2$O. The residue was purified by flash chromatography

(Z)-5-((5-(2-chloro-5-(trifluoromethyl)phenyl)-1H-pyrrol-2-yl)methylene)-3-(4-chlorobenzyl)-2-thioxothiazolidin-4-one (7a)

Red solid, yield 20% (Eluent: PE/AcOEt 24:1). $^1$H NMR: (400 MHz CD$_3$Cl$_3$) δ (ppm) 7.90 (s, 1H), 7.64 (d, 1H, J=8.4 Hz), 7.53 (d, 1H, J=8.0 Hz), 7.61 (d, 1H, J=8.0 Hz), 7.39 (d, 1H, J=8.4 Hz), 7.28 (d, 1H, J=8.0 Hz), 6.95 (s, 1H), 6.85 (s, 1H), 6.79 (s, 1H), 5.32 (s, 2H); $^{13}$C NMR: (101 MHz (CD$_3$)$_2$SO) δ (ppm) 193.26, 167.21, 166.44, 134.49, 132.68, 130.63, 130.26, 130.12, 129.98, 128.95, 127.41, 127.10, 126.63, 126.36, 125.99, 123.22, 123.03, 116.44, 115.26, 48.96. MS: (ESI) m/z 510.7 [M−H]$^−$

(Z)-4-(5-((3-(4-chlorobenzyl)-4-oxo-2-thioxothiazolidin-5-ylidene)methyl)-1H-pyrrol-2-yl)-2-hydroxybenzoic Acid (7b)

yield 71%, red solid (Eluent: CH$_2$Cl$_2$/CH$_3$OH 9:1). $^1$H NMR: (400 MHz (CD$_3$)$_2$SO) δ (ppm) 7.66 (d, 1H, J=8.0 Hz), 7.55 (bs, 1H), 7.37 (d, 2H, J=8.4 Hz), 7.31 (d, 2H, J=8.4 Hz), 7.13 (s, 1H), 7.10 (d, 1H, J=8.0 Hz), 6.79 (bs, 1H), 6.72 (d, 1H, J=4.0 Hz), 5.49 (bs, 1H), 5.18 (s, 2H); $^{13}$C NMR: (101 MHz (CD$_3$)$_2$SO) δ (ppm) 180.96, 177.05, 171.21, 168.10, 139.99, 137.15, 135.41, 134.70, 133.56, 118.48, 117.96, 116.88, 51.14. MS: (ESI) m/z 468.7 [M−H]$^−$ Example 3

Scheme 3. Synthesis of intermediate 1

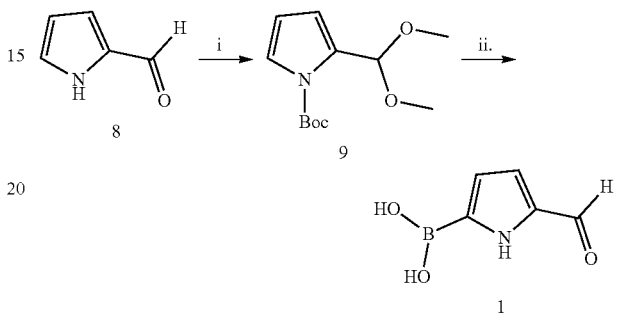

i. a) Di-tert-butyl dicarbonate, DIMAP, CH$_3$CN, rt,
  b) trimethyl orthoformate, p-toluensolfonic acid MeOH, rt, 2 h;
ii. a) B(Oi-Pr)$_3$, LDA, THF, -78° C. → rt 1 h;
  b) NH$_4$Cl, KHSO$_4$, rt, 2 h.

tert-butyl 2-formyl-1H-pyrrole-1-carboxylate: Compound 8 (10.51 mmol, 1 eq purchased from Sigma Aldrich, catalogue number P73404) was solubilized in CH$_3$CN (10 mL). To this di-tert-butyl dicarbonate (11.56 mmol, 1.1 eq) and dimethylaminopyridine (0.11 mmol, 0.01 eq) were added, and the mixture was stirred overnight at room temperature. After this time the solvent was removed at reduced pressure and water was added. The mixture was extracted several times with EtOAc (3×25 mL), the organic layers were collected and washed with Brine and dried over Na$_2$SO$_4$. The solvent was removed at reduced pressure to furnish desired compound as brown oil that was used for the next step without any purification. Yield 99%. $^1$H NMR: (400 MHz CDCl$_3$) δ (ppm) 10.23 (s, 1H), 7.35 (d, 1H, J=4.4 Hz), 7.08 (d, 1H, J=4.8 Hz), 6.19 (t, 1H, J=6.8 Hz), 1.56 (s, 9H).

tert-butyl 2-(dimethoxymethyl)-1H-pyrrole-1-carboxylate (9)

tert-butyl 2-formyl-1H-pyrrole-1-carboxylate (2.35 mmol, 1 eq) was solubilized in CH$_3$OH (3 mL). To this trimethylorthoformate (4.70 mmol, 2 eq) and p-toluensolfonic acid (0.05 mmol, 0.02 eq) were added. The mixture was stirred at room temperature for 2 hours, after this time NaHCO$_3$ (5 mL) and H$_2$O (5 mL) were added and the mixture was extracted several times with AcOEt (3×10 mL). The organic layers were collected and washed with Brine (30 mL), dried over Na$_2$SO$_4$ and filtered. The solvent was removed at reduced pressure to furnish 9 as brown oil that was used in the next step without further purification. Yield 99%. $^1$H NMR: (400 MHz CD$_3$OD) δ (ppm) 7.23 (d, 1H, J=5.2 Hz), 7.42 (s, 1H), 6.09 (t, 1H, J=6.4 Hz), 5.87 (s, 1H), 3.27 (s, 6H), 1.56 (s, 9H). MS: (ESI) m/z 263.9 [M+Na]$^+$

(5-formyl-1H-pyrrol-2-yl)boronic Acid (1)

Compound 9 (10.12 mmol, 1 eq) was solubilized in anhydrous THF (15 mL). To this a 2M solution of lithium diisopropilamide in heptane was added dropwise, (30.37 mmol, 3 eq). The reaction mixture was stirred at −78° C. for 1 h under Argon atmosphere. Then triisopropylborate (17.21 mmol, 1.7 eq) was added ant the mixture was stirred at rt for further 2 h. After this time an aqueous saturated solution of NH$_4$Cl (40 mL) and 10% KHSO$_4$ (aq) (110 mL) were consequently added, the mixture was acidified at pH≈2, and stirred for 2 h at room temperature. The mixture was extracted with AcOEt (3×25 mL), the organic layers were washed with Brine (30 mL), dried over Na$_2$SO$_4$ and filtered. The solvent was removed at reduced pressure and the residue was suspended in a 1:1 mixture of diisopropylether/hexane at 0° C. for 1 h. The residue was collected as black solid and used without further purifications. Yield 85%. $^1$H NMR: (400 MHz CD$_3$OD) δ (ppm) 9.43 (s, 1H), 6.93 (s, 1H), 6.71 (s, 1H). MS: (ESI) m/z 139.9 [M+H]$^+$ 161.9 [M+Na]$^+$ Example 4

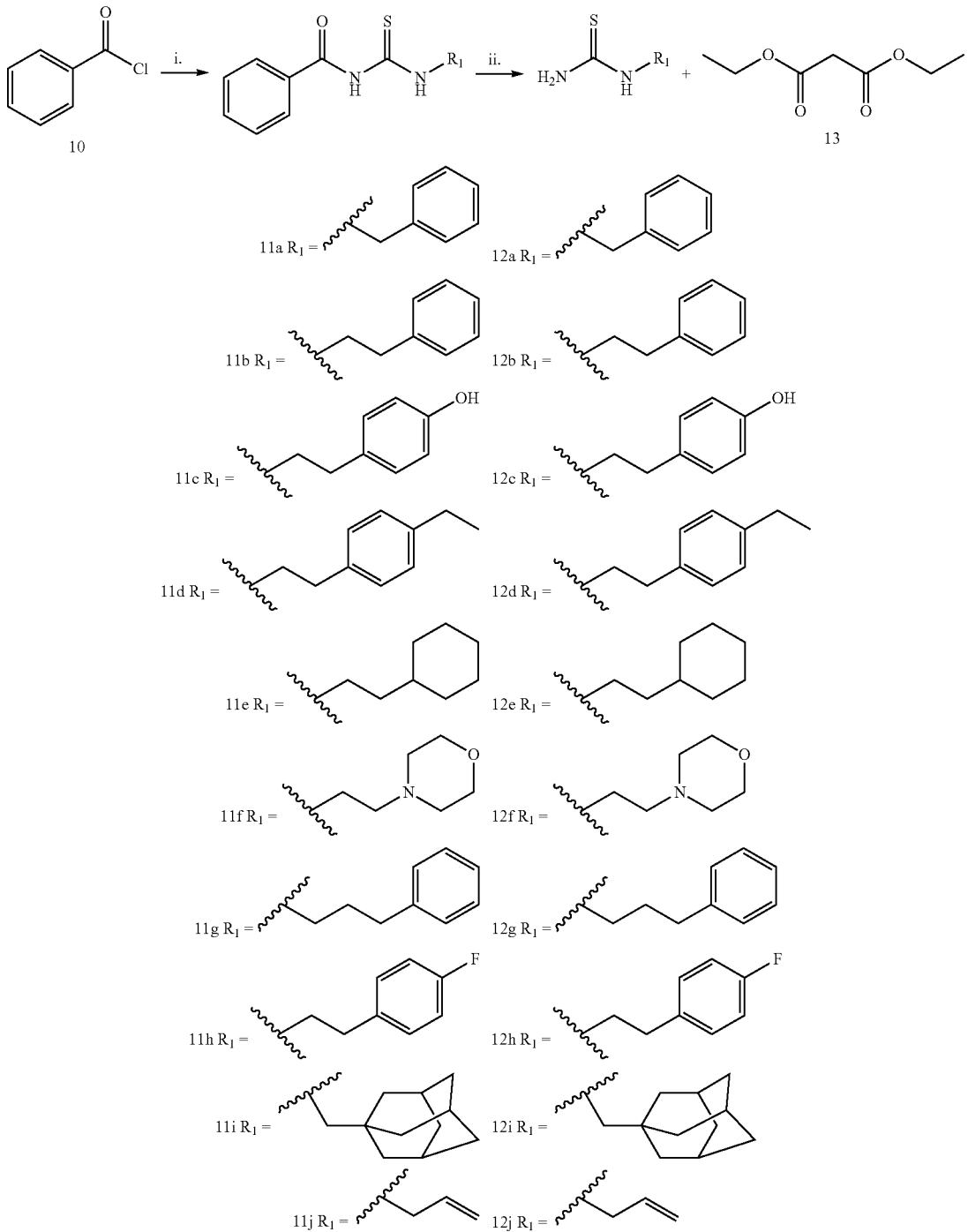

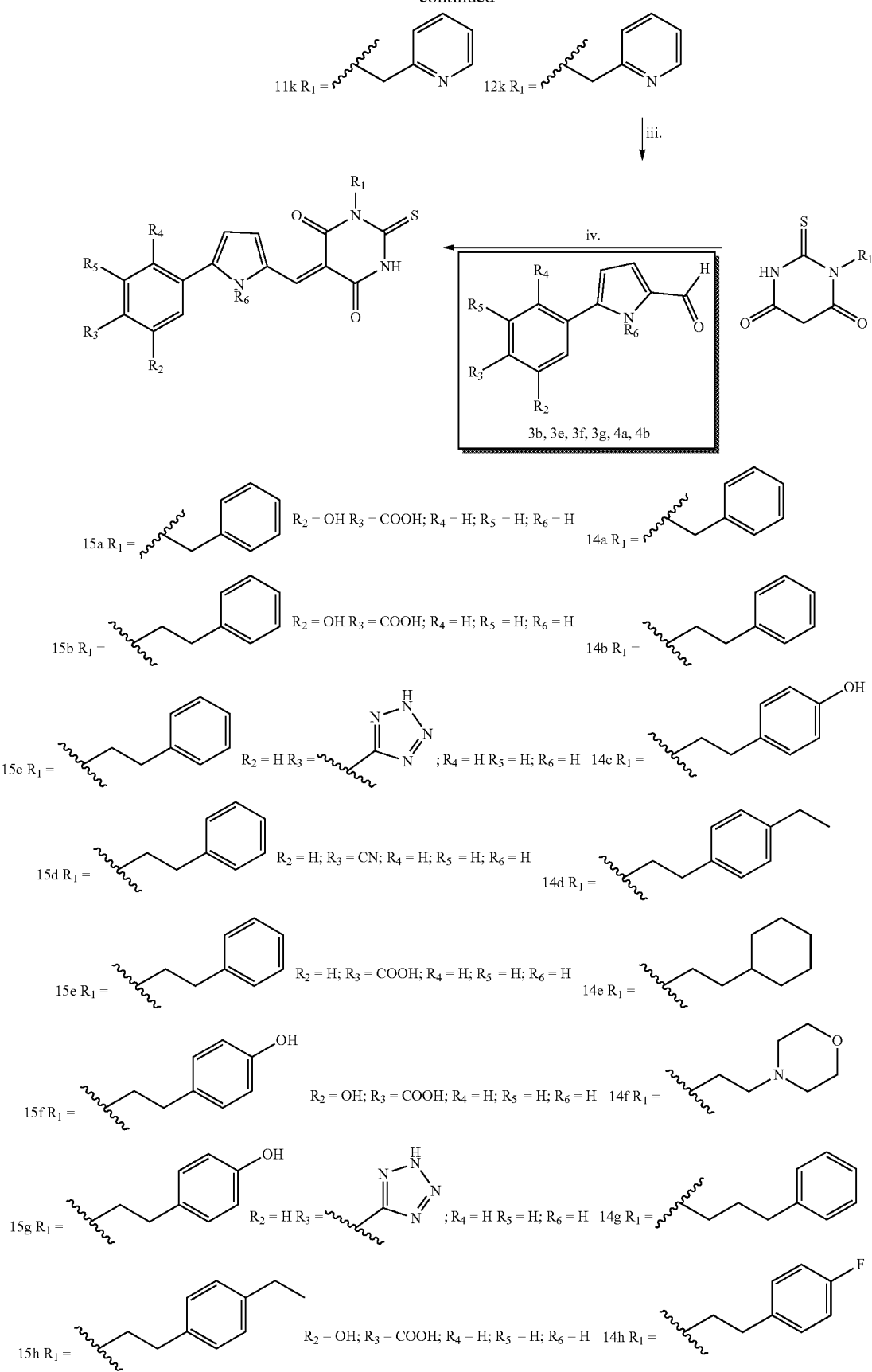

-continued

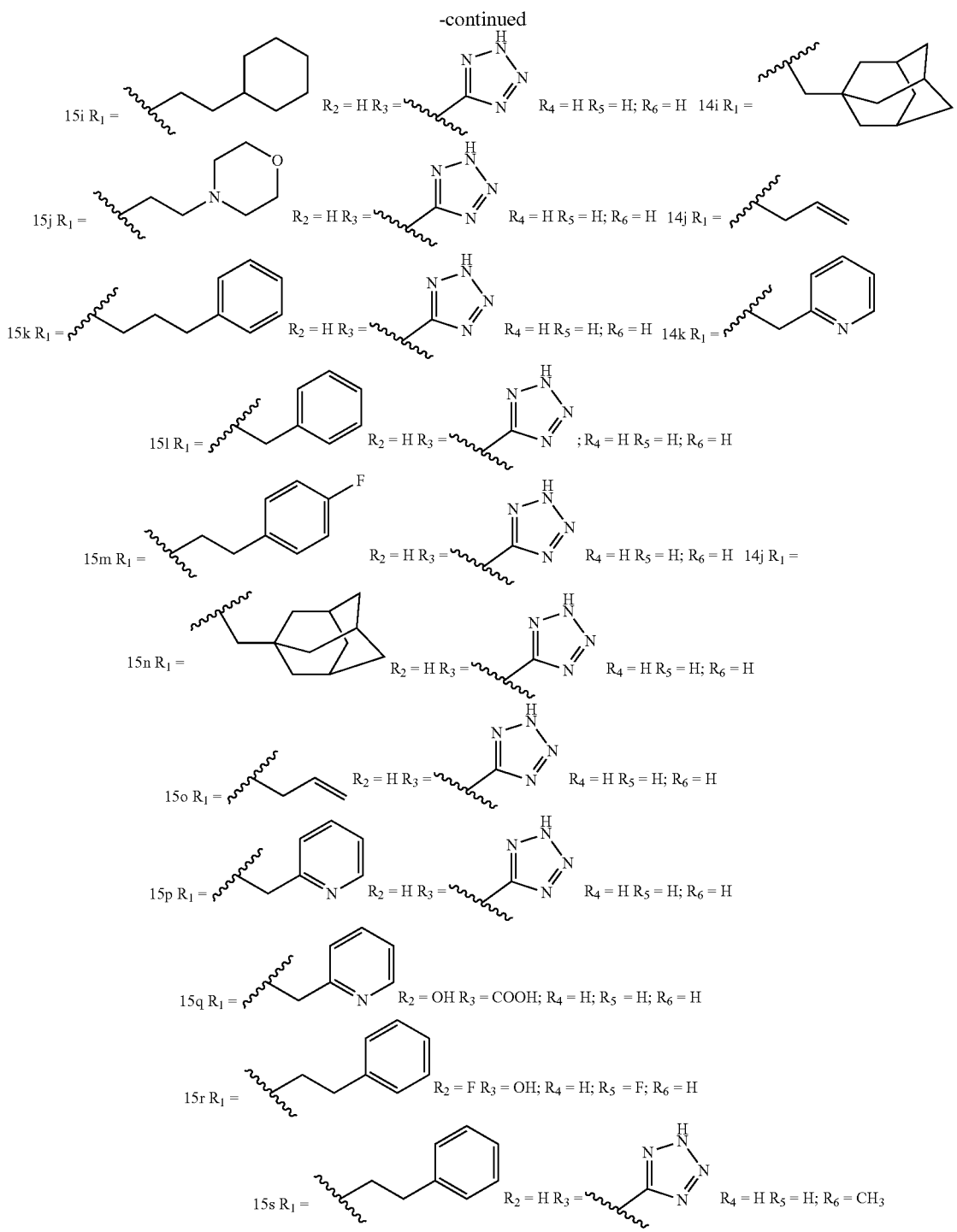

i. a) NH$_4$SCN, (CH$_3$)$_2$CO, 60° C. MW, 15 min, b) opportune amine of formula NH$_2$R$_1$, (CH$_3$)$_2$CO, 60° C. MW, 15 min. ii. NH$_2$NH$_2$; iii. Na$^0$, EtOH, reflux, iv) opportune aldehyde, HCl, EtOH, 70° C.

General Procedure for the Synthesis of Compounds 11a-k:

Benzoylchloride 10 (4.31 mmol, 1.00 eq) was dissolved in 3 mL of acetone. To this, NH$_4$SCN (5.17 mmol, 1.2 eq) was added in one portion, and the mixture irradiated at 60° C. for 15 minutes at the microwave. After this time, the opportune amine of formula NH$_2$R$_1$ (1.00 eq) was added, and the mixture was irradiated for further 15 min at the microwave. The resulting suspension was filtered, and the precipitate washed with H$_2$O and CH$_3$OH, to furnish pure 11a-k as white solids. The amine of formula NH$_2$R$_1$ wherein R$_1$ is cyclohexylethyl (2-cyclohexylethan-1-amine, compound 21) was prepared according to the procedure described in Example 8.

Benzylamine was purchased from Sigma Aldrich (catalogue number 407712), 2-Phenethylamine was purchased from Sigma Aldrich (catalogue number 407267), tyramine was purchased from Sigma Aldrich (catalogue number T90344), 4-Ethylphenethylamine was purchased from Sigma Aldrich (catalogue number 560537), 4-(2-Aminoethyl)morpholine was purchased from Sigma Aldrich (catalogue number A55004), 3-Phenyl-1-propylamine was purchased from Sigma Aldrich (catalogue number P32406), 3-(4-fluoro-phenyl)-propylamine was purchased from Sigma Aldrich (catalogue number CDS009095), 1-Adamantanemethylamine was purchased from Sigma Aldrich (catalogue number 180378), Allylamine was purchased from Sigma Aldrich (catalogue number 145831), 2-Picolylamine was purchased from Sigma Aldrich (catalogue number A65204).

N-(benzylcarbamothioyl)benzamide (11a)

yield 50% white solid. $^1$H NMR: (400 MHz CDCl$_3$) δ (ppm) 11.05 (bs, 1H), 9.27 (bs, 1H), 7.80 (d, 2H, J=8.4 Hz), 7.57 (t, 1H, J=14.8 Hz), 7.45 (t, 2H, J=15.2 Hz), 7.39-7.30 (m, 5H), 4.91 (d, 2H, J=5.2 Hz) ppm. MS: (ESI) m/z 268.9 [M−H]$^-$.

N-(phenethylcarbamothioyl)benzamide (11b)

yield 47% white solid. $^1$H NMR: (400 MHz CDCl$_3$) δ (ppm) 10.78 (bs, 1H), 9.09 (bs, 1H), 7.80 (d, 2H, J=7.2 Hz), 7.60 (t, 1H, J=14.8 Hz), 7.48 (t, 2H, J=15.6 Hz), 7.36-7.23 (m, 5H), 3.95 (q, 2H, J=20.4 Hz), 3.03 (t, 2H, J=14.4 Hz) ppm. MS: (ESI) m/z 282.9 [M−H]$^-$.

N-((4-hydroxyphenethyl)carbamothioyl)benzamide (11c)

yield: 40%. $^1$H NMR: (400 MHz CD$_3$Cl$_3$) δ (ppm) 10.69 (bs, 1H), 8.96 (bs, 1H), 7.79-7.77 (d, 2H, J=8 Hz), 7.60-7.57 (m, 1H), 7.48-7.47 (m, 2H), 7.12-7.10 (d, 2H, J=8 Hz), 6.78-6.76 (d, 2H, J=8 Hz), 3.91-3.86 (m, 2H), 2.94-2.90 (m, 2H). MS: (ESI) m/z 299.8 [M−H]$^-$.

N-((4-ethylphenethyl)carbamothioyl)benzamide (11d)

yield: 56%. $^1$H NMR: (400 MHz CD$_3$Cl$_3$) δ (ppm) 10.72 (bs, 1H), 8.93 (bs, 1H), 7.79-7.77 (d, 2H, J=8 Hz), 7.60-7.56 (m, 3H), 7.49-7.47 (d, 2H, J=8 Hz), 7.18-7.12 (m, 4H), 3.93 (m, 2H), 2.98-2.95 (m, 2H), 2.63-2.57 (m, 2H), 1.22-1.18 (m, 3H, J=7.6 Hz). MS: (ESI) m/z 311 [M−H]$^-$.

N-((2-cyclohexylethyl)carbamothioyl)benzamide (11e)

yield: 40%. $^1$H NMR: (400 MHz CD$_3$Cl$_3$) δ (ppm) 10.65 (bs, 1H), 8.94 (bs, 1H), 7.81-7.78 (m, 2H), 7.61-7.57 (m, 1H), 7.50-7.45 (m, 2H), 3.72-3.66 (m, 2H), 1.76-1.67 (m, 5H), 1.59-1.55 (m, 2H), 1.28-1.10 (m, 4H), 1.05-0.86 (m, 2H). MS: (ESI) m/z 289.1 [M−H]$^-$.

N-((2-morpholinoethyl)carbamothioyl)benzamide (11f)

yield: 71%. $^1$H NMR: (400 MHz CD$_3$Cl$_3$) δ (ppm) 10.95 (bs, 1H), 9.00 (bs, 1H), 7.85-7.82 (m, 2H), 762-7.59 (m, 1H), 753-7.48 (m, 2H), 3.83-3.78 (m, 6H), 2.71 (s, 2H), 2.57 (s, 4H). MS: (ESI) m/z 292.1 [M−H]$^-$.

N-((3-phenylpropyl)carbamothioyl)benzamide (11g)

yield: 86%. $^1$H NMR: (400 MHz CD$_3$Cl$_3$) δ (ppm) 10.78 (bs, 1H), 9.00 (bs, 1H), 7.85-7.83 (d, 2H, J=7.6 Hz), 7.65-7.61 (m, 1H), 7.54-7.52 (m, 2H), 7.32-7.29 (m, 2H), 7.24-7.19 (m, 3H), 3.76-3.72 (m, 2H), 2.77-2.74 (m, 2H), 2.11-2.04 (m, 2H). MS: (ESI) m/z 321 [M+Na]$^+$.

N-((4-fluorophenethyl)carbamothioyl)benzamide (11h)

yield 93%. $^1$H NMR (400 MHz, CDCl$_3$): δ (ppm) 10.75 (bs, 1H), 8.98 (bs, 1H), 7.83-7.81 (d, J=7.6 Hz, 2H), 7.64-7.60 (t, J=7.2 Hz, 1H), 7.53-7.49 (t, J=7.2 Hz, 2H), 7.26-7.22 (q, J=8.8 Hz, 2H), 7.04-7.00 (t, J=8.4 Hz, 2H), 3.94-3.92 (t, J=6 Hz, 2H), 3.03-2.99 (t, J=7.2 Hz, 2H). MS: (ESI) m/z 300.8 [M−H]$^-$.

N-(((adamantan-1-yl)methyl)carbamothyol)benzamide (11i)

yield 85%. $^1$H NMR (400 MHz, CDCl$_3$): δ (ppm) 10.88 (bs, 1H), 9.003 (bs, 1H), 7.86-7.84 (d, J=7.2 Hz, 2H), 7.64-7.61 (t, J=7.2 Hz, 1H), 7.54-7.50 (t, J=7.6 Hz, 2H), 3.46-3.44 (d, J=5.6 Hz, 2H), 2.03 (s, 3H), 1.76-1.67 (m, 8H), 1.63 (s, 6H). MS: (ESI) m/z 326.8 [M−H]$^-$.

N-(allylcarbamothioyl)benzamide (11j)

yield 78%. $^1$H NMR (400 MHz, CDCl$_3$): δ (ppm) 10.80 (bs, 1H), 9.03 (bs, 1H), 7.85-7.83 (d, J=7.6 Hz, 2H), 7.64-7.61 (t, J=7.2 Hz, 1H), 7.53-7.50 (t, J=8 Hz, 2H), 6.02-5.92 (m, 1H), 5.36-5.25 (m, 2H), 4.37-4.35 (dd, J$_1$=9.6 Hz, J$_2$=1.2 Hz, 2H). MS: (ESI) m/z 218.9 [M−H]$^-$.

N-((pyridin-2-ylmethyl)carbamothioyl)benzamide (11k)

Yield: 78%. $^1$H NMR (400 MHz CD$_3$Cl$_3$) δ (ppm) 11.61 (bs, 1H), 9.12 (bs, 1H), 8.61-8.60 (m, 1H), 7.85-7.83 (d, 2H, J=8 Hz), 7.70-7.66 (m, 1H), 7.59-7.56 (m, 1H), 7.49-7.45 (m, 2H), 7.33-7.31 (d, 1H, J=8 Hz), 7.23-7.20 (m, 1H), 5.01-5.00 (d, 2H, J=4 Hz). MS: (ESI) m/z 271.8 [M+H]$^+$.

General Procedure for the Synthesis of Compounds 12a-12k:

The opportune thioureido derivative (11a-11k) (1.61 mmol) was dissolved in 10 mL of hydrazine monohydrate. The solution was stirred at rt for 3 h. Then 5 mL of fuming hydrochloric acid were added, and the mixture was extracted with CH$_2$Cl$_2$ (3×15 mL). The organic phase was washed with Na$_2$CO$_3$ (aq. sol.) (2×50 ml), and dried over Na$_2$SO$_4$. The solvent was removed at reduced pressure and the corresponding residue purified by flash chromatography (AcOEt/CH$_2$Cl$_2$ 1:1).

1-benzylthiourea (12a)

yield 80% white solid. $^1$H NMR (400 MHz DMSO-d$_6$) δ 7.94 (bs, 1H), 7.33-7.21 (m, 5H), 7.03 (bs, 2H), 4.60 (s, 2H) ppm; MS: (ESI) m/z 166.9 [M+H]$^+$.

1-phenethylthiourea (12b)

yield 95% white solid. $^1$H NMR (400 MHz DMSO-d$_6$) δ 7.33 (t, 2H, J=14.4 Hz), 7.26 (t, 1H, 6.8 Hz), 7.21 (d, 2H, J=7.2 Hz), 5.68 (bs, 2H), 2.91 (t, 2H, J=14.0 Hz) ppm. MS: (ESI) m/z 178.9 [M−H]$^-$.

1-(4-hydroxyphenethyl)thiourea (12c)

yield: quantitative. $^1$H NMR: (400 MHz MeOD) δ (ppm) 7.02-7.00 (d, 2H, J=8 Hz), 6.69-6.66 (d, 2H, J=12 Hz), 3.27-3.26 (m, 2H), 2.74-2.71 (m, 2H). MS: (ESI) m/z 195.2 [M−H]$^−$.

1-(4-ethylphenethyl)thiourea (12d)

yield: 92%. $^1$H NMR: (400 MHz MeOD) δ (ppm) 7.12-7.07 (m, 4H), 3.27-3.26 (m, 2H), 2.80-2.77 (m, 2H), 2.59-2.53 (m, 2H), 1.18-1.14 (t, 3H, J=7.6 Hz) MS: (ESI) m/z 208.9 [M−+H]$^+$.

1-(2-cyclohexylethyl)thiourea (12e)

yield: 89%. $^1$H NMR: (400 MHz MeOD) δ (ppm) 3.47 (s, 1H), 3.11 (s, 1H), 1.73-1.61 (m, 5H), 1.44-1.38 (m, 2H), 1.25-1.22 (m, 4H), 0.99-0.95 (m, 2H). MS: (ESI) m/z 187 [M+H]$^+$, 209 [M+Na]$^+$.

1-(2-morpholinoethyl)thiourea (12f)

yield: 47%. $^1$H NMR: (400 MHz MeOD) δ (ppm) 3.69-3.67 (m, 6H), 2.55-2.53 (m, 2H), 2.52-2.49 (m, 4H). MS: (ESI) m/z 189.9 [M+H]$^+$, 212 [M+Na]$^+$.

1-(3-phenylpropyl)thiourea (12g)

yield 92%. $^1$H NMR: (400 MHz MeOD) δ (ppm) 7.28-7.26 (m, 2H), 7.24-7.16 (m, 3H), 4.81-4.77 (m, 2H), 2.67-2.64 (m, 2H), 1.91-1.83 (m, 2H). MS: (ESI) m/z 193 [M−H]$^−$.

1-(4-fluorophenethyl)thiourea (12h)

yield 79%. $^1$H-NMR (400 MHz, MeOD): δ (ppm) 7.26-7.22 (q, J=5.6 Hz, 2H), 7.02-6.98 (t, J=8.8 Hz, 2H), 3.68-3.65 (m, 2H), 2.87-2.84 (t, J=6.4 Hz, 2H MS: (ESI) m/z 196.9 [M−H]$^−$.

1-((adamantan-1yl)methyl)thiourea (12i)

yield 80%. $^1$H-NMR (400 MHz, CDCl$_3$): δ (ppm) 6.41 (bs, 1H), 5.93 (bs, 1H), 3.30 (s, 1H), 2.78 (s, 1H), 2.02 (s, 3H), 1.75-1.62 (m, 8H), 1.54 (s, 6H). MS: (ESI) m/z 122.9 [M−H]$^−$.

1-allylthiourea (12j)

yield 88%. $^1$H-NMR (400 MHz, CDCl$_3$): δ (ppm) 6.66 (bs, 1H), 5.98 (bs, 2H), 5.88-5.83 (m, 1H), 5.34-5.29 (m, 2H), 4.21-4.23 (dd, J=10.2 Hz, J$_2$=1.6 Hz, 2H). MS: (ESI) m/z 114.9 [M−H]$^−$.

1-(pyridin-2-ylmethyl)thiourea (12k)

yield: 63%. $^1$H NMR: (400 MHz MeOD) δ (ppm) 7.81-7.80 (m, 2H), 7.50-7.47 (m, 1H), 7.41-7.38 (m, 1H), 4.79 (s, 2H). MS: (ESI) m/z 165.6 [M−H]$^−$.

General Procedure for the Synthesis of Compounds 14a-k:

Sodium metal (3.61 mmol, 3 eq) was dissolved in anhydrous EtOH (10 mL), then the opportune thiourea compound (12a-k) (1.20 mmol) and diethylmalonate 13 (2.41 mmol) were added subsequentially, and the mixture was refluxed under Argon atmosphere. The solvent was removed at reduced pressure and the corresponding residue was solubilized in water. The mixture was acidified at pH 2 with HCl 1N and the solvent evaporated at reduced pressure. The residue was then purified by flash chromatography (CH$_2$Cl$_2$/CH$_3$OH 8:2).

1-benzyl-2-thioxodihydropyrimidine-4,6(1H,5H)-dione (14a)

yield 99% red solid. $^1$H NMR: (400 MHz DMSO-d$_6$) δ 10.54 (bs, 1H), 7.23-7.15 (m, 5H), 5.39 (s, 2H), 4.30 (s, 1H) ppm. MS: (ESI) m/z 232.9 [M−H]$^−$.

1-phenethyl-2-thioxodihydropyrimidine-4,6(1H,5H)-dione (14b)

yield 80% white solid. $^1$H NMR: (400 MHz DMSO-d$_6$) δ (ppm) 10.76 (bs, 1H), 7.29-7.19 (m, 5H), 4.33 (t, 2H, J=16.0), 3.14 (s, 1H), 2.83 (t, 2H, J=16.0) ppm. MS: (ESI) m/z 246.9 [M−H]$^−$.

1-(4-hydroxyphenethyl)-2-thioxodihydropyrimidine-4,6(1H,5H)-dione (14c)

yield 67%. $^1$H NMR: (400 MHz MeOD) δ (ppm) 7.08-7.03 (m, 2H), 6.68-6.67 (m, 2H), 4.43-4.33 (m, 2H), 2.84-2.83 (m, 2H). MS: (ESI) m/z 262.8 [M−H]$^−$.

1-(4-ethylphenethyl)-2-thioxodihydropyrimidine-4,6(1H,5H)-dione (14d)

yield 62%. $^1$H NMR: (400 MHz MeOD) δ (ppm) 7.19-7.17 (m, 2H), 7.08-7.07 (m, 2H), 4.45-4.43 (m, 2H), 2.91-2.87 (m, 2H), 2.59-2.53 (m, 2H), 1.22-1.18 (m, 3H, J=7.6 Hz). MS: (ESI) m/z 274.8 [M−H]$^−$.

1-(2-cyclohexylethyl)-2-thioxodihydropyrimidine-4,6(1H,5H)-dione (14e)

yield 42%. $^1$H NMR: (400 MHz MeOD) δ (ppm) 4.29 (m, 2H), 1.75-1.59 (m, 6H), 1.52-1.54 (m, 2H), 1.27-1.16 (m, 5H), 0.99-0.93 (m 2H). MS: (ESI) m/z 252.9 [M−H]$^−$.

1-(2-morpholinoethyl)-2-thioxodihydropyrimidine-4,6(1H,5H)-dione (14f)

yield 78%. $^1$H NMR: (400 MHz MeOD) δ (ppm) 4.57-4.54 (m, 2H), 3.73-3.71 (m, 4H), 2.82-2.78 (m, 2H), 2.73-2.72 (m, 4H), 1.96-1.95 (m, 2H). MS: (ESI) m/z 255.6 [M−H]$^−$.

1-(3-phenylpropyl)-2-thioxodihydropyrimidine-4,6(1H,5H)-dione (14g)

yield 60%. $^1$H NMR: (400 MHz MeOD) δ (ppm) 7.26-7.21 (m, 4H), 7.16-7.14 (m, 1H), 4.39-4.30 (m, 2H), 2.69-2.65 (t, 2H, J=8 Hz), 2.06-2.0 (m, 2H). MS: (ESI) m/z 260.8 [M−H]$^−$.

1-(4-fluorophenethyl)-2-thioxodihydropirimidine-4,6(1H,5H)-dione (14h)

yield 62%. $^1$H-NMR (400 MHz, MeOD): δ (ppm) 7.33-7.30 (q, J=6 Hz, 2H), 7.01-6.96 (t, J=8.8 Hz, 2H), 4.49-4.45 (m, 2H), 3.71 (s, 1H), 2.98-2.94 (t, 5.6 Hz, 2H). MS: (ESI) m/z 264.8 [M−H]$^−$.

1-((adamantan-1-yl)methyl)-2-thioxodihydropirimidine-4,6(1H,5H)-dione (14i)

yield 54%. $^1$H-NMR (400 MHz, CDCl$_3$): δ (ppm) 9.08 (bs, 1H), 4.23 (s, 1H), 3.72 (s, 2H), 1.96 (s, 3H), 1.70-1.62 (m 8H), 1.58 (s, 6H) ppm. MS: (ESI) m/z 222.9 [M−H]$^-$.

1-allyl-2-thioxodihydropirimidine-4,6(1H,5H)-dione (14j)

yield 48%. $^1$H-NMR (400 MHz, MeOD): δ (ppm) 5.91-5.85 (m, 1H), 5.17-5.15 (d, J=6.4 Hz, 1H), 4.97-4.96 (d, J=6.4 Hz, 1H), 4.27-4.18 (dd, J$_1$=9.2 Hz, J$_2$=1.6 Hz, 2H), 3.11 (s, 1H) ppm. MS: (ESI) m/z 182.9 [M−H]$^-$.

1-(pyridin-2-ylmethyl)-2-thioxodihydropyrimidine-4,6(1H,5H)-dione (14k)

yield 57%. $^1$H NMR: (400 MHz MeOD) δ (ppm) 8.38 (s, 1H), 7.69-7.65 (m, 1H), 7.19-7.18 (m, 1H), 7.03-7.01 (m, 1H), 5.64 (s, 2H), 3.28 (s, 1H). MS: (ESI) m/z 233.9 [M−H]$^-$.

General Procedure for the Synthesis of Compounds 15a-s:

The opportune aldehyde 3b, 3e, 3f, 3g, 4a or 4b (0.22 mmol, 1 eq) and compound 14a-14k (0.22 mmol, 1 eq) were suspended in EtOH (6 mL), to this, 3 drops of HCl (conc.) were added, and the mixture was stirred at 70° C. overnight. After this time 3 mL of HCl were added, and the resulting precipitate was filtered at reduced pressure, to give a solid that was washed with H$_2$O, CH$_3$OH and hexane.

(Z)-4-(5-((1-benzyl-4,6-dioxo-2-thioxotetrahydropyrimidin-5(2H)-ylidene)methyl)-1H-pyrrol-2-yl)-2-hydroxybenzoic Acid (15a)

aspect: brown solid; yield 42%.

Compound 15a was prepared from compound 14a and compound 4a. $^1$H NMR: (400 MHz (CD$_3$)$_2$SO) δ (ppm) 11.40 (bs, 1H), 8.13 (bs, 1H), 7.85 (m, 1H), 7.30-7.21 (m, 10H), 5.50 (s, 2H); $^{13}$C NMR: (101 MHz (CD$_3$)$_2$SO) δ (ppm) 178.61, 171.76, 161.89, 142.75, 141.65, 136.96, 135.72, 131.95, 128.58, 127.33, 127.23, 116.46, 115.34, 113.64, 49.36. MS: (ESI) m/z 445.8 [M−H]$^-$.

(Z)-4-(5-((4,6-dioxo-1-phenethyl-2-thioxotetrahydropyrimidin-5(2H)-ylidene)methyl)-1H-pyrrol-2-yl)-2-hydroxybenzoic Acid (15b)

aspect red solid Yield: 90%. Compound 15b was prepared from compound 14b and compound 4a. $^1$H NMR (400 MHz (CD$_3$)$_2$SO) δ (ppm) 8.18 (s, 1H), 7.90 (d, 1H, J=2.8 Hz), 7.40-7.18 (m, 9H), 4.45 (t, 2H, J=16.4), 2.91 (t, 2H, J=16.0 Hz). $^{13}$C NMR: (100 MHz (CD$_3$)$_2$SO) δ (ppm) 178.1, 171.7, 162.1, 161.9, 142.7, 141.6, 140.0, 138.8, 132.0, 131.6, 129.0, 128.9, 126.8, 116.5, 115.3, 114.0, 113.8, 113.7, 47.6, 32.9. MS: (ESI) m/z 459.8 [M−H]$^-$.

(Z)-5-((5-(4-(1H-tetrazol-5-yl)phenyl)-1H-pyrrol-2-yl)methylene)-dihydro-3-henethyl-2-thioxopyrimidine-4,6(1H,5H)-dione (15c)

The crude product was purified by flash chromatography in DCM/MeOH 9:1 to obtain compound 15c as a red solid. Yield: 80% Compound 15c was prepared from compound 14b and compound 3b. $^1$H NMR: (400 MHz (CD$_3$)$_2$SO) δ (ppm) 8.13-8.11 (m, 2H), 7.85-7.84 (s, 2H), 7.41 (s, 1H), 7.31-7.29 (m, 4H), 7.19-7.18 (m, 2H), 6.85 (s, 1H), 4.50-4.49 (m, 2H), 2.92-2.90 (m, 2H). $^{13}$C NMR: (100 MHz (CD$_3$)$_2$SO) δ (ppm) 181.8, 176.6, 171.4, 161.0, 150.7, 145.3, 140.4, 138.9, 135.1, 131.9, 129.1, 129.0, 127.4, 126.5, 119.6, 114.5, 98.9, 57.3, 26.47. MS: (ESI) m/z 468.5 [M−H]$^-$.

4-(5-((Z)-(tetrahydro-4,6-dioxo-3-phenethyl-2-thioxopyrimidin-5(6H)-lidene)methyl)-1H-pyrrol-2-yl)benzonitrile (15d)

(Purification eluent: DCM) orange solid. (Yield 55%). Compound 15d was prepared from compound 14b and compound 3e. $^1$H NMR: (400 MHz (CD$_3$)$_2$SO) δ (ppm) 8.16 (s, 1H), 7.94-7.90 (m, 5H), 7.27-7.18 (m, 5H), 4.41-4.40 (m, 2H), 2.87-2.86 (m, 2H). $^{13}$C NMR: (100 MHz (CD$_3$)$_2$SO) δ (ppm) 181.8, 176.6, 171.4, 163.1, 150.7, 142.0, 138.9, 133.8, 132.0, 129.0, 128.5, 126.4, 119.0, 115.8, 98.9, 47.2, 26.5. MS: (ESI) m/z 424.6 [M−H]$^-$.

4-(5-((Z)-(tetrahydro-4,6-dioxo-3-phenethyl-2-thioxopyrimidin-5(6H)-ylidene)methyl)-1H-pyrrol-2-yl)benzoic Acid (15e)

Aspect: red solid Yield 69% Compound 15e was prepared from compound 14b and compound 4b. $^1$H NMR: (400 MHz (CD$_3$)$_2$SO) δ (ppm) 8.15 (s, 1H), 8.05-8.04 (m, 2H), 7.93-7.86 (m, 3H), 7.29-7.20 (m, 6H), 4.45-4.43 (m, 2H), 2.91-2.90 (m, 2H). $^{13}$C NMR: (100 MHz (CD$_3$)$_2$SO) δ (ppm) 179.5, 178.2, 167.1, 162.2, 143.3, 139.0, 133.4, 130.8, 129.1, 128.9, 126.9, 126.0, 125.9, 115.2, 47.7, 32.9. MS: (ESI) m/z 443.6 [M−H]$^-$.

(Z)-2-hydroxy-4-(5-((1-(4-hydroxyphenethyl)-4,6-dioxo-2-thioxotetrahydropyrimidin-5(2H)-ylidene)methyl)-1H-pyrrol-2-yl)benzoic Acid (15f)

Compound 15f was prepared from compound 14c and compound 4a. yield 50%. $^1$H NMR: (400 MHz (CD$_3$)$_2$SO) δ (ppm) 9.30 (s, 1H), 9.29 (bs, 1H), 8.14 (bs, 1H), 7.81-7.79 (d, 1H, J=7.6), 7.51 (bs, 1H), 7.11-7.02 (m, 7H), 6.69-6.68 (m, 2H), 4.41-4.37 (m, 2H), 3.06-3.04 (m, 2H). $^{13}$C NMR: (100 MHz (CD$_3$)$_2$SO) δ (ppm) 178.1, 171.5, 163.9, 162.4, 156.3, 145.5, 141.0, 132.9, 132.5, 131.6, 130.0, 129.0, 125.4, 115.8, 115.1, 114.3, 113.2. MS: (ESI) m/z 476.6 [M−H]$^-$.

(Z)-5-((5-(4-(1H-tetrazol-5-yl)phenyl)-1H-pyrrol-2-yl)methylene)-1-(4-hydroxyphenethyl)-2-thioxodihydropyrimidine-4,6(1H,5H)-dione (15g)

Compound 15g was prepared from compound 14c and compound 3b. yield 50%. $^1$H NMR: (400 MHz (CD$_3$)$_2$SO) δ (ppm) 9.21 (bs, 1H), 8.18-8.16 (d, 2H, J=8 Hz), 8.04-8.03 (m, 1H), 7.98-7.96 (m, 2H), 7.28 (s, 1H), 7.11-7.09 (m, 1H), 7.05-7.03 (d, 2H, J=8.4 Hz), 6.71-6.69 (d, 2H, J=8 Hz), 4.39-4.39 (m, 2H), 2.81-2.79 (m, 2H). $^{13}$C NMR: (100 MHz (CD$_3$)$_2$SO) δ (ppm) 178.4, 178.1, 162.1, 156.3, 155.7, 143.4, 141.3, 131.9, 131.6, 129.9, 129.8, 129.0, 128.9, 128.2, 126.7, 125.8, 115.7, 114.9, 47.9, 32.2. MS: (ESI) m/z 483.6 [M−H]$^-$.

(Z)-4-(5-((1-(4-ethylphenethyl)-4,6-dioxo-2-thioxotetrahydropyrimidin-5(2H)-ylidene)methyl)-1H-pyrrol-2-yl)-2-hydroxybenzoic Acid (15h)

Compound 15h was prepared from compound 14d and compound 4a. yield 50%. $^1$H NMR: (400 MHz (CD$_3$)$_2$SO)

δ (ppm) 8.12-8.10 (m, 1H), 7.79-7.77 (m, 1H), 7.50 (s, 1H), 7.12-7.09 (m, 7H), 4.41-4.40 (m, 2H), 2.86-2.85 (m, 2H), 2.56-2.54 (m, 2H), 1.12-1.03 (m, 3H). $^{13}$C NMR: (100 MHz (CD$_3$)$_2$SO) δ (ppm) 178.2, 177.8, 164.4, 162.4, 157.1, 145.7, 142.3, 140.7, 136.1, 133.4, 132.5, 132.2, 131.5, 129.0, 128.4, 122.0, 115.0, 113.2, 47.8, 32.9, 32.6, 16.1. MS: (ESI) m/z 487.5 [M−H]$^-$.

(Z)-5-((5-(4-(1H-tetrazol-5-yl)phenyl)-1H-pyrrol-2-yl)methylene)-1-(2-cyclohexylethyl)-2-thioxodihydropyrimidine-4,6(1H,5H)-dione (15i)

Compound 15i was prepared from compound 14e and compound 3b. yield 50%. $^1$H NMR: (400 MHz (CD$_3$)$_2$SO) δ (ppm) 8.13-8.11 (m, 3H), 7.98-7.91 (m, 2H), 7.48 (s, 1H), 7.23 (s, 1H), 4.20-7.18 (m, 2H), 1.66-1.61 (m, 5H), 1.45-1.43 (m, 2H), 1.22-1.14 (m, 4H), 0.92-0.89 (m, 2H). $^{13}$C NMR: (100 MHz (CD$_3$)$_2$SO) δ (ppm) 178.3, 178.0, 162.0, 161.0, 143.2, 142.0, 140.7, 131.9, 128.2, 126.6, 114.3, 107.1, 44.8, 36.0, 35.3, 33.0, 32.5, 26.4. MS: (ESI) m/z 473.9 [M−H]$^-$.

(Z)-5-((5-(4-(1H-tetrazol-5-yl)phenyl)-1H-pyrrol-2-yl)methylene)-1-(2-morpholinoethyl)-2-thioxodihydropyrimidine-4,6(1H,5H)-dione (15j)

Compound 15j was prepared from compound 14f and compound 3b. yield 50%. $^1$H NMR: (400 MHz (CD$_3$)$_2$SO) δ (ppm) 8.19-8.15 (m, 2H), 8.11 (s, 1H), 7.87-7.86 (d, 2H, 7.6 Hz), 7.13-7.12 (m, 1H), 6.95-6.92 (m, 1H), 4.54-4.51 (m, 2H), 3.70-3.69 (m, 4H), 2.79-2.71 (m, 2H), 2.66-2.62 (m, 4H). $^{13}$C NMR: (100 MHz (CD$_3$)$_2$SO) δ (ppm) 178.0, 163.2, 162.5, 160.7, 145.2, 140.4, 132.0, 131.5, 129.5, 127.1, 125.8, 113.7, 105.2, 66.2, 54.8, 53.6, 42.7, 29.4. MS: (ESI) m/z 477.2 [M−H]$^-$.

(Z)-5-((5-(4-(1H-tetrazol-5-yl)phenyl)-1H-pyrrol-2-yl)methylene)-1-(3-phenylpropyl)-2-thioxodihydropyrimidine-4,6(1H,5H)-dione (15k)

Compound 15k was prepared from compound 14g and compound 3b. yield 50%. $^1$H NMR: (400 MHz (CD$_3$)$_2$SO) δ (ppm) 8.15-8.13 (m, 4H), 7.96-7.94 (m, 2H), 7.23-7.16 (m, 5H), 7.12-7.11 (m, 1H), 4.27-4.26 (m, 2H), 2.64-2.57 (m, 2H), 1.93-1.91 (m, 2H). $^{13}$C NMR: (100 MHz (CD$_3$)$_2$SO) δ (ppm) 178.5, 178.2, 162.3, 161.1, 155.5, 143.2, 141.6, 141.3, 140.6, 131.9, 128.6, 128.5, 128.3, 126.6, 126.2, 125.5, 114.9, 107.4, 46.25, 32.9, 28.3. MS: (ESI) m/z 482.1 [M−H]$^-$.

(Z)-5-((5-(4-(1H-tetrazol-5-yl)phenyl)-1H-pyrrol-2-yl)methylene)-1-benzyl-2-thioxodihydropyrimidine-4,6(1H,5H)-dione (15l)

Compound 15l was prepared from compound 14a and compound 3b. yield 40%. $^1$H NMR: (400 MHz (CD$_3$)$_2$SO) δ (ppm) 8.22-8.16 (m, 3H), 8.04-8.02 (m, 2H), 7.33-7.30 (m, 6H), 7.23 (m, 1H), 5.55 (s, 2H). $^{13}$C NMR: (100 MHz (CD$_3$)$_2$SO) δ (ppm) 180.0, 178.7, 162.6, 161.2, 143.5, 141.5, 140.9, 137.1, 132.3, 131.8, 128.6, 128.4, 127.4, 127.3, 126.7, 125.3, 115.1, 107.1, 49.4. MS: (ESI) m/z 454.0 [M−H]$^-$.

(Z)-5-((5-(4-(1H-tetrazol-5-yl)phenyl)-1H-pyrrol-2-yl)methylene)-1-(4-fluorophenethyl)-2-thioxodihydropiridimine-4,6(1H,5H)-dione (15m)

Compound 15m was prepared from compound 14h and compound 3b. yield 74%. $^1$H-NMR (400 MHz, DMSO-d$^6$): δ (ppm) 8.21-8.20 (d, J=4.4 Hz, 3H), 8.08 (s, 1H), 8.04-8.02 (d, J=6.4 Hz, 2H), 7.33-7.29 (q, J=7.6 Hz, 3H), 7.14-7.12 (t, J=5.2 Hz, 2H), 4.44-4.42 (t, J=5.2 Hz, 2H), 2.66-2.64 (t, J=5.6 Hz, 2H). $^{13}$C-NMR (100 MHz, DMSO-d$^6$): δ (ppm) 178.45, 178.15, 162.57, 162.21, 160.18, 143.47, 141.34, 135.00, 131.98, 130.42, 128.35, 126.80, 126.72, 116.32, 114.90, 107.21, 55.29, 32.90. MS: (ESI) m/z 485.6 [M−H]$^-$ (Z)-5-((5-(4-(1H-tetrazol-5-yl)phenyl)-1H-pyrrol-2-yl)methylene)-1-((adamantan-1-yl)methyl)-2-thioxodihydropirimidine-4,6(1H,5H)-dione (15n)

Compound 15n was prepared from compound 14i and compound 3b. yield 72%. $^1$H-NMR (400 MHz, DMSO-d$^6$): δ (ppm) 8.21-8.19 (d, J=7.6 Hz, 2H), 8.044 (s, 1H), 8.041-8.02 (d, J=7.2 Hz, 2H), 7.59-7.58 (d, J=5.6 Hz, 1H), 7.32-7.31 (d, J=5.7 Hz, 1H), 1.89 (s, 3H), 1.63-1.59 (m, 8H), 1.52 (s, 6H). $^{13}$C-NMR (100 MHz, DMSO-d$^6$): δ (ppm) 179.96, 163.15, 143.18, 141.55, 131.94, 128.38, 126.67, 114.90, 114.68, 107.91, 107.46, 55.42, 41.50, 39.49, 39.29, 36.72, 28.31, 18.93. MS: (ESI) m/z 511.9 [M−H]$^-$.

(Z)-5-((5-(4-(2H-tetrazol-5-yl)phenyl)-1H-pyrrol-2-yl)methylene)-1-ally-2-thioxodihydropirimidine-4,6(1H,5H)-dione (15o)

Compound 15o was prepared from compound 14j and compound 3b. Yield 64%. $^1$H-NMR (400 MHz, DMSO-d$^6$): δ (ppm) 8.18-8.17 (d, J=7.2 Hz, 2H), 8.038 (s, 1H), 8.00-7.98 (d, J=7.6 Hz, 2H), 7.32-7.30 (d, J=8.4 Hz, 1H), 7.14-7.12 (d, J=8.2 Hz, 1H), 5.90-5.81 (m, 1H), 5.16-5.12 (dd, J=9.7 Hz, J$_2$=1.4 Hz, 2H), 5.01-4.99 (d, J=6.8 Hz, 1H), 4.92-4.91 (d, J=6.4 Hz, 1H). $^{13}$C-NMR (100 MHz, DMSO-d$^6$): δ (ppm) 178.50, 162.10, 156.11, 143.61, 141.33, 132.34, 131.93, 131.46, 128.22, 126.74, 125.28, 117.25, 114.85, 107.44, 107.00, 48.32. MS: (ESI) m/z 403.6 [M−H]$^-$.

(Z)-5-((5-(4-(1H-tetrazol-5-yl)phenyl)-1H-pyrrol-2-yl)methylene)-1-(pyridin-2-ylmethyl)-2-thioxodihydropirimidine-4,6(1H,5H)-dione (15p)

Compound 15p was prepared from compound 14k and compound 3b. yield 50%. $^1$H NMR: (400 MHz (CD$_3$)$_2$SO) δ (ppm) 8.43-8.41 (m, 1H), 8.16-8.08 (m, 4H), 7.98-7.96 (d, 2H, J=7.6 Hz), 7.72-7.68 (t, 1H, J=7.6 Hz), 7.26-7.22 (m, 3H), 5.60 (s, 2H). $^{13}$C NMR: (100 MHz (CD$_3$)$_2$SO) δ (ppm) 177.8, 172.6, 161.1, 157.1, 155.9, 150.9, 149.3, 137.1, 136.4, 135.5, 132.0, 128.0, 126.8, 124.8, 122.5, 121.0, 115.2, 114.5, 109.6, 57.5. MS: (ESI) m/z 454.6 [M−H]$^-$.

(Z)-4-(5-((4,6-dioxo-1-(pyridin-2-ylmethyl)-2-thioxotetrahydropyrimidin-5(2H)-ylidene)methyl)-1H-pyrrol-2-yl)-2-hydroxybenzoic Acid (15q)

Compound 15q was prepared from compound 14k and compound 4a. 50% of yield. $^1$H NMR: (400 MHz (CD$_3$)$_2$SO) δ (ppm) 8.55 (s, 1H), 8.21 (s, 1H), 7.94-7.90 (m, 2H), 7.52-7.26 (m, 6H), 5.70 (s, 2H). $^{13}$C NMR: (100 MHz (CD$_3$)$_2$SO) δ (ppm) 179.0, 178.7, 171.7, 162.6, 161.9, 161.3, 155.1, 147.6, 142.9, 141.7, 141.2, 139.1, 135.8, 132.0, 123.1, 121.8, 116.6, 115.4, 114.1, 113.8, 107.6, 50.2. MS: (ESI) m/z 446.6 [M−H]$^-$.

(Z)-5-((5-(3,5-difluoro-4-hydroxyphenyl)-1H-pyrrol-2-yl)methylene)-1-phenethyl-2-thioxodihydropyrimidine-4,6(1H,5H)-dione (15r)

Compound 15r was prepared from compound 14b and compound 3g. yield 82%. $^1$H-NMR (400 MHz, DMSO-d$^6$)

(ppm) 11.03 (bs, 1H), 8.18 (s, 1H), 7.58 (s, 2H), 7.36-7.23 (m, 7H), 4.58 (bs, 1H), 4.52-4.48 (t, 2H, J=7.6 Hz), 4.34 (bs, 1H), 2.97-2.93 (t, 2H, J=8.4 Hz,). $^{13}$C-NMR: (100 MHz, DMSO-d$^6$) δ (ppm) 178.3, 178.0, 162.3, 154.2, 151.8, 143.6, 140.7, 139.1, 138.8, 131.6, 128.9, 126.8, 120.1, 114.8, 109.1, 47.6, 33.0. MS: (ESI) m/z 452.0 [M–H]$^-$.

(Z)-5-((5-(4-(1H-tetrazol-5-yl)phenyl)-1-methyl-1H-pyrrol-2-yl)methylene)-1-phenethyl-2-thioxodihydropyrimidine-4,6(1H,5H)-dione (15s)

Compound 15s was prepared from compound 14b and compound 3f. The residue was purified by flash chromatography in DCM/MeOH 9:1. (yield 59%). $^1$H-NMR: (400 MHz, DMSO-d$^6$) δ (ppm) 12.34 (bs, 1H), 8.70-8.69 (m, 1H), 8.38-8.37 (m, 1H), 8.19-8.20 (d, 2H, J=8 Hz), 7.86-7.85 (d, 2H, J=8 Hz), 7.35-7.29 (m, 4H), 7.29-7.24 (m, 1H), 6.84-6.83 (m, 1H), 4.51-4.47 (m, 2H), 3.90 (s, 3H), 2.95-2.93 (m, 2H). $^{13}$C-NMR: (100 MHz, DMSO-d$^6$) (ppm) 178.4, 162.9, 161.5, 159.9, 159.1, 155.8, 147.6, 139.9, 138.9, 133.0, 130.6, 128.9, 127.7, 126.8, 125.7, 115.5, 107.9, 47.8, 47.3, 33.1. MS: (ESI) m/z 482.0 [M–H]$^-$.

Example 5

5-((5-(2-chloro-5-(trifluoromethyl)phenyl)-1H-pyrrol-2-yl)methylene)-2-thioxodihydropyrimidine-4,6(1H,5H)-dione (17a)

(yield 83%) orange solid, $^1$H NMR: (400 MHz (CD$_3$)$_2$SO) δ (ppm) 12.41 (s, 1H), 12.36 (s, 1H), 8.15 (s, 1H), 8.10 (s, 1H), 7.82 (d, 1H, J=8.4 Hz), 7.75 (d, 1H, J=8.4 Hz), 7.56 (bs, 1H), 7.19 (s, 1H); $^{13}$C NMR: (101 MHz (CD$_3$)$_2$SO) δ (ppm) 178.00, 163.15, 162.53, 139.09, 134.96, 131.13, 129.78, 129.22, 128.90, 127.71, 127.47, 125.17, 122.46, 116.99, 108.52 ppm. MS: (ESI) m/z 397.7 [M–H]$^-$

4-(5-((4,6-dioxo-2-thioxotetrahydropyrimidin-5(2H)-ylidene)methyl)-1H-pyrrol-2-yl)-2-hydroxybenzoic Acid (17b)

(yield 63%) red solid, $^1$H NMR: (400 MHz (CD$_3$)$_2$SO) δ (ppm) 12.41 (bs, 1H), 12.36 (bs, 1H), 8.15 (s, 1H), 7.90 (d, 1H, J=8.4 Hz), 7.58 (bs, 1H), 7.33 (d, 1H, J=9.2 Hz), 7.25 (s, 1H) ppm. $^{13}$C NMR: (101 MHz (CD$_3$)$_2$SO) δ (ppm) 177.92, 171.71, 163.12, 162.62, 142.18, 140.62, 140.17, 139.60, 135.98, 131.63, 116.48, 115.03, 113.92, 113.52, 107.99, 104.90 ppm. MS: (ESI) m/z 355.8 [M–H]$^-$

Example 6

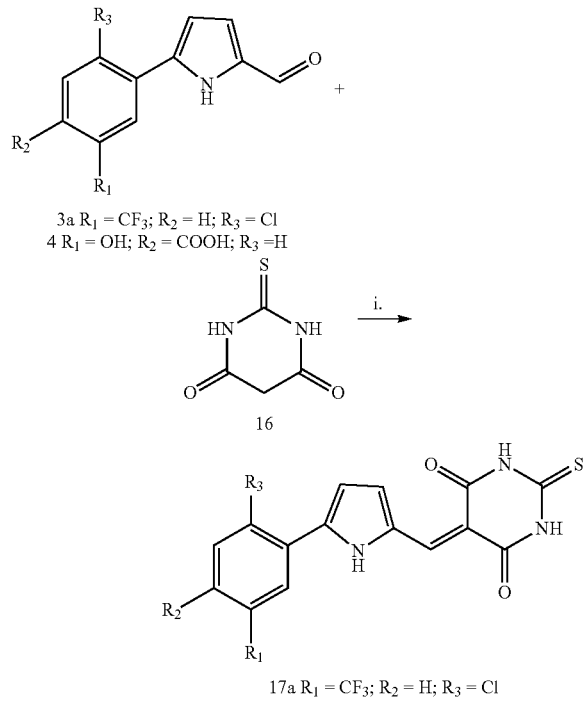

Scheme 5. Synthesis of unsubstituted thiobarbituric compounds 17a-b

3a R$_1$ = CF$_3$; R$_2$ = H; R$_3$ = Cl
4 R$_1$ = OH; R$_2$ = COOH; R$_3$ = H

16

17a R$_1$ = CF$_3$; R$_2$ = H; R$_3$ = Cl
17b R$_1$ = OH; R$_2$ = COOH; R$_3$ = H i. HCl, EtOH, 70° C., 12 h.

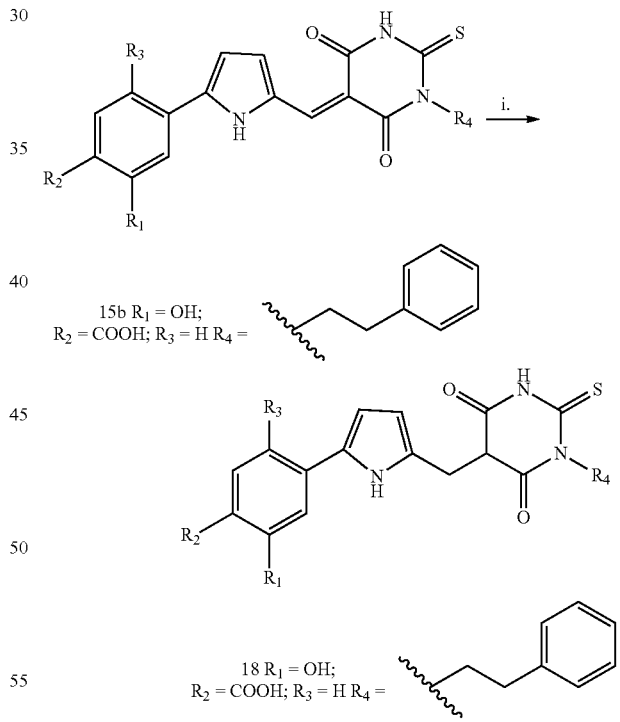

Scheme 6. Synthesis of reduced thiobarbituric compound 18

15b R$_1$ = OH; R$_2$ = COOH; R$_3$ = H R$_4$ =

18 R$_1$ = OH; R$_2$ = COOH; R$_3$ = H R$_4$ = i. NaBH$_4$, EtOH, rt, 30 min.

General Procedure for the Synthesis of Compounds 17a and 17b: The opportune aldehyde 3a or 4a (0.22 mmol, 1 eq) and thiobarbituric acid (0.22 mmol, 1 eq) were suspended in EtOH (6 mL), to this, 3 drops of HCl (conc.) were added, and the mixture was stirred at 70° C. overnight. After this time 3 mL of HCl were added, and the resulting precipitate was filtered at reduced pressure, to give a solid that was washed with H$_2$O, CH$_3$OH and hexane.

4-(5-((hexahydro-4,6-dioxo-1-phenethyl-2-thioxopyrimidin-5-yl)methyl)-1H-pyrrol-2-yl)-2-hydroxybenzoic Acid (18)

To a suspension of compound 15b (0.10 mmol, 1 eq) in EtOH (3 mL), NaBH$_4$ (0.31 mmol, 3 eq) was added and the reaction mixture stirred at room temperature for 30 minutes.

The reaction mixture was concentrated under reduced pressure. H$_2$O (0.450 mL) and HCl (1N) until pH≈2 were added. The precipitate was filtered and washed with H$_2$O and MeOH. The resulting residue was finally crystallized from MeOH to give compound 18 as a grey solid. Yield: 67%. $^1$H NMR: (400 MHz (CD$_3$)$_2$CO) δ (ppm) 11.18 (bs, 1H), 11.12 (bs, 1H), 10.39 (bs, 1H), 10.29 (bs, 1H), 7.77 (d, 2H, J=8 Hz), 7.31-7.05 (m, 7H), 6.59 (s, 1H), 5.93 (s, 1H), 4.58-4.56 (m, 3H), 4.48-4.33 (m, 2H), 3.71-3.49 (m, 2H), 2.85-2.84 (m, 2H). $^{13}$C NMR: (101 MHz (CD$_3$)$_2$CO) δ (ppm) 180.0, 171.6, 167.5, 165.9, 162.8, 140.1, 138.4, 131.1, 130.8, 128.7, 128.6, 126.4, 114.5, 110.2, 109.0, 108.8, 98.9, 93.1, 50.6, 47.4, 32.7, 26.7. MS: (ESI) m/z 462.6 [M−H]$^-$ Example 7

5-(4-iodophenyl)-1H-tetrazole (2b)

4-iodobenzonitrile (2.62 mmol, 1 eq) was dissolved in dry DMF (6 ml), NaN$_3$ (2.88, 1.10 eq) and NH$_4$Cl (2.88 mmol, 1.10 eq) were added and stirred at 100° C. for 22 h. The reaction mixture was concentrated under reduced pressure. The crude product was purified by trituration in DCM to provide compound 2b as a yellow solid. Yield: 84%. $^1$H NMR: (400 MHz (MeOD) δ (ppm) 7.90 (d, 2H, J=8.4 Hz), 7.75 (d, 2H, J=8.4 Hz). MS: (ESI) m/z 270.6 [M−H]$^-$ Example 8

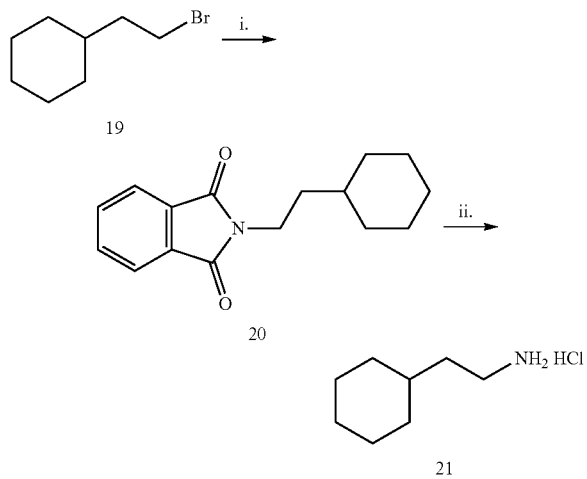

i. potassium phthalimide, DMF, rt, 48 h.
ii. a) hydrazine monohydrate, EtOH, rt, 30 min,
   b) HCl 3N, rt, 10 min.

2-(2-cyclohexylethyl)isoindoline-1,3-dione (20)

To a solution of 1-Bromo-2-cyclohexylethane (1.05 mmol, 1 eq) in dry DMF (3 mL), potassium phthalimide (1.15 mmol, 1.10 eq) was added. The reaction mixture was stirred at rt for 48 h. The reaction mixture was diluted with H$_2$O (20 ml) and extracted with EtOAc (3×15 ml). The organic phase was washed with LiCl (2×50 ml) and dried over Na$_2$SO$_4$. The solvent was removed at reduced pressure. Yield: 97%. $^1$H NMR: (400 MHz CDCl$_3$) δ (ppm) 7.81-7.80 (m, 2H), 7.68-7.66 (m, 2H), 3.69-3.65 (t, 2H, J=7.6 Hz), 1.78-1.75 (m, 1H), 1.73-1.71 (m, 4H), 1.62-1.59 (m, 2H), 1.23-1.18 (m, 4H), 0.96-0.88 (m, 2H), MS: (ESI) m/z 297 [M+K+H]$^+$.

2-cyclohexylethan-1-amine chlorohydrate (21)

A mixture of 2-(2-cyclohexylethyl)isoindoline-1,3-dione (2.87 mmol, 1 eq) and hydrazine monohydrate (2.87 mmol, 1 eq) was refluxed for 3 h. HCl 3 N was added until pH=2 and the precipitate filtered off. The trituration with Et$_2$O accomplished 2-cyclohexylethan-1-amine chlorohydrate in quantitative yield. $^1$H NMR: (400 MHz MeOD) δ (ppm) 2.94-2.90 (m, 2H), 1.74-1.71 (m, 5H), 1.65-1.49 (m, 2H), 1.37-1.26 (m, 4H), 1.10-0.95 (m, 2H). MS: (ESI) m/z 128.1 [M+H]$^+$.

Biology
Cells

African green monkey fibroblastoid kidney cells (Vero) (ATCC CCL-81), human epithelial carcinoma cells (Hep-2) (ATCC CCL-23), African green monkey kidney epithelial cells (MA-104) (ATCC CRL-2378.1) were grown as monolayers in Eagle's minimal essential medium (MEM) (Gibco/BRL, Gaithersburg, MD) supplemented with 10% heat inactivated fetal calf serum (FCS) and 1% antibiotic-antimycotic solution (Zell Shield, Minerva Biolabs GmbH, Berlin, Germany). Low-passage human embryonic lung fibroblasts (HELFs) (ATCC CCL-199) were grown as monolayers in Eagle's minimal essential medium (Gibco-BRL) in the same conditions as described above with the addition of 1 mM sodium pyruvate.

Human epithelial adenocarcinoma HeLa cells (ATCC CL-2) and Huh-7 cells (provided by Apath, LLC) were propagated in Dulbecco's modified Eagle's medium (DMEM) supplemented as described above.

The 293TT cell line derived from human embryonic kidney cells transformed with the simian virus 40 (SV40) large T antigen (NCI E-120-2008/0-162), was cultured as monolayer in medium in DMEM supplemented as described above plus Glutamax-I (Invitrogen, Carlsbad, CA) and non-essential aminoacids.

Viruses

HSV-1 and HSV-2 strains 54 (Donalisio et al, 2016) were kindly provided by Prof. M. Pistello, University of Pisa, Italy. Said HSV-1 and HSV-2 strains 54 were propagated and titrated by plaque assay on Vero cells. A HSV-2 strain with phenotypic resistance to acyclovir was generated by serial passage in the presence of increasing concentrations of acyclovir, as previously described (Donalisio M, Nana H M, Ngane R A N, Gatsing D, Tchinda A T, Rovito R, et al. In vitro anti-Herpes simplex virus activity of crude extract of the roots of Nauclea latifolia Smith (Rubiaceae). BMC Complement Altern Med. 2013; 13:266. https://doi.org/10.1186/1472-6882-13-266 PMID: 2413191618.).

HCMV strain Towne was kindly provided by Prof. W. Brune, Heinrich Pette Institut, Hamburg, Germany (V. Cagno et al., In vitro evaluation of the antiviral properties of Shilajit and investigation of its mechanisms of action. J Ethnopharmacol. 166, 129-134 (2015)); it was propagated and titrated by plaque assay on HELF cells.

RSV strain A2 (ATCC VR-1540) was propagated in Hep-2 and titrated by the indirect immunoperoxidase staining procedure using an RSV monoclonal antibody (Ab35958; Abcam, Cambridge, United Kingdom), as described previously (Cagno et al, 2014).

Human rotavirus (HRoV) strain Wa (ATCC VR-2018) was activated with 5 mg/ml porcine pancreatic trypsin type IX (Sigma, St. Louis, Mo.) for 30 min at 37° C. and propagated in MA104 cells using MEM containing 0.5 mg trypsin per ml, as described previously (Civra et al, 2015).

VSV (ATCC® VR-1238™) was propagated on Vero cells and titrated by plaque assay. Adenovirus 5 encoding GFP (GFP-Ad5), with a E1/E3 deletion, was purchased from Vector Biolabs (Biolabs 1060, Philadelphia, PA, USA). HPV-16 pseudovirions were produced with 293TT as previously described (V. Cagno et al., The agmatine-containing poly(amidoamine) polymer AGMA1 binds cell surface heparan sulfates and prevents attachment of mucosal human papillomaviruses. Antimicrob. Agents Chemother. 59, 5250-5259 (2015)) and their concentration was assessed on Hela cells. Virus stocks were maintained at −80° C.

Zika virus (PRVABC59) was kindly provided by Prof Marco Alves (Pfaender et al, 2017) and was propagated and titrated by plaque assay on Vero cells.

Dengue virus (ATCC® VR-1584™) was propagated and titrated by plaque assay on Huh-7 cells.

H1N1 was isolated from a clinical specimen and was propagated and titrated on MDCK cells (ATCC® CCL-34™)

Cell Viability

Cell viability was measured using the MITS [3-(4,5-dimethylthiazol-2-yl)-5-(3 carboxy methoxy phenyl)-2-(4-sulfophenyl)-2H-tetrazolium] assay. Cell cultures were seeded in 96-well plates and were incubated with different concentrations of compounds of the invention in triplicate under the same experimental conditions described for the antiviral assays. Cell viability was determined using the CellTiter 96 Proliferation Assay Kit (Promega, Madison, WI, USA) according to the manufacturer's instructions. Absorbances were measured using a Microplate Reader (Model 680, BIORAD) at 490 nm. The effect on cell viability at different concentrations of the compound was expressed as a percentage, by comparing absorbances of treated cells with those of cells incubated with culture medium and equal volumes of vehicle. The 50% cytotoxic concentrations ($CC_{50}$) and 95% confidence intervals (CIs) were determined using Prism software (Graph-Pad Software, San Diego, CA).

Antiviral Assays

HSV, VSV and ZIKA Virus Inhibition Assays

The effect of compounds on HSV, VSV and ZIKA virus (ZikaV) infection was evaluated by plaque reduction assay. Vero cells were pre-plated 24 h in advance in 24-well plates at a density of $10^5$ cells. Concentrations of compounds ranging from 50 μM to 0.0001 μM in DMSO were mixed with HSV-2 (MOI 0.001 pfu/cell) or HSV-2 acyclovir resistant (HSV-2 Acy R) (MOI 0.001 pfu/cell) or HSV-1 (MOI 0.0005 pfu/cell) or VSV (MOI 0.005 pfu/cell) or ZIKAV (MOI 0.001 pfu/cell) and incubated for 1 hour at 37° C. The mixtures were subsequently added to the cells, which were then incubated at 37° C. for 2 h. The virus inoculum was then removed and the cells washed and overlaid with a medium containing 1.2% methylcellulose (Sigma). After further incubation at 37° C. for 24 h (HSV-2 and VSV) or 48 h (HSV-1), or 72 h (ZikaV), cells were fixed and stained with 0.1% crystal violet in 20% ethanol and viral plaques counted. The effective concentration producing 50% reduction in plaque formation (EC50) and the effective concentration producing 90% reduction in plaque formation (EC90) were determined using Prism software by comparing drug-treated wells with wells treated with medium and DMSO. The selectivity index (SI) was calculated by dividing the CC50 by the EC50 value.

DENV Virus Inhibition Assays

The effect of compounds on DENV infection was evaluated by plaque reduction assay. Huh-7 cells were pre-plated 24 h in advance in 24-well plates at a density of $10^5$ cells. Concentrations of compounds ranging from 50 μM to 0.0001 μM in DMSO were mixed with DENV-2 (MOI 0.01 pfu/cell) and incubated for 1 hour at 37° C. The mixtures were subsequently added to the cells, which were then incubated at 37° C. for 2 h. The virus inoculum was then removed and the cells washed and overlaid with a medium containing 1.2% methylcellulose (Sigma). After further incubation at 37° C. for 72 h cells were fixed and stained with 0.1% crystal violet in 20% ethanol and viral plaques counted. The effective concentration producing 50% reduction in plaque formation (EC50) were determined using Prism software by comparing drug-treated wells with wells treated with medium and DMSO. The selectivity index (SI) was calculated by dividing the CC50 by the EC50 value.

HCMV Inhibition Assays

HELF cells were pre-plated in a 96-well plate. The following day concentrations of compounds ranging from 50 μM to 0.0001 μM in DMSO were mixed with HCMV (MOI 0.005 pfu/cell) and incubated for 1 hour at 37° C. The mixtures were subsequently added to the cells, which were then incubated at 37° C. for 3 h; monolayers were then washed and overlaid with 1.2% methylcellulose medium supplemented with 3% FCS and 1 mM sodium pyruvate. After five days incubation, cells were observed under an inverted Zeiss LSM510 fluorescence microscope (Zeiss, Oberkochen, Germany) and the EC50 were calculated by comparing GFP positive cells in treated and untreated wells. The effective concentration producing 50% reduction in plaque formation (EC50) was determined using Prism software. The selectivity index (SI) was calculated by dividing the CC50 by the EC50 value.

RSV Inhibition Assays

Hep-2 cells were pre-plated in a 96-well plate. The following day concentrations of compounds ranging from 50 μM to 0.0001 μM in DMSO were mixed with RSV (MOI 0.005 pfu/cell) and incubated for 1 hour at 37° C. The mixtures were subsequently added to the cells, which were then incubated at 37° C. for 3 h; monolayers were then washed and overlaid with 1.2% methylcellulose medium. 72 hours later cells were fixed and subjected to specific immunostaining using an RSV monoclonal antibody (Ab35958; Abcam, Cambridge, United Kingdom) in order to visualize syncytia. EC50 were calculated by comparing numbers of syncytia in treated and untreated wells. The effective concentration producing 50% reduction in plaque formation (EC50) was determined using Prism software. The selectivity index (SI) was calculated by dividing the CC50 by the EC50 value.

HRoV Inhibition Assays

MA104 cells were pre-plated in 96-well trays. The following day virus infectivity was activated by adding 5 μg porcine trypsin (Sigma)/ml for 30 min at 37° C. Concentrations of compounds ranging from 50 μM to 0.0001 μM in DMSO were mixed with HRoV (MOI 0.02 pfu/cell) and incubated for 1 hour at 37° C. The mixtures were subsequently added to the cells, which were then incubated at 37° C. for 1 h; monolayers were then washed and overlaid with MEM. After 16 h, cells were fixed with cold acetone-methanol and viral titers were determined by indirect immunostaining using the monoclonal antibody mab-0036 (specific for human 41 kDa inner capsid protein—VP6—of rotavirus) purchased from Covalab (Villeurbanne, France) and the UltraTech HRP Streptavidin-Biotin Detection System (Beckman Colter). The percentages of infection were calculated comparing the number of infected cells in treated wells with the one in untreated wells. The EC50 was calculated by non linear regression analysis with Prism 7 (GraphPad). The effective concentration producing 50% reduction in plaque formation (EC50) was determined using Prism software. The selectivity index (SI) was calculated by dividing the CC50 by the EC50 value.

HPV-16 and Ad5 Inhibition Assays

HeLa cells were pre-plated in 96-well plates. The following day, concentrations of compounds ranging from 50 µM to 0.0001 µM in DMSO were mixed with HPV-16 (approximately 1 ng/ml Li according to WB quantification comparing band intensity of Li and BSA) or Ad5 (MOI 0.02 pfu/cell) and incubated for 1 hour at 37° C. The mixtures were subsequently added to the cells, which were then incubated at 37° C. for 72 h. The GFP-expressing infected cells were observed under an inverted Zeiss LSM510 fluorescence microscope (Zeiss, Oberkochen, Germany) and the EC50 were calculated by comparing GFP positive cells in treated and untreated wells by non linear regression analysis with Prism 7 (GraphPad). The effective concentration producing 50% reduction in plaque formation (EC50) was determined using Prism software. The selectivity index (SI) was calculated by dividing the CC50 by the EC50 value.

H1N1 Inhibition Assays

MDCK cells were pre-plated in 96-well plates. The following day, concentrations of compounds ranging from 50 µM to 0.0001 µM in DMSO were mixed with H1N1 (MOI 0.05 pfu/cell) and incubated for 1 hour at 37° C. The mixtures were subsequently added to the cells for 1 h at 37° C., after a washout, cells were overlaid with MEM for 16 h at 37° C. Cells were then fixed and subjected to specific immunostaining using a Flu A monoclonal antibody (Merck 5001) in order to visualize infected cells. EC50 were calculated by comparing numbers of infected cells in treated and untreated wells. The effective concentration producing 50% reduction in plaque formation (EC50) was determined using Prism software. The selectivity index (SI) was calculated by dividing the CC50 by the EC50 value.

HIV-1 Inhibition Assays

The human TZM-bl indicator cell line (obtained from the NIH AIDS reagents program, cat. Nr 8129, www.aidsreagent.org) was maintained at 37° C. and 5% CO2 in Dulbecco's modified Eagle's medium (DMEM) medium containing 10% fetal bovine serum, 50 µg/ml penicillin, and 50 µg/ml streptomycin. The HIV-1 laboratory strains NL (AD8) (NIH AIDS reagents program, cat. Nr, 11346) and NL4.3 (NIH AIDS reagents program, cat. Nr. 114) were titrated as previously reported by Tiberi et al (2014). Briefly, serial 5-fold dilutions of each virus were made in quadruplicate wells in 96-well culture plates, in a total volume of 100 µl of growth medium (DMEM), for a total of 8 dilution steps. Freshly trypsinized cells (20,000 cells in 100 µl of growth medium containing 75 µg/mL DEAE-dextran) were added to each well, and the plates were incubated at 37° C. in a humidified 5% $CO_2$-95% air environment. After 48 h of incubation, the medium was removed and viral infection was quantified using a β-galactosidase (CPRG) assay (Roche). Twenty thousand TZM-bl cells/well were seeded in 96-well plates in complete DMEM supplemented with 30 µg/ml DEAE-dextran (Sigma-Aldrich). Three hundred times the 50% tissue culture infective dose (TCID50)/ml of each strain was pretreated for 1 h at 37° C. with six serial dilutions (10000 nM, 2000 nM, 400 nM, 80 nM, 16 nM, 3.2 nM) and then added to the cells. Vehicle (0.1% dimethyl sulfoxide [DMSO])-treated cells served as a negative control. A CCR5 inhibitor (maraviroc, Mar, Sigma Aldrich catalogue number: PZ0002) and an integrase inhibitor (raltegravir, Ral, Sigma Aldrich catalogue number: CDS023737) were used as positive-control agents. After 2 days, viral infection was quantified using a CPRG assay (Roche cat nr 11379119103). The inhibitory curves were fitted by nonlinear regression, allowing for the calculation of the 50% effective concentration (EC50) using the Prism software. To evaluate the cell toxicity of the compounds, the metabolic XTT [2,3-bis-(2-methoxy-4-nitro-5-sulfophenyl)-2H-tetrazolium-5-carboxanilide] test (Sigma-Aldrich) was performed according to the manufacturer's instructions.

Data Analysis

All results are presented as the mean values from three independent experiments. The $EC_{50}$ and $EC_{90}$ values for inhibition curves were calculated by regression analysis using the software GraphPad Prism (GraphPad Software, San Diego, California, U.S.A.) by fitting a variable slope-sigmoidal dose-response curve. For binding and entry assays the significance was analyzed with a One-way Anova followed by a Bonferroni.

Example 9

Antiviral Activity

Selected compounds were tested against several enveloped viruses.

The antiviral potencies and toxicity of the most active compounds are summarized in the Tables 1-6 below. It is important to note that compounds of invention inhibit the replication of different enveloped viruses such as HIV-1, HSV-1, HSV-2 HSV-2 Acy R, HCMV, RSV, VSV, H1N1, ZikaV and DENV-2 but are ineffective against not enveloped viruses such as HPV-16, Ad5, HRoV.

TABLE 1

Antiviral and cytotoxic activity of selected compounds against HIV-1 infected cells.

| Compound | HIV Strain AD8 $EC_{50}$ (nM)$^a$ | HIV Strain NL4-3 $EC_{50}$ (nM)$^a$ | Cytotoxicity (TZM-bl cells) $CC_{50}$ (µM) |
|---|---|---|---|
| 15a | 290 | 217 | >20 |
| 15b | 251 | 64 | >20 |
| 7b | 532 | nt | >20 |
| 17a | 3200 | nt | >20 |
| 17b | 76 | 160 | >20 |
| Mar | 36.7 | >20000 | >20 |
| Ral | 6.5 | 21 | >20 |

*EC50 half maximal effective concentration
†CC50 half maximal cytotoxic concentration
nt: not tested

TABLE 2

Antiviral activity against HSV-2 infected cells

| Compound | EC50* (nM) | EC90° (nM) | CC50† (µM) | SI‡ |
|---|---|---|---|---|
| 17b | 698 | 7469 | >300 | >429.8 |
| 15b | 86.9 | 1190 | >300 | >3452 |
| 15c | 209.5 | 618 | >300 | >1435 |
| 15d | 34480 | 88200 | >300 | >8.7 |
| 18 | 712 | 128 | >300 | >417.2 |

*EC50 half maximal effective concentration
°EC90 90% effective concentration
†CC50 half maximal cytotoxic concentration
‡SI selectivity index

TABLE 3

Antiviral activity against ZIKAV infected cells

| Compound | EC50* (nM) | EC90° (nM) | CC50† (μM) | SI‡ |
|---|---|---|---|---|
| 15b | 43.3 | nt | >111 | >2563 |
| 15c | 25.8 | 365 | >300 | >12000 |
| 15d | 1110 | 26610 | >300 | >272.7 |
| 18 | 35.3 | 308 | >300 | >849.8 |

*EC50 half maximal effective concentration
°EC90 90% effective concentration
†CC50 half maximal cytotoxic concentration
‡SI selectivity index
nt: not tested

TABLE 4

Antiviral activity against H1N1 infected cells

| Compound | EC50* (nM) | EC90° (nM) | CC50† (μM) | SI‡ |
|---|---|---|---|---|
| 15b | 1241 | 3880 | >300 | >77 |
| 15c | 793 | 1760 | >300 | >379 |
| 15d | 25000 | 372000 | >300 | >12 |
| 18 | 1260 | 14900 | >300 | >238 |

*EC50 half maximal effective concentration
°EC90 90% effective concentration
†CC50 half maximal cytotoxic concentration
‡SI selectivity index

TABLE 5

15b spectrum of antiviral activity against enveloped and non-enveloped viruses

| Type of virus | Virus | EC50* (nM) | EC90° (nM) | CC50† (μM) | SI‡ |
|---|---|---|---|---|---|
| Enveloped | HSV-2 Acy R | 83.4 | 420 | >300 | >3597 |
|  | HSV-1 | 454 | 3716 | >300 | >660.8 |
|  | HCMV | 118 | 772 | 36.3 | 308.7 |
|  | RSV | 315 | 1509 | 241 | 765 |
|  | VSV | 144 | 2169 | >300 | >2631 |
|  | H1N1 | 1241 | 3880 | >300 | >77 |
|  | ZKV | 43.3 | nt | >111 | >2563 |
| Non enveloped | HPV-16 | n.a. | n.a. | >300 | n.d. |
|  | Ad5 | n.a. | n.a. | >300 | n.d. |
|  | HRoV | n.a. | n.a. | >300 | n.d. |

*EC50 half maximal effective concentration
°EC90 90% effective concentration
†CC50 half maximal cytotoxic concentration
na: not active
nd: not determined
nt: not tested

TABLE 6

Antiviral activity against DENV-2 infected cells

| Compound | EC50* (μM) | CC50† (μM) | SI‡ |
|---|---|---|---|
| 15b | 1.4 | 7.9 | 5.6 |
| 15c | 3.4 | 70 | 20.6 |
| 15f | 7.8 | 28 | 3.6 |
| 15p | 12.2 | 89 | 7.3 |

*EC50 half maximal effective concentration
†CC50 half maximal cytotoxic concentration
‡SI selectivity index Study of Mechanism of Action
Vero Cells were Subjected to Different Assays:
Pretreatment:

Vero Cells were pretreated for 2 h at 37° C. with increasing concentrations of compound 15b in DMSO the inocula were then removed cells washed and HSV-2 was added on cells for 2 h at 37° C. Subsequently the same protocol described above for the evaluation of HSV inhibition was followed.

During infection cells were subjected to the same experiment described above for the evaluation of HSV inhibition without the preincubation between compounds and virus.

Post Treatment:

Vero cells were infected with HSV-2 (MOI 0.01 pfu/cell) for 2 h at 37° C., the viral inoculum was removed, and cultures were exposed to increasing concentrations of 15b in DMSO and incubated until control cultures (HSV-2 infected Vero cells without 15b) displayed extensive cytopathology. Supernatants and cells were harvested and cell free virus infectivity titers were determined in duplicate by plaque assay in Vero cell monolayers. Percent inhibition was determined by comparing the titer measured in the presence of the compounds to that measured in untreated wells.

Binding of Virus to Cell:

Vero Cells were plated in 96 well plates. The following day 10 μM of compound 15b in DMSO and HSV-2 (MOI 10 pfu/cell) were incubated for 1 h at 37° C. and subsequently added on cells for 2 hours at 4° C. Cells were then fixed with 4% paraformaldehyde, air dried, and blocked with 5% bovine serum albumin (BSA) in phosphate-buffered saline (PBS)-Tween. Binding of virus to vero cells was detected using the polyclonal HSV-2 antibody (Dako, Denmark) (diluted 1:250) incubated for 1 h at room temperature, washed three times with PBS-Tween, and incubated for 1 h at 37° C. with anti-rabbit conjugated to horseradish peroxidase (1:500). At the end of incubation, plates were washed three times with PBS-Tween, ABTS[2,2-azinobis(3-ethyl benz thiazoline sulfonic acid)] (A1888 SIGMA ALDRICH) substrate was added for 30 minutes (Thermo Scientific, Rockford, IL), and the absorbance at 405 nm was read.

Entry of Virus into Cell:

Cells were plated in 96 well plates. The following day 10 μM of compound 15b in DMSO and HSV-2 (MOI 10 pfu/cell) were incubated for 1 h at 37° C. and subsequently added on cells for 1 hour at 4° C. Cells were then washed and shifted at 37° C. for 1 h and 30 minutes. Cells were then fixed with 4% paraformaldehyde, air dried and permeabilized with PBS-TRITON (0.5%) and then the same protocol described for binding was followed.

Figure 2:
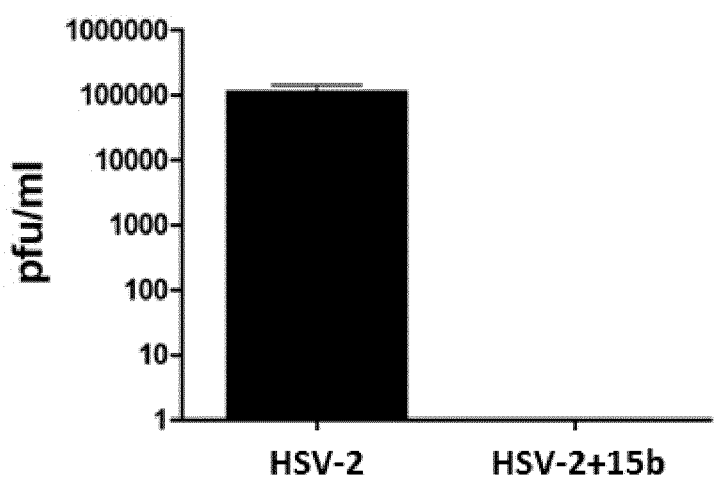
FIG. 2: Virucidal activity of compound 15b against HSV-2, expressed as pfu (Plaque Forming Units) per mL.

Virucidal Assay:

Approximately 105 PFU of HSV2 plus 10 μM of 15b in DMSO were added to MEM and mixed in a total volume of 100 μl. The virus-compound mixtures were incubated for 2 h at 37° C. then diluted serially to the non-inhibitory concentration of test compound; the residual viral infectivity was determined by viral plaque assay (FIG. 2).

Immunofluorescence

Vero cells were pre-plated on coverslips and the following day the binding or entry protocol described above was applied. Cells were then fixed with 4% paraformaldehyde, air dried and for entry protocol permeabilized with PBS-TRITON. Blocking was performed with PBS-BSA1% for 1 h at room temperature and subsequently HSV-2 polyclonal antibody (B011402-2 Dako) (1:250) was added on cells, after 1 hour at 37° C. the inoculum was removed and coverslips were washed with PBS-TWEEN for 3 times. Rhodamine conjugated anti-rabbit IgG (Santa Cruz) was then added on cells for 1 h at 37° C. following 3 washes coverslips were mounted on microscope glasses and observed with Zeiss LSM510 fluorescence microscope (Zeiss, Oberkochen, Germany) and images were acquired (FIG. 3A, 3B).

Determination of the Lipid Oxidation Capability

To evaluate the lipid oxidation capability of 15b, a lipoperoxidation test was carried out. In lipid peroxidation, free radicals attack double bonds of polyunsaturated fatty acids forming lipid hydroperoxides, which undergo homolytic scission to form a variety of cytotoxic compounds, such as aldehydes. This oxidative stress plays an important role in damaging membrane lipids.

The effect of 15b was evaluated toward the oxidation of linoleic acid, incorporated in DPPC liposomes, using TBA assay. The assay is based on the reactivity of malondialdehyde (MDA), a colorless end-product of degradation, with 2-thiobarbituric acid (TBA) to produce a pink adduct (TBA-MDA-TBA) that absorbs at 535 nm. MDA is indeed one of the final products of polyunsaturated fatty acids peroxidation in the cells and is considered an indicator of lipid peroxidation. MDA was detected spectrophotometrically according to methods described in literature (Boon-Huat Bay, Yuan-Kun Lee, Benny Kwong-Huat Tan, Eng-Ang Ling, Lipid peroxidative stress and antioxidative enzymes in brains of milk-supplemented rats, Neuroscience Letters 277 (1999) 127-130).

15b was incubated at 37° C. for 2 h with a 0.5% linoleic acid containing liposome aqueous dispersion (Cagno, V.; Tintori, C.; Civra, A.; Cavalli, R.; Tiberi, M.; Botta, L.; Brai, A.; Poli, G.; Tapparel, C.; Lembo, D.; et al. Novel Broad Spectrum Virucidal Molecules against Enveloped Viruses. 2018). Then, a sample (0.2 mL) was withdrawn and introduced in a glass tube closed with a screw cap and added with 0.1 mL of water, 0.2 mL of 4% w/w SDS, 1.5 mL of 1.0% w/w phosphoric acid and 1.0 mL of 0.6% w/w TBA (T5500 SIGMA-ALDRICH). The mixture was stirred and heated in water bath at 95-100° C. for 45 min to favor the formation of the complex. After cooling in an ice bath, 4.0 mL of 1-butanol were added to each tube and the TBA-MDA-TBA complex was extracted upon stirring and centrifugation. The organic supernatant was evaluated by spectrophotometry.

Figure 4:
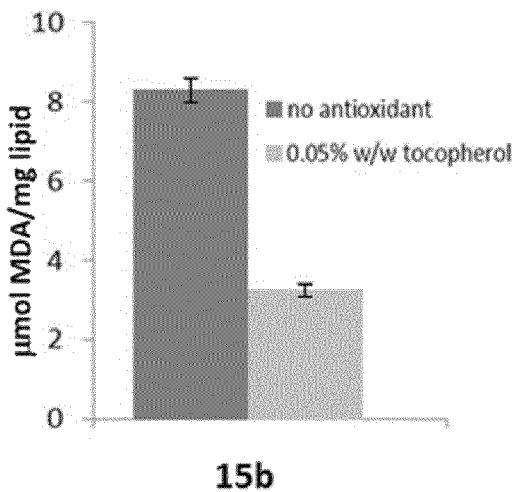
FIG. 4: Oxidative activity of 15b on DPPC liposomes. Malondialdehyde (MDA) (micromoles/mg lipid) produced from linoleic acid oxidation in the presence and in the absence of tocopherol as antioxidant agent.

The calibration curve of TBA-MDA-TBA complex was obtained using a MDA precursor 1,1,3,3-tetraethoxypropane. MDA can be obtained by acid hydrolysis from 1,1,3,3-tetraethoxypropane in an equimolecular reaction. For this purpose, standard solutions of 1,1,3,3-tetraethoxypropane in SDS (4% w/w) within the concentration range 5-250 μM were prepared. The solutions were subjected to TBA assay and analyzed at spectrophotometer. The final concentration of MDA derived from the reaction of linoleic acid, calculated exploiting the calibration curve, was expressed as micromoles of MDA per mg of lipid substrate. The same experiment was carried out in the presence of 0.05% w/w of tocopherol (T3251 SIGMA ALDRICH) as antioxidant, to confirm the oxidant mechanism of compound 15b (FIG. 4).

Discussion

The present results clearly demonstrate that compounds of the present invention show a good inhibitory activity against enveloped viruses such as HIV-1, HSV-1, HSV-2, HSV-2 Acy R, HCMV, RSV, VSV, H1N1, ZKV and DENV-2. Compounds are completely inactive against non-enveloped viruses (HPV-16, Ad5, HRoV) (Table 5).

In particular, as shown in Tables 1-4 compounds of the present invention possess potent activities against HIV-1 AD8 and NL4-3 strains, ranging from 64 nM to 3.2 μM, anti HSV-2 activities ranging from 87 nM to 34 μM, anti-ZIKAV activities ranging from 25.8 nM to 1.1 μM, anti Flu activities (H1N1 strain) ranging from 0.7 to 25 μM, anti DENV-2 activities ranging from 1.4 to 12.2 μM.

Further several assays were performed to better understand the mechanism of action of the present compounds against enveloped viruses.

In order to determine if the antiviral activity of the compounds of the invention is due to an interaction with the host cells, compound 15b was added on vero cells before the virus (pre-incubation or pre-treatment assay). Further, the virus and the compound were added on the cells without pre-incubation. The results in FIG. 1 demonstrate that the antiviral activity of the compounds is not due to an interaction with the host cells, since compound 15b is inactive in pre-treatment assays while there was a significant reduction of antiviral activity in the during infection assay (15b EC50 7.89 μM). This data confirms that compound 15b acts via an oxidative mechanism, with a competition between oxidation of lipids in the viral envelope and in the cell membrane for the insertion and activity of compounds.

To further elucidate the mechanism of action, the inventors performed a virucidal assay in which 15b was incubated with the virus at 10 μM concentration; subsequently, the mixture was titrated on cells and the residual infectivity was evaluated only at dilutions at which the compound was no more active (FIG. 2). In these conditions it was possible to observe that the viral infectivity in presence of compounds was never regained, indicating an irreversible mechanism of action.

Figure 3:
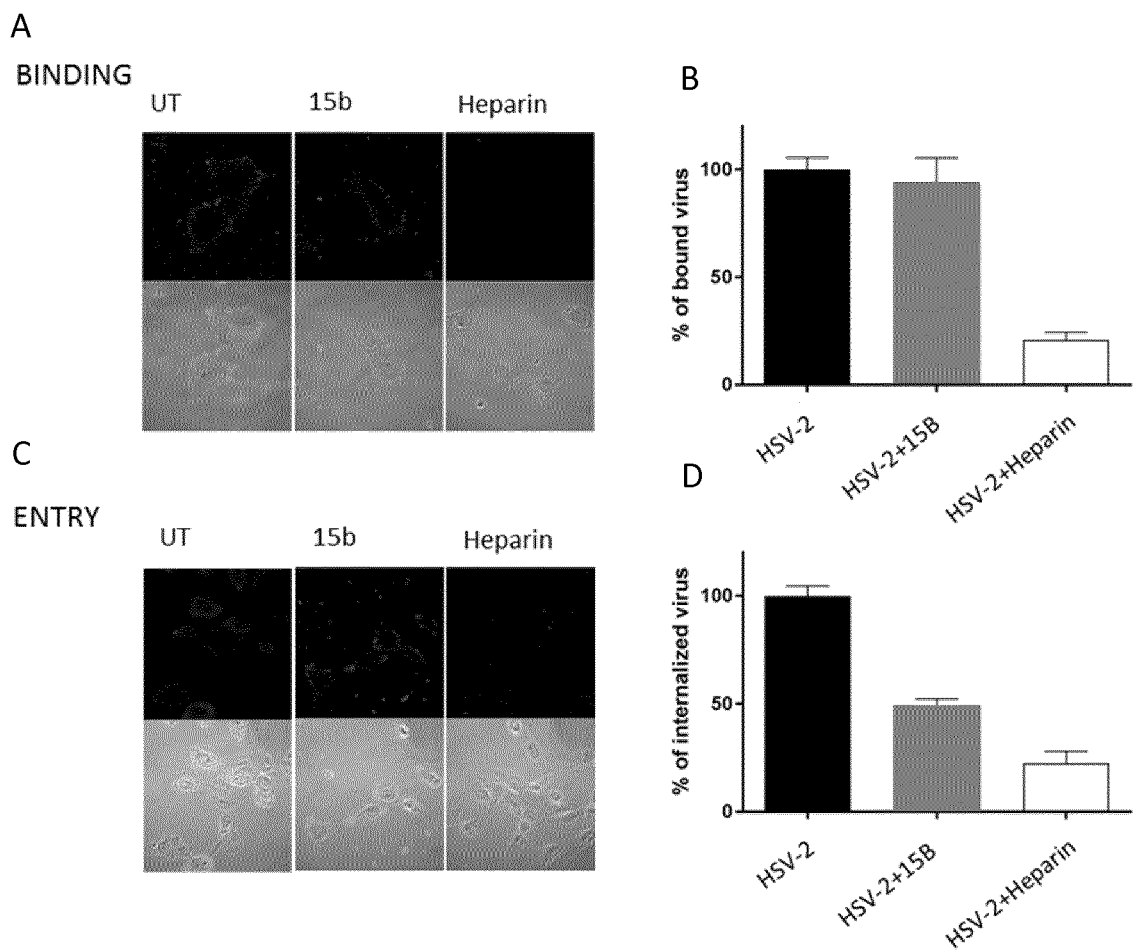
FIG. 3: Mechanism of action. (A) Evaluation of binding of virus to cell evaluated through immunofluorescence (IF) in VERO untreated cells infected with HSV-2 (UT), in VERO cells infected with HSV-2 treated with compound 15b (10 µM), in VERO cells treated with Heparin as control. (B) Evaluation of and entry of virus into cells evaluated through IF in VERO untreated cells infected with HSV-2 (UT), in VERO cells infected with HSV-2 treated with compound 15b (10 µM), in VERO cells treated with Heparin as control. (C) Percentage of virus bound to the cells evaluated through ELISA in VERO cells infected with HSV-2, in VERO cells infected with HSV-2 treated with compound 15b (10 µM), in VERO cells treated with Heparin as control. (D) Percentage of virus internalized into the cells evaluated through ELISA in VERO cells infected with HSV-2, in VERO cells infected with HSV-2 treated with compound 15b (10 µM), in VERO cells treated with Heparin as control.

IF experiments demonstrate that compound 15b is not impairing viral binding, although 15b decreased the percentage of internalized virus (FIG. 3).

In order to better understand the mechanism of action of compounds against enveloped viruses, the effect of compounds on the membranes was investigated. The oxidation of the lipids is a well-known mechanism that induces destabilization of the membranes due to the alteration of the lipids' polarity. In fact free radicals produced cis-trans isomerization of the polyunsaturated fatty acids and the formation of highly hydrophilic groups that are able to destabilize the lipid bilayer.

More in detail the lipid oxidation capability of 15b was evaluated by performing a lipoperoxidation test. Results in FIG. 4 clearly confirmed that compound 15b is able to oxidize polyunsaturated fatty acids through the formation of free radicals, thus impairing membrane fluidity. The addition of 0.05% w/w (±)-α-tocopherol reduced the oxidation of linoleic acid further confirming the oxidative mechanism.

Furthermore, in the virucidal assay, the inventors investigated whether compound 15b was able to inhibit multiple cycles of infection when added post-infection. Compound 15b maintained a good antiviral activity value of 775 nM against HSV-2 infected cells.

CONCLUSIONS

In conclusion, the antiviral activity of the compounds of the invention was evaluated by in vitro cellular assays. The antiviral activity of compounds was also evaluated with HSV-2 strains carrying resistance mutations conferring high level resistance to acyclovir (Table 5). The results obtained and reported in the Examples show that the compounds of the invention were able to suppress HIV-1 replication in infected cells; suppress Zika virus (ZKV) replication in infected cells; suppress Herpes 1 virus (HSV-1) replication in infected cells; suppress Herpes 1 virus (HSV-2) replication in infected cells; suppress Influenza virus (IV) replication in infected cells; suppress Respiratory Syncytial Virus (RSV) replication in infected cells; suppress Cytomegalovirus (CMV) replication in infected cells, suppress Vesicular Stomatitis Virus (VSV) replication in infected cells and suppress Dengue virus (DENV) replication in infected cells.

Tested compounds are active against enveloped viruses only (Table 5).

Further several assays were performed to better understand the mechanism of action of the present compounds against enveloped viruses.

The study of mechanism of action, in particular pretreatment and post-treatment assays, indicates that compounds' activity is not due to interaction with the human cellular membrane (FIG. 1).

Further, in the binding of virus to cell assay, the percentage of bound virus in HSV-2 infected Vero cells as measured with specific antibodies is the same in cells exposed to compound 15b and in control cells (HSV-2 infected Vero cells without 15b) (FIG. 2C). On the other hand, the percentage of internalized virus is lower for HSV-2 infected Vero cells exposed to 15b (FIG. 2D). This result demonstrates that compounds' activity is not due to the inhibition of viral entry.

For all these reasons, it is believed that compounds act via an oxidative mechanism towards lipids in the viral envelope. This oxidative ability is linked to the production of free radicals and has been validated with the lipid peroxidation test.

REFERENCES

1. Tintori C, Corradi V, Magnani M, Manetti F, Botta M. Targets looking for drugs: a multistep computational protocol for the development of structure-based pharmacophores and their applications for hit discovery. J ChemInf Model. 2008 November; 48(11):2166-79.
2. Rinaldi M, Tintori C, Franchi L, Vignaroli G, Innitzer A, Massa S, Esté J A, Gonzalo E, Christ F, Debyser Z, Botta M. A versatile and practical synthesis toward the development of novel HIV-1 integrase inhibitors. Chem Med Chem. 2011 Feb. 7; 6(2):343-52.
3. Tiberi M, Tintori C, Ceresola E R, Fazi R, Zamperini C, Calandro P, Franchi L, Selvaraj M, Botta L, Sampaolo M, Saita D, Ferrarese R, Clementi M, Canducci F, Botta M. 2-Aminothiazolones as anti-HIV agents that act as gp120-CD4 inhibitors. Antimicrob Agents Chemother. 2014 June; 58(6):3043-52.
4. Anthony, S. J. et al. A Strategy To Estimate Unknown Viral Diversity in Mammals. mBio 4, e00598-13 (2013).
5. Arouri, A. & Mouritsen, O. G. Membrane-perturbing effect of fatty acids and lysolipids. Prog. Lipid Res. 52, 130-140 (2013).
6. Pollock, S. et al. Polyunsaturated liposomes are antiviral against hepatitis B and C viruses and HIV by decreasing cholesterol levels in infected cells. Proc. Natl. Acad. Sci. U.S.A. 107, 17176-17181 (2010).
7. Sample, C. J. et al. A mastoparan-derived peptide has broad-spectrum antiviral activity against enveloped viruses. Peptides 48, 96-105 (2013).
8. Sandra T. Cooper and Paul L. McNeil Membrane Repair: Mechanisms and Pathophysiology Physiol Rev. 2015 October; 95(4): 1205-1240.
9. M. Donalisio et al., The AGMA poly(amidoamine) inhibits the infectivity of herpes simplex virus in cell lines, in human cervicovaginal histocultures, and in vaginally infected mice. Biomaterials. 85, 40-53 (2016).
10. V. Cagno et al., In vitro evaluation of the antiviral properties of Shilajit and investigation of its mechanisms of action. J Ethnopharmacol. 166, 129-134 (2015).
11. V. Cagno et al., Highly sulfated K5 *Escherichia coli* polysaccharide derivatives inhibit respiratory syncytial virus infectivity in cell lines and human tracheal-bronchial histocultures. Antimicrob. Agents Chemother. 58, 4782-4794 (2014).
12. A. Civra et al., Identification of Equine Lactadherin-derived Peptides That Inhibit Rotavirus Infection via Integrin Receptor Competition. J. Biol. Chem. 290, 12403-12414 (2015).
13. V. Cagno et al., The agmatine-containing poly(amidoamine) polymer AGMA1 binds cell surface heparan sulfates and prevents attachment of mucosal human papillomaviruses. Antimicrob. Agents Chemother. 59, 5250-5259 (2015).
14. S. Pfaender et al., Inactivation of Zika virus in human breast milk by prolonged storage or pasteurization. Virus Research. 228, 58-60 (2017).
15. Boon-Huat Bay, Yuan-Kun Lee, Benny Kwong-Huat Tan, Eng-Ang Ling, Lipid peroxidative stress and antioxidative enzymes in brains of milk-supplemented rats, Neuroscience Letters 277 (1999) 127-130).

The invention claimed is:

1. A compound selected from the group consisting of:

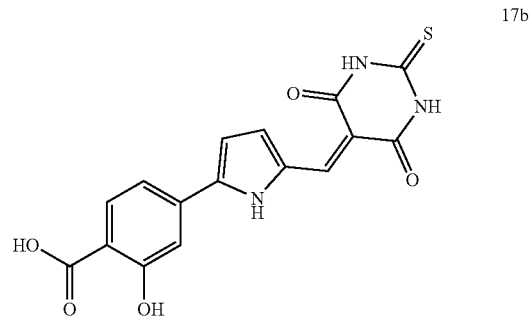

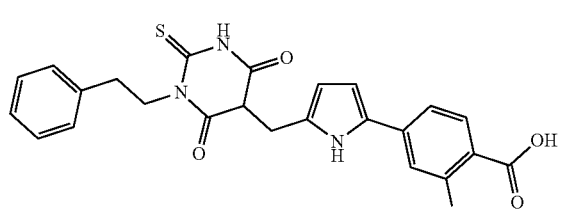

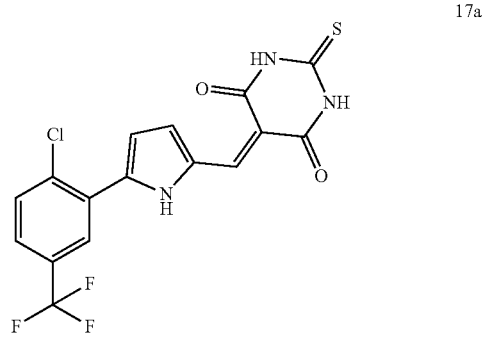

-continued
15a
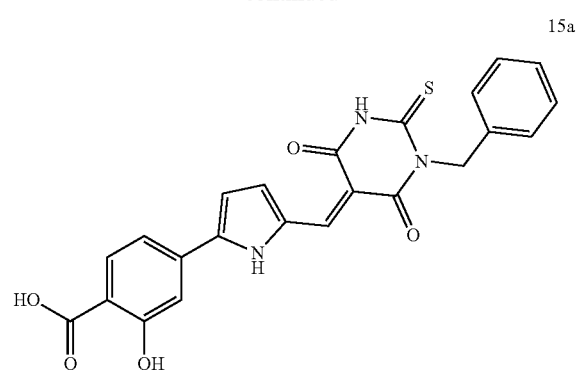
15b
15c
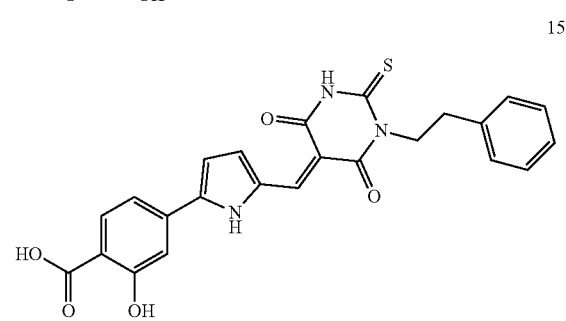
1p;1p
15d
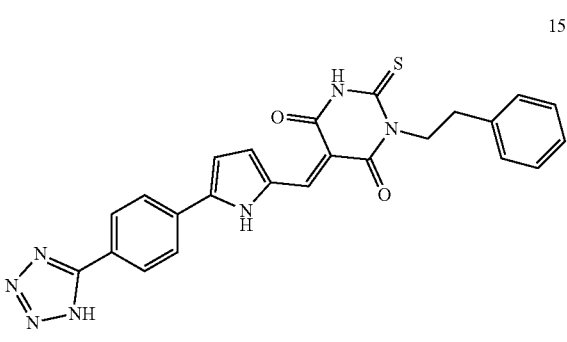
15e
-continued
15f
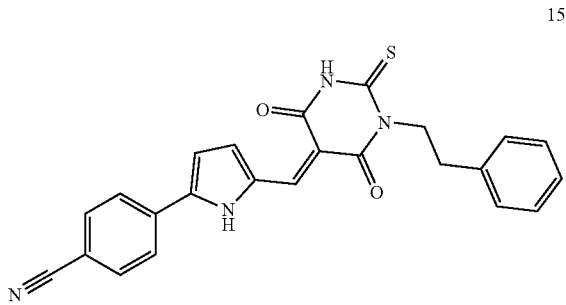
15g
15h
15i
15j

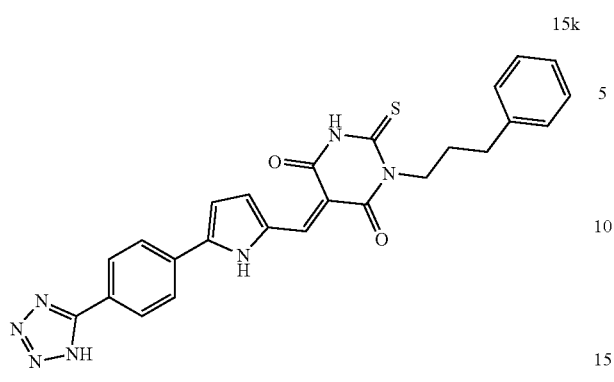
15k
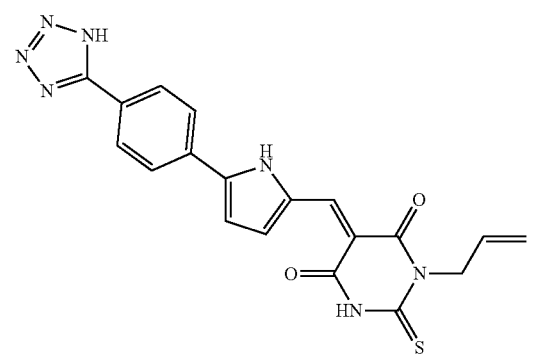
15o
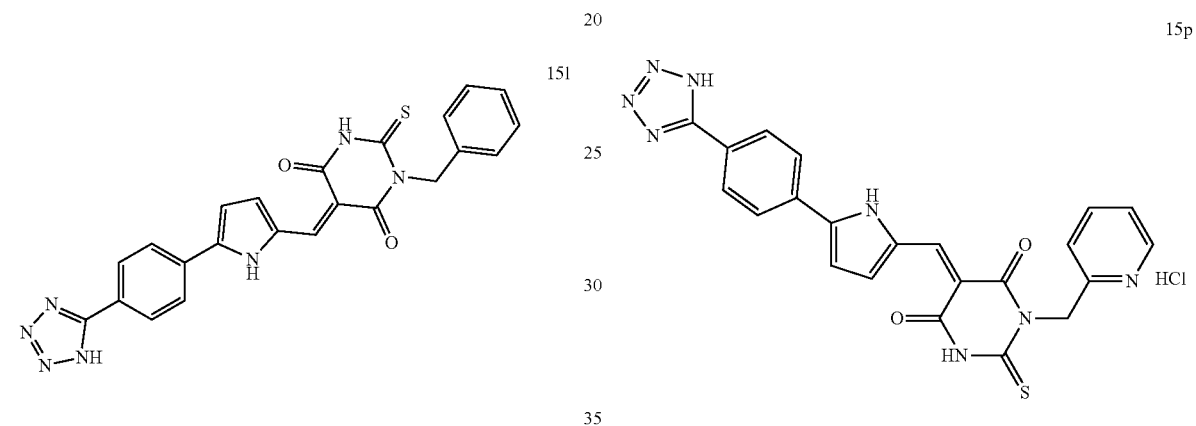
15l
15p
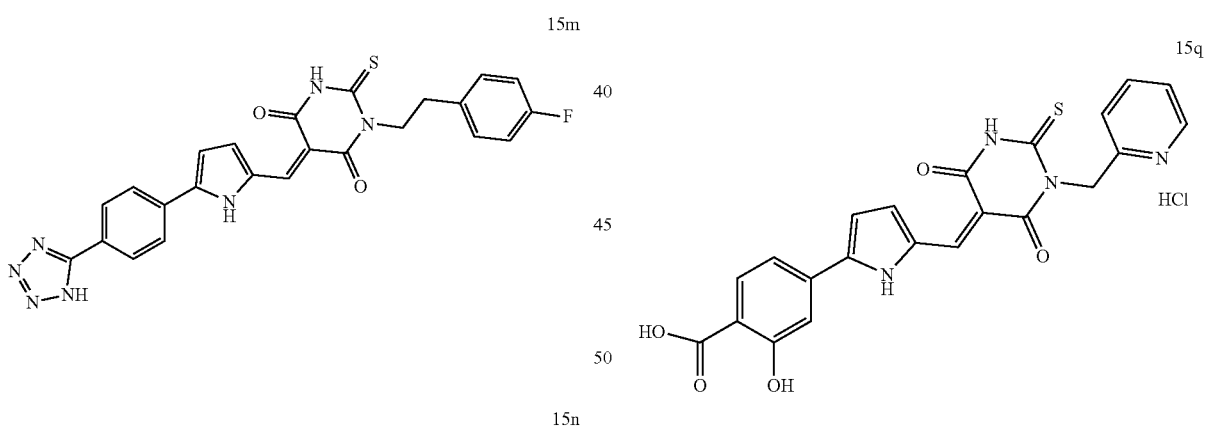
15m
15q
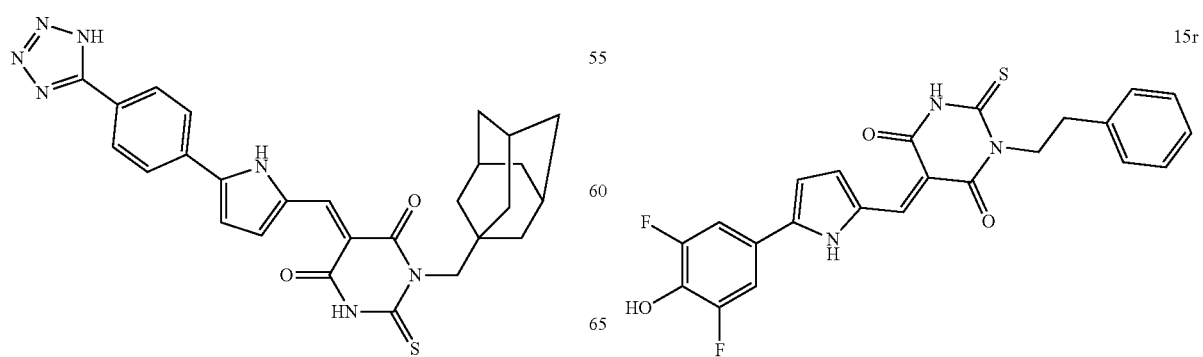
15n
15r -continued

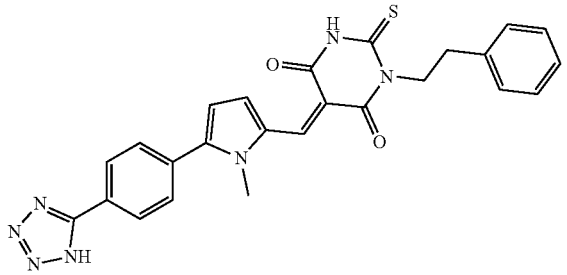

15s or salt, solvate or stereoisomer thereof.

2. A method of destabilizing a viral envelope of a virus in a patient, comprising administering an effective amount of a compound of claim 1 or salt, solvate, or stereoisomer thereof to a patient in need thereof, wherein said compound or salt, solvate, or stereoisomer thereof destabilizes the viral envelope of said virus in said patient.

3. A method for the treatment of a viral disease caused by an enveloped virus, comprising administering an effective amount of a compound of claim 1 or salt, solvate or stereoisomer thereof to a patient in need thereof.

4. The method according to claim 3, wherein the enveloped virus is selected from the group consisting of: Human Immunodeficiency Virus 1 (HIV-1), Human Immunodeficiency Virus 2 (HIV-2), Herpes I virus (HSV-1), Herpes 2 virus (HSV-2), Influenza Virus, Respiratory Syncytial Virus (RSV), Cytomegalovirus (CMV), Zika Virus (ZKV), Dengue Virus, West Nile Virus, Lassa Virus, Ebola Virus, Lloviu virus, Bundibugyo virus, Reston virus, Sudan virus, Tai Forest virus, Marburg virus, Ravn virus (RAVV), Pneumovirus, Junin Virus, Rift Valley fever virus, La Crosse Virus, Porcine Reproductive And Respiratory Syndrome Virus, Poxvirus, Bovine Viral Diarrhea Norovirus, SARS Coronavirus, Chikunguya Virus, Hepatitis C Virus, Hepatitis B Virus, Schmallenberg virus, African swine fever virus, Eastern Equine Encephalitis Virus, Cowpox virus, Western Equine Encephalitis Virus, Nipah Virus, Omsk hemorrhagic fever Virus, Venezuelan Equine Encephalitis Virus, Human parainfluenza viruses, Japanese Encephalitis Virus, Tick Borne Encephalitis Virus, Russian spring-summer encephalitis (RSSE) virus, Yellow Fever Virus, Newcastle Virus, Virus (BVDV), Parainfluenza virus type 5 (PIV5), Border Disease Virus (BDV) of sheep, Classical Swine Fever Virus (CSFV), Vesicular Stomatitis Virus (VSV) and HSV-2 acyclovir resistant (HSV-2 Acy R), optionally the enveloped virus is selected from the group consisting of: HIV-1, HSV-1, HSV-2, HCMV, RSV, VSV, HiN1, DENV-2 and ZKV.

5. The method according to claim 3, wherein the enveloped virus is resistant to an antiviral agent, said antiviral agent optionally being selected from the group consisting of: acyclovir, ribavirine, a nucleoside analogue reverse-transcriptase inhibitor, a non-nucleoside analogue reverse-transcriptase inhibitor, a nucleotide analogue reverse-transcriptase inhibitor, an integrase inhibitor, a NS3/4A serine protease inhibitor, a NS5B polymerase inhibitor, interferon alpha, Maraviroc, Highly active antiretroviral therapy (HAART), Brivudin, Famiciclovir, Penciclovir, Ganciclovir, Amantadine, Rimantadine, Oseltamivir and Zanamivir, optionally the nucleoside analogue reverse-transcriptase inhibitor is selected from the group consisting of: Zidovudine, Didanosine, Lamivudine, Emtricitabine and stavudine; optionally the non-nucleoside analogue reverse-transcriptase inhibitor is selected from the group consisting of: Efavirenz, Nevirapine, Etravirine and Rilpivirine; optionally the nucleotide analogue reverse-transcriptase inhibitor is Tenofovir; optionally the integrase inhibitor is selected from the group consisting of; Raltegravir, dolutegravir and elvitegravir; optionally the NS3/4A serine protease inhibitor is selected from the group consisting of: Boceprevir, Telaprevir and paritaprevir; optionally the NS5B polymerase inhibitor is selected from the group consisting of: ledipasvir, ombitasvir, Dasabuvir and Sofosbuvir; optionally the Highly active antiretroviral therapy (HAART) is selected from the group consisting of: Triumeq, Trizivir and Stribild.

6. The method according to claim 2, further comprising administering in combination a further antiviral agent, said further antiviral agent being optionally selected from the group consisting of: acyclovir, ribavirine, a nucleoside analogue reverse-transcriptase inhibitor, a non-nucleoside analogue reverse-transcriptase inhibitor, a nucleotide analogue reverse-transcriptase inhibitor, an integrase inhibitor, a NS3/4A serine protease inhibitor, a NS5B polymerase inhibitor, interferon alpha, Maraviroc, Highly active antiretroviral therapy (HAART), Enfuvirtide, Entecavir, Lamivudine, Brivudin, Famiciclovir, Penciclovir, Ganciclovir, Amantadine, Rimantadine, Oseltamivir and Zanamivir.

7. The method according to claim 6, wherein the nucleoside analogue reverse-transcriptase inhibitor is selected from the group consisting of: Zidovudine, Didanosine, Lamivudine, Emtricitabine and stavudine; the non-nucleoside analogue reverse-transcriptase inhibitor is selected from the group consisting of: Efavirenz, Nevirapine, Etravirine and Rilpivirine; the nucleotide analogue reverse-transcriptase inhibitor is Tenofovir; the integrase inhibitor is selected from the group consisting of: Raltegravir, dolutegravir and elvitegravir; the NS3/4A serine protease inhibitor is selected from the group consisting of: Boceprevir, Telaprevir and paritaprevir; the NS5B polymerase inhibitor is selected from the group consisting of: ledipasvir, ombitasvir, Dasabuvir and Sofosbuvir, and/or the Highly active antiretroviral therapy (HAART) is selected from the group consisting of: Triumeq, Trizivir and Stribild.

8. A pharmaceutical composition comprising a compound or salt, solvate or stereoisomer of claim 1 and a pharmaceutically acceptable excipient and/or diluent.

9. The pharmaceutical composition according to claim 8, further comprising an additional antiviral agent, said additional antiviral agent being optionally selected from the group consisting of: acyclovir, ribavirine, a nucleoside analogue reverse-transcriptase inhibitor, a non-nucleoside analogue reverse-transcriptase inhibitor, a nucleotide analogue reverse-transcriptase inhibitor, an integrase inhibitor, a NS3/4A serine protease inhibitor, a NS5B polymerase inhibitor, interferon alpha, Maraviroc, Highly active antiretroviral therapy (HAART), Enfuvirtide, Entecavir, Lamivudine, Brivudin, Famiciclovir, Penciclovir, Ganciclovir, Amantadine, Rimantadine, Oseltamivir and Zanamivir, optionally the nucleoside analogue reverse-transcriptase inhibitor is selected from the group consisting of: Zidovudine, Didanosine, Lamivudine, Emtricitabine and stavudine; optionally the non-nucleoside analogue reverse-transcriptase inhibitor is selected from the group consisting of: Efavirenz, Nevirapine, Etravirine and Rilpivirine; optionally the nucleotide analogue reverse-transcriptase inhibitor is Tenofovir; optionally the integrase inhibitor is selected from the group consisting of: Raltegravir, dolutegravir and elvitegravir; optionally the NS3/4A serine protease inhibitor is selected from the group consisting of: Boceprevir, Telaprevir and paritaprevir; optionally the NS5B polymerase inhibitor is selected from the group consisting of: ledipasvir, ombitasvir, Dasabuvir and Sofosbuvir; optionally the Highly active antiretroviral therapy (HAART) is selected from the group consisting of: Triumeq, Trizivir and Stribild.

10. The pharmaceutical composition according to claim 8 wherein said pharmaceutical composition is for topical administration.

11. The pharmaceutical composition according to claim 8 wherein said pharmaceutical composition is formulated as a vaginal capsule or as a nasal spray.

* * * * *